US012663420B2

(12) United States Patent
Li et al.

(10) Patent No.: US 12,663,420 B2
(45) Date of Patent: Jun. 23, 2026

(54) **DNAZYMES FOR DETECTING *LEGIONELLA PNEUMOPHILA***

(71) Applicant: McMaster University, Hamilton (CA)

(72) Inventors: Yingfu Li, Dundas (CA); Meghan Rothenbroker, Aurora (CA); Erin M. McConnell, Orleans (CA); Carlos D. M. Filipe, Ancaster (CA); Jimmy Gu, Mississauga (CA)

(73) Assignee: MCMASTER UNIVERSITY, Hamilton (CA)

( * ) Notice: Subject to any disclaimer, the term of this patent is extended or adjusted under 35 U.S.C. 154(b) by 1096 days.

(21) Appl. No.: 17/705,000

(22) Filed: Mar. 25, 2022

(65) Prior Publication Data

US 2022/0317123 A1 Oct. 6, 2022

Related U.S. Application Data

(60) Provisional application No. 63/166,553, filed on Mar. 26, 2021.

(51) Int. Cl.

| | |
|---|---|
| ***C12Q 1/68*** | (2018.01) |
| ***C12N 15/113*** | (2010.01) |
| ***G01N 33/542*** | (2006.01) |
| ***G01N 33/569*** | (2006.01) |

(52) U.S. Cl.
CPC ...... *G01N 33/56911* (2013.01); *C12N 15/113* (2013.01); *G01N 33/542* (2013.01); *C12N 2310/127* (2013.01); *G01N 2333/922* (2013.01)

(58) Field of Classification Search
None
See application file for complete search history.

(56) References Cited

PUBLICATIONS

Rothenbroker et al; Anew. Chem. Int. Ed., 2021, vol. 60, pp. 4782-4788, and supporting information.*

Hoinka et al. Large scale analysis of the mutational landscape in HT-SELEX improves aptamer discovery. Nucleic Acids Research, vol. 43, published online Apr. 13, 2015, pp. 5699-5707.

Hoinka et al. AptaCluster—A Method to Cluster HT-SELEX Aptamer Pools and Lessons from Its Application. Research in Computational Molecular Biology. RECOMB 2014. Lecture Notes in Computer Science, vol. 8394, published Apr. 2014, pp. 115-128.

Alam et al. FASTAptamer: A Bioinformatic Toolkit for High-throughput Sequence Analysis of Combinatorial Selections. Molecular Therapy—Nucleic Acids, vol. 4(3), published Mar. 3, 2015, pp. 1-10.

(Continued)

*Primary Examiner* — Jehanne S Sitton
(74) *Attorney, Agent, or Firm* — SMART & BIGGAR LP

(57) ABSTRACT

This disclosure relates to DNAzymes and biosensors for detecting pathogenic bacteria, and in particular, for detecting *Legionella pneumophila*. This disclosure also provides a method for detecting the presence of *Legionella pneumophila* in a test sample, comprising: a) contacting said test sample with the DNAzyme or biosensor described herein, wherein the DNAzyme comprises a detectable label; b) allowing cleavage of the DNAzyme if a target is present, thereby releasing the detectable label; and c) measuring a detectable signal if the portion of the DNAzyme comprising the detectable label is released, wherein the RNA cleavage activity of the DNAzyme is activated by a target from *Legionella pneumophila*.

20 Claims, 28 Drawing Sheets

Specification includes a Sequence Listing.

| Name | Truncations | Length |
|---|---|---|
| MET1 | ④⑨ | 77 |
| MET2 | ④⑨② | 63 |
| MET3 | ④⑨⑧② | 55 |
| MET4 | ④⑨①⑥ | 55 |
| MET5 | ④⑨③ | 67 |
| MET6 | Same as MET4 but with insertion of 4T at ◄-● | 59 |
| MET7 | Same as 4TFP but with insertion of 2T at ◄-● | 101 |
| MET8 | Same as MET4 but with 5'-TA-3' insertion at ●-► | 57 |
| MET9 | Same as MET8 but with insertion of 4T at ◄-● | 61 |
| MET10 | ④⑨①⑥⑦ | 55 |
| MET11 | Same as MET10 but with insertion of 5'-CTA-3' at ◄-● and 5'-TAG-3' at the 3'-terminal | 61 |
| MET12 | ④⑨①⑥⑦⑤ | 51 |
| MET13 | Same as MET10 but with insertion of 4T at ◄-● | 59 |

(56) References Cited

PUBLICATIONS

Reuter and Mathews. RNAstructure: software for RNA secondary structure prediction and analysis. BMC Bioinformatics, 11(129), available at http://www.biomedcentral.com/1471-2105/11/129, published Mar. 15, 2010, pp. 1-9.
Zuker. Mfold web server for nucleic acid folding and hybridization prediction. Nucleic Acids Research, vol. 31(13), published Jul. 1, 2003, pp. 3406-3415.
Lake et al. DNAzymes as Activity-Based Sensors for Metal Ions: Recent Applications, Demonstrated Advantages, Current Challenges, and Future Directions. Accounts of Chemical Research, vol. 52, published Nov. 13, 2019, pp. 3275-3286.
Ma and Liu. An In Vitro Selected DNAzyme Mutant Highly Specific for $Na^+$ in Slightly Acidic Conditions. Accepted Manuscript. ChemBioChem, vol. 20(4), published online Aug. 15, 2018, 17 pages.
Wachowius et al. Combinatorial Mutation Interference Analysis Reveals Functional Nucleotides Required for DNA Catalysis. Angewandte Chemie International Edition, vol. 49(45), first published Sep. 24, 2010, pp. 8504-8508.
Fraser et al. Legionnaires' Disease: Description of an Epidemic of Pneumonia. The New England Journal of Medicine, vol. 297(22), published Dec. 1, 1977, pp. 1189-1197.
Horwitz. The Legionnaires' disease bacterium (*Legionella pneumophila*) inhibits phagosome-lysosome fusion in human monocytes. Journal of Experimental Medicine, vol. 158, published Dec. 1983, pp. 2108-2126.
Horwitz. Phagocytosis of the legionnaires' disease bacterium (*Legionella pneumophila*) occurs by a novel mechanism: Engulfment within a Pseudopod coil. Cell, vol. 36, published Jan. 1984, pp. 27-33.
Horwitz and Silverstein. Legionnaires' disease bacterium (*Legionella pneumophila*) multiples intracellularly in human monocytes. Journal of Clinical Investigation, vol. 66, published Sep. 1980, pp. 441-450.
Horwitz and Maxfield. Legionella pneumophila inhibits acidification of its phagosome in human monocytes. Journal of Cell Biology, vol. 99, published Dec. 1984, pp. 1936-1943.
Diederen. *Legionella* spp. and Legionnaires' disease. Journal of Infection, vol. 56, avalable online Nov. 5, 2007, pp. 1-12.
Stout and Yu. Legionellosis. The New England Journal of Medicine, vol. 337, published Sep. 4, 1997, pp. 682-687.
Tronel and Hartemann. Overview of diagnostic and detection methods for legionellosis and *Legionella* spp. Letters in Applied Microbiology, vol. 48(6), published online Mar. 7, 2009, pp. 653-656.
McClung et al. Waterborne Disease Outbreaks Associated With Environmental and Undetermined Exposures to Water—United States, 2013-2014. Morbidity and Mortality Weekly Report, vol. 66(44), published Nov. 10, 2017, pp. 1222-1225.
World Health Organization. Legionella and the prevention of legionellosis. Published Apr. 11, 2007, 276 pages.
Palazzolo et al. Legionella pneumonia: increased risk after COVID-19 lockdown? Italy, May to Jun. 2020. Euro surveillance: bulletin Europeen sur les maladies transmissibles = European communicable disease bulletin, vol. 25(30), published Jul. 30, 2020, pp. 1-3.
Hollenstein. DNA Catalysis: The Chemical Repertoire of DNAzymes. Molecules, vol. 20(11), published Nov. 20, 2015, pp. 20777-20804.
Burstein et al. Genomic analysis of 38 *Legionella* species identifies large and diverse effector repertoires. Nature Genetics, vol. 48(2), published online Jan. 11, 2016, pp. 167-175 and 3 pages of online methods.
Rao et al. Active and adaptive Legionella CRISPR-Cas reveals a recurrent challenge to the pathogen. Cellular Microbiology, vol. 18(10), published online Mar. 31, 2016, pp. 1319-1338.
Braun et al. Quantification of Viable but Non-Culturable Cells of Legionella pneumophila. Methods in Molecular Biology, vol. 1921, published online Jan. 30, 2019, pp. 45-53.
Feeley et al. Charcoal-yeast extract agar: primary isolation medium for Legionella pneumophila. Journal of Clinical Microbiology, vol. 10(4), published Oct. 1979, pp. 437-441.
Chatfield and Cianciotto. Culturing, media, and handling of legionella. Methods in Molecular Biology, vol. 954, published online Oct. 17, 2012, pp. 151-162.
Shen et al. A Catalytic DNA Activated by a Specific Strain of Bacterial Pathogen. Angewandte Chemie, vol. 128, published online Dec. 16, 2015, pp. 2477-2480 (AKA Angewandte Chemie International Edition, vol. 55, published online Dec. 16, 2015, pp. 2431-2434).
Zhang et al. In vitro selection of RNA-cleaving DNAzymes for bacterial detection. Methods, vol. 106, published online Mar. 24, 2016, pp. 66-75.
Li and Breaker. In vitro selection of kinase and ligase deoxyribozymes. Methods, vol. 23, published Feb. 2011, pp. 179-190.
Schlosser et al. In vitro selection of small RNA-cleaving deoxyribozymes that cleave pyrimidine-pyrimidine junctions. Nucleic Acids Research, vol. 36 (14), published online Jul. 21, 2008, pp. 4768-4777.
Jares-Erijman and Jovin. FRET imaging. Nature Biotechnology, vol. 21 (11), published online Oct. 31, 2002, pp. 1387-1395.
Mei et al. An efficient RNA-cleaving DNA enzyme that synchronizes catalysis with fluorescence signaling. Journal of the American Chemical Society, vol. 125, published online Dec. 13, 2002, pp. 412-420.
Rothenbroker et al. Selection and Characterization of an RNA-cleaving DNAzyme Specifically Activated by Legionella pneumophila. Angewandte Chemie International Edition, vol. 60(9), first published Nov. 13, 2020, pp. 4782-4788.
Tuerk and Gold. Systematic evolution of ligands by exponential enrichment: RNA ligands to bacteriophage T4 DNA polymerase. Science, vol. 249(4968), published Aug. 3, 1990, pp. 505-510.
Ellington and Szostak. In vitro selection of RNA molecules that bind specific ligands. Nature, vol. 346, published Aug. 30, 1990, pp. 818-822.
Ali et al. Fluorogenic DNAzyme Probes as Bacterial Indicators. Angewandte Chemie, vol. 123 (16), published online Mar. 15, 2011, pp. 3835-3838 (AKA Angewandte Chemie International Edition, vol. 50, published Sep. 5, 2011, pp. 3751-3754).
Chang et al. An Unintentional Discovery of a Fluorogenic DNA Probe for Ribonuclease I. ChemBioChem, vol. 21, published Feb. 17, 2020 (accepted manuscript online Aug. 16, 2019), pp. 464-468.
Cunha et al. Legionnaires' disease. Lancet, vol. 387, published online Jul. 29, 2015, pp. 376-385.
Yu et al. Distribution of *Legionella* Species and Serogroups Isolated by Culture in Patients with Sporadic Community-Acquired Legionellosis: An International Collaborative Survey. The Journal of Infectious Diseases, vol. 186, published online May 21, 2002, pp. 127-128.
Gu et al. Selection of DNAzymes for Sensing Aquatic Bacteria: *Vibrio anguillarum*. Analytical Chemistry, vol. 91, published May 22, 2019, pp. 7887-7893.
Duda et al. Lack of correlation between Legionella colonization and microbial population quantification using eterotrophic plate count and adenosine triphosphate bioluminescence measurement. Environmental Monitoring and Assessment, vol. 187(393), published Jun. 3, 2015, 187:393 pp. 1-10.
Liu et al. Discovery and Biosensing Applications of Diverse RNA-Cleaving DNAzymes. Accounts of Chemical Research, vol. 50, published Aug. 14, 2017, pp. 2273-2283.
Ali et al. A DNAzyme-Based Colorimetric Paper Sensor for Helicobacter pylori. Angewandte Chemie International Edition, vol. 58(29), first published May 16, 2019, pp. 9907-9911.
Gysbers et al. Evolution of an Enzyme from a Noncatalytic Nucleic Acid Sequence. Scientific Reports, vol. 5, published Jun. 19, 2015, pp. 1-8.
Gu et al. Reselection Yielding a Smaller and More Active Silver-Specific DNAzyme. ACS Omega, vol. 3, published Nov. 9, 2018, pp. 15174-15181.
Yu et al. Screening of DNAzyme mutants for highly sensitive and selective detection of calcium in milk. Analytical Methods, vol. 10, published Mar. 15, 2018, pp. 1740-1746.

(56) References Cited

PUBLICATIONS

Bhatnagar et al. Protein stability during freezing: separation of stresses and mechanisms of protein stabilization. Pharmaceutical Development and Technology, vol. 12(5), published online Oct. 7, 2008, pp. 505-523.
Gao et al. Post-SELEX optimization of aptamers. Analytical and Bioanalytical Chemistry, vol. 408, published online May 12, 2016, pp. 4567-4573.
Sharma et al. ABCs of DNA aptamer and related assay development. Biotechnology Advances, vol. 35(2), published online Jan. 18, 2017, pp. 275-301.
Lam et al. Characterization of non-8-17 sequences uncovers structurally diverse RNA-cleaving deoxyribozymes. Molecular BioSystems, vol. 7, published Apr. 27, 2011, pp. 2139-2146.
Frost et al. An in solution assay for interrogation of affinity and rational minimer design for small molecule-binding aptamers. Analyst, vol. 140, published Aug. 24, 2015, pp. 6643-6651.
Silverman. Artificial Functional Nucleic Acids: Aptamers, Ribozymes, and Deoxyribozymes Identified by In Vitro Selection. Functional Nucleic Acids for Analytical Applications, published May 27, 2009, pp. 47-108.
Cheng et al. Relations between the loop transposition of DNA G-quadruplex and the catalytic function of DNAzyme. Biochimica et Biophysica Acta—General Subjects, vol. 1861, published online May 19, 2017, pp. 1913-1920.
Brown et al. Biochemical Characterization of a Uranyl Ion-Specific DNAzyme. ChemBioChem, vol. 10(3), published Feb. 13, 2009, pp. 486-492.
Zaborowska et al. Deletion analysis in the catalytic region of the 10-23 DNA enzyme. Federation of European Biochemical Societies. Letters, vol. 579(2), published online Dec. 18, 2004, pp. 554-558.
Zhou et al. A DNAzyme requiring two different metal ions at two distinct sites. Nucleic Acids Research, vol. 44(1), published online Dec. 10, 2015, pp. 354-363.
Schlosser et al. A genotype-to-phenotype map of in vitro selected RNA-cleaving DNAzymes: implications for accessing the target phenotype. Nucleic Acids Research, vol. 37, published online Apr. 8, 2009, pp. 3545-3557.
Lehman and Unrau. Recombination During In Vitro Evolution. Journal of Molecular Evolution, vol. 61, published online Jun. 30, 2005, pp. 245-252.

* cited by examiner

FIG. 1A
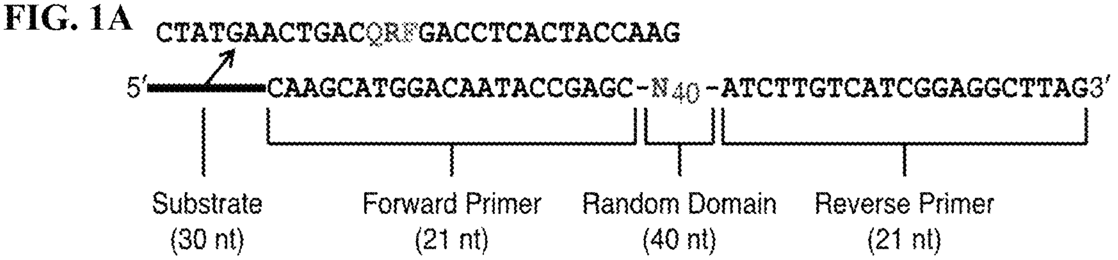
FIG. 1B
CTTTCATTTCAGCCGATCATACCTCAATGTAGATAAGCAC
FIG. 1C
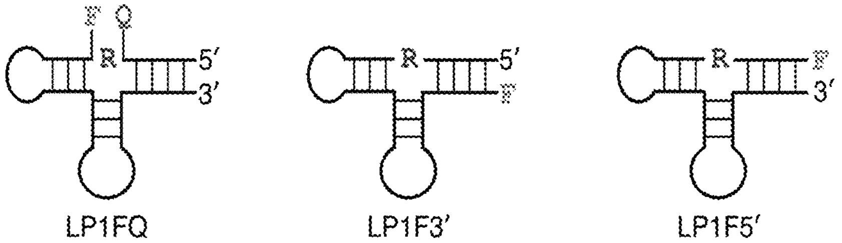
FIG. 1A     CTATGAACTGACQRᶠGACCTCACTACCAAG
5'━━━━CAAGCATGGACAATACCGAGC-N$_{40}$-ATCTTGTCATCGGAGGCTTAG3'
Substrate     Forward Primer     Random Domain     Reverse Primer
(30 nt)     (21 nt)     (40 nt)     (21 nt)
FIG. 1B     CTTTCATTTCAGCCGATCATACCTCAATGTAGATAAGCAC
LP1FQ     LP1F3'     LP1F5'

| DNAzyme | $Y_{max}$ (%) | $k_{obs}$ ($min^{-1}$) |
|---|---|---|
| LP1F3' ——●—— | 97 ± 1 | 0.125 ± 0.005 |
| LP1P - - - ▲- - | 92 ± 1 | 0.103 ± 0.007 |
| LP1F5' - - ■ - - | 99 ± 2 | 0.040 ± 0.002 |

FIG. 7A
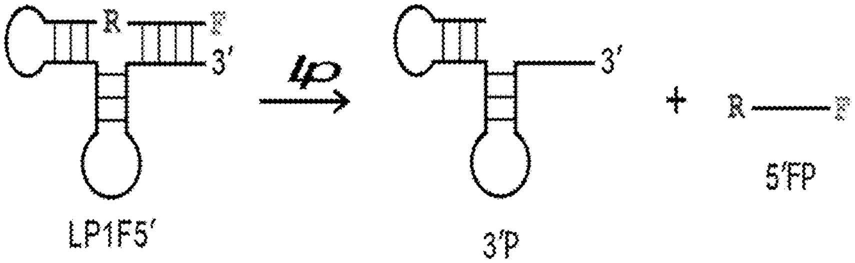
FIG. 7B
| Location | # of samples | Avg % clv | SD |
|---|---|---|---|
| Quebec | 22 | 89 | 12 |
| Pennsylvania | 33 | 83 | 11 |
| New Jersey | 1 | 92 | - |
| Ohio | 1 | 82 | - |
FIG. 7C
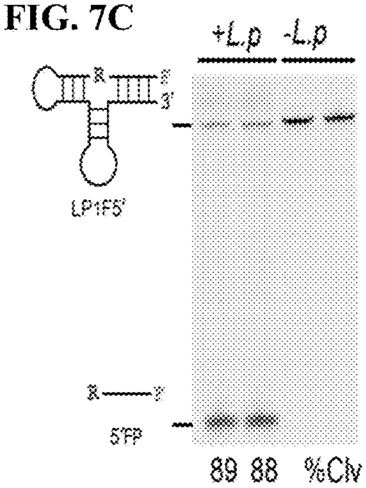

Probability >= 99%
99% > Probability >= 95%
95% > Probability >= 90%
90% > Probability >= 80%
80% > Probability >= 70%
70% > Probability >= 60%
60% > Probability >= 50%
50% > Probability

ENERGY = -8.5 LP1

| **DNAzyme** | *K. aerogenes* | *K. pneumoniae* | *E. aerogenes* | *E. cloacae* | *S. enterica* | *E. coli K12* | *S. sonnei* | *S. flexeri* | *L. pneumophila* |
|---|---|---|---|---|---|---|---|---|---|
| | Average % cleavage | | | | | | | | |
| LP1FQ | 2 | 2 | 2 | 3 | 3 | 3 | 4 | 4 | 12 |
| LP1QF | 3 | 2 | 4 | 8 | 4 | 6 | 2 | 2 | 1 |
| LP1F3' | 21 | 13 | 9 | **96** | **97** | **95** | 14 | 10 | 82 |
| LP1Q | 26 | 18 | 12 | **93** | **93** | 88 | 15 | 11 | 42 |
| LP1F | 2 | 2 | 2 | 3 | 5 | 3 | 2 | 2 | 5 |

FIG. 22

Original Selection Template (LP3):

CTA TGA ACT GAC QTrATF GAC CTC ACT ACC AAG - CAA GCA TGG ACA ATA CCG AGC N40 ATC TTG TCA TCG GAG GCT TAG

Best Sequence (R11-R2):

CTA TGA ACT GAC QTrATF GAC CTC ACT ACC AAG - CAA GCA TGG ACA ATA CCG AGC – CTT TCA TTT CAG CCG ATC ATA CCT CAA TGT AGA TAA GCA C – ATC TTG TCA TCG GAG G – CTT AG

Reselection Template (LP3Z1):

CTA TGA ACT GAC QTrATF GAC CTC ACT ACC AAG – CAA GCA TGG ACA ATA CCG AGC – CTT TCA TTT CAG CCG ATC ATA CCT CAA TGT AGA TAA GCA C – ATC TTG TCA TCG GAG G – CTT AGT AGC CGA AGT TGC TGA

| Rank | Copy | Sequence | R4 | R9 | Trend |
|---|---|---|---|---|---|
| 1 | 7542 | CGGTCATTTCAGCGGGTACTTCCTCAAAGAAGAAAAGCACATCTTTTCCGCGGATC | 0.0143% | 10.3946% | |
| 2 | 2246 | CCTTCATTTCAGCGGAGCATACCACACGGTAGACAAGCACATCTTGTCCCGGGGCG | 0.0098% | 3.0955% | |
| 3 | 1613 | CCTTCATTTCAGACGATGATACCTCAATTTAGTTAAGCACATCTTATCGTGGGCGC | 0.0045% | 2.2231% | |
| 4 | 1113 | CCTTCATTTCAGCTGATCATACCGCAATAGCGGAAAGCACATCTTTTCAGGGGATC | 0.0034% | 1.5340% | |
| 5 | 1046 | ACTTCATTTCAGCTGATCAATCCATATTGTAGATGAGCACTTCTCGTCATCTGGTG | 0.0063% | 1.4416% | |
| 6 | 811 | CCTTCATTTCAGACGATCTTCTCTCAGTCAAGATAGGCACATCCTGTCATCGGGGG | 0.0016% | 1.1177% | |
| 7 | 467 | ACTTCATTTCAGCCGTTCACGACCGACAGTGGATAAGCACATCTTATCACGGGTGC | 0.0063% | 0.6436% | |
| 8 | 466 | ATTTCATTTCAGCCGATGTTACCTTACTGGAAATAGCCACCCCTGTTTATCGGATG | 0.0001% | 0.6423% | |
| 9 | 392 | CCTTCATTTCAGCTGATCGTACCTCGATTTAGGCAAGCACATCTTGTCAGGGGCGA | 0.0044% | 0.5403% | |
| 10 | 391 | CGTTCATTTCAGCCGATCCTACCTCCATGGAGGCAAGCACATCTTGTCGGCGGATC | 0.0053% | 0.5389% | |

| DNAzyme | $Y_{max}$ (%) | $K_{obs}$ ($min^{-1}$) |
|---|---|---|
| LP3Z1 R9R4 F5' | 95 ± 1 | 0.054 ± 0.002 |
| LP1F5' | 99 ± 2 | 0.040 ± 0.002 |

FIG. 26A
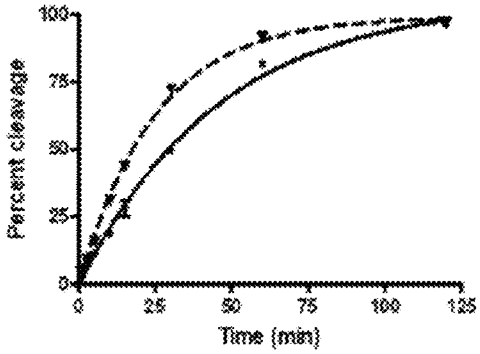
FIG. 26B
| DNAzyme | $Y_{max}$ (%) | $K_{obs}$ ($min^{-1}$) |
|---|---|---|
| MET10 | 100 ± 4 | 0.022 ± 0.002 |
| LP1F5' | 99 ± 2 | 0.040 ± 0.002 |
FIG. 26C
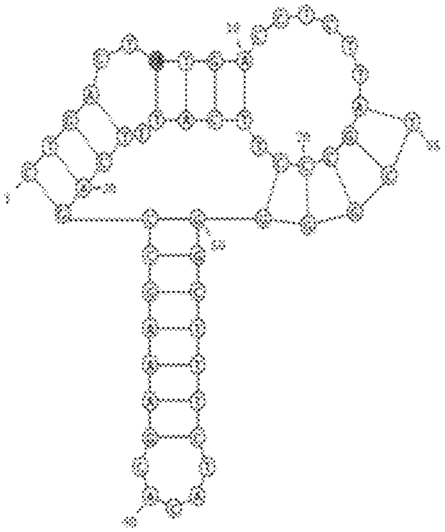
FIG. 26D
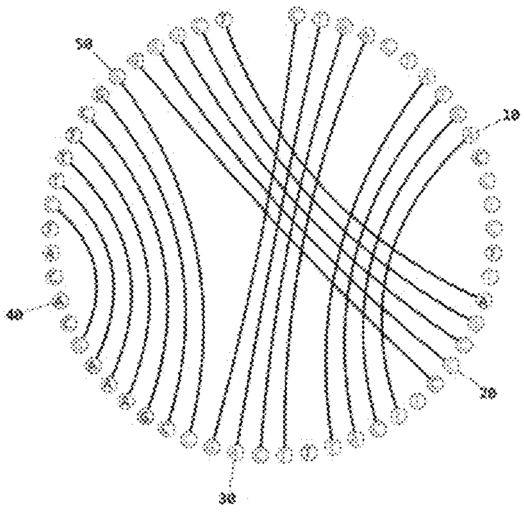

LP1: CTTTCATTTCAGCCGATCATACCTCAATGTAGATAAGCACATCTTGTCATCGGAGGCTTAG

FIG. 30

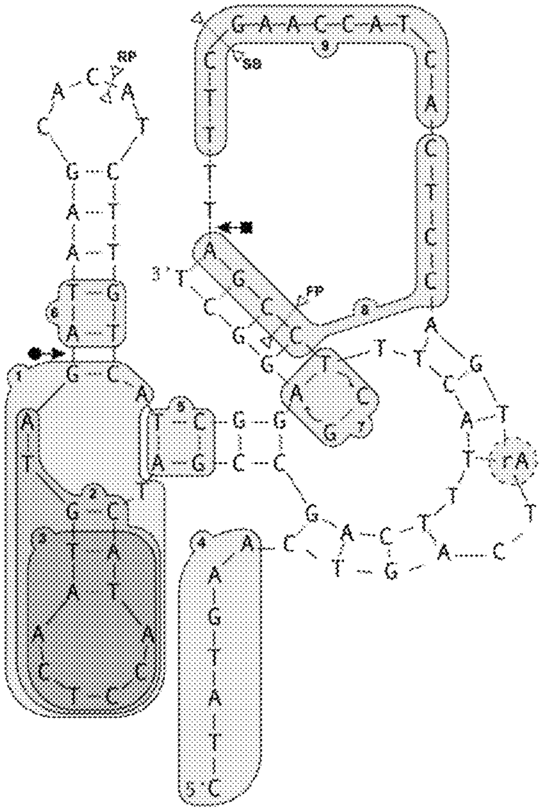

| Name | Truncations | Length |
|---|---|---|
| MET1 | ④⑨ | 77 |
| MET2 | ④⑨② | 63 |
| MET3 | ④⑨⑧⑦ | 55 |
| MET4 | ④⑨①⑥ | 55 |
| MET5 | ④⑨③ | 67 |
| MET6 | Same as MET4 but with insertion of 4T at ◄-■ | 59 |
| MET7 | Same as 4TFP but with insertion of 2T at ◄-■ | 101 |
| MET8 | Same as MET4 but with 5'-TA-3' insertion at ●-► | 57 |
| MET9 | Same as MET8 but with insertion of 4T at ◄-■ | 61 |
| MET10 | ④⑨①⑥⑦ | 55 |
| MET11 | Same as MET10 but with insertion of 5'-CTA-3' at ◄-■ and 5'-TAG-3' at the 3'-terminal | 61 |
| MET12 | ④⑨①⑥⑦⑤ | 51 |
| MET13 | Same as MET10 but with insertion of 4T at ◄-■ | 59 |

DNAZYMES FOR DETECTING *LEGIONELLA PNEUMOPHILA*

RELATED APPLICATION

This disclosure claims benefit of U.S. Provisional Patent Application Ser. No. 63/166,553 filed Mar. 26, 2021, incorporated herein by reference in its entirety.

INCORPORATION OF SEQUENCE LISTING

A computer readable form of the Sequence Listing "P66448US01_ST25_Revised_SL" (48,623 bytes), amended on May 31, 2022 and submitted via EFS-WEB, is hereby incorporated by reference.

FIELD

The present disclosure relates to DNAzymes or biosensors for detecting pathogenic bacteria, and in particular, for detecting *Legionella pneumophila*.

BACKGROUND

Ineffective bacterial monitoring in water systems represents a danger to public health and can result in costly disease outbreaks. Of interest is *Legionella pneumophila*, a deadly waterborne bacterial pathogen from naturally occurring and man-made water sources, that causes Legionnaires' disease, a severe form of pneumonia.[1] Inhalation of droplets containing *Legionella pneumophila* is thought to be the primary mode of disease transmission. Once inhaled, *Legionella pneumophila* cells multiply intracellularly in human macrophages by avoiding phagosome-lysosome fusion. [2-5] The first official report of a Legionnaires' disease outbreak (attributed to a contaminated cooling tower) took place in July of 1976 at the annual American Legion convention in Philadelphia where 34 of 221 cases were fatal.[6] In contrast to the 1976 incident where the causative agent behind the disease was unknown, the role of *Legionella pneumophila* in causing Legionnaires' disease is now well understood. Despite this knowledge and the implementation of prevention measures, Legionnaires' disease outbreaks continue to arise, impacting many lives around the world. The Centers for Disease Control and Prevention has stated that reported cases of Legionnaires' disease in the United States have quadrupled since 2000, and ranks *Legionella* as the number one cause of waterborne disease outbreaks in the country. [7-9] Furthermore, there are challenges in specifically detecting *Legionella*, and this is further confounded by a lack of appropriate diagnostic testing and monitoring methods available as reported by the World Health Organization.[10] The COVID-19 pandemic has further demonstrated the need for rapid, accurate, and highly sensitive detection of *Legionella pneumophila* in exposure sources as highlighted in the media with numerous buildings reporting contamination. Buildings that remain empty for prolonged periods of time favor the development of stagnant water, an ideal growing condition for *Legionella* to proliferate.[11] Additionally, the clinical manifestation of legionellosis can mimic symptoms associated with COVID-19, as illustrated by a case study reported in Italy following reopening measures.[11]

There exists a great need for the development of field-appropriate assays that can provide early-stage detection of

*Legionella pneumophila* in water as a means of mitigating Legionnaires' disease outbreaks.

SUMMARY

The present disclosure describes an RNA cleaving DNAzyme, LP1, derived by in vitro selection, that demonstrates highly selective RNA-cleaving activity towards *Legionella pneumophila* without manipulation of the samples. LP1 is activated by a protein biomarker of *Legionella pneumophila*, capable of generating a detectable signal in the presence of as few as 10 colony forming units of *Legionella pneumophila*, a level of sensitivity not previously demonstrated with DNAzymes for other bacteria. It also represents the best detection sensitivity among all the methods for *Legionella pneumophila* without a culturing or signal amplification step. LP1 activity is maintained in cooling tower water from diverse sources without any manipulation of the samples, is reactive with multiple infectious isolates of *Legionella pneumophila* but inactive with 25 other common bacterial species.

Accordingly, the present disclosure provides a DNAzyme for detecting *Legionella pneumophila* comprising or consisting of a sequence selected from the group consisting of SEQ ID NOS: 7-71, 187, and 188, or a functional fragment or modified derivative thereof. In some embodiments, the DNAzyme comprises or consists of a sequence selected from the group consisting of SEQ ID NOS: 7-14, 20-24, 30-36, 45, 48, 54-60, 69, 187, and 188. In some embodiments, the DNAzyme comprises or consists of the sequence of SEQ ID NO: 34 or 58. In some embodiments, the DNAzyme comprises a detectable label. In some embodiments, the detectable label comprises a fluorescent, a colorimetric, or other optical or electrochemical moiety. In some embodiments, the fluorescent moiety is a fluorophore. In some embodiments, the fluorophore is fluorescein.

Also provided is a biosensor for detecting *Legionella pneumophila* comprising the DNAzyme described herein. In some embodiments, the biosensor comprises a support. In some embodiments, the support comprises cellulose or paper.

Also provided is a kit for detecting *Legionella pneumophila*, wherein the kit comprises the DNAzyme or biosensor described herein and instructions for use of the kit. In some embodiments, the kit further comprises one or more of: i) a buffer, ii) an RNase inhibitor, and iii) a metal ion.

Also provided is a method for detecting the presence of *Legionella pneumophila* in a test sample, comprising:

a) contacting said test sample with the DNAzyme or biosensor described herein, wherein the DNAzyme comprises a detectable label;

b) allowing cleavage of the DNAzyme if a target is present, thereby releasing the detectable label; and c) measuring a detectable signal if the portion of the DNAzyme comprising the detectable label is released, wherein the RNA cleavage activity of the DNAzyme is activated by a target from *Legionella pneumophila*.

In some embodiments, the target is a protein target. In some embodiments, the protein target is a protein target of 30-100 kDa. In some embodiments, the DNAzyme detects at least 10 colony forming units of *Legionella pneumophila*.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

BRIEF DESCRIPTION OF THE DRAWINGS

The embodiments of the disclosure will now be described in greater detail with reference to the attached drawings in which:

FIG. 1A shows the selection approach in an exemplary embodiment of the disclosure. FIG. 1A shows the library construct for the selection of *Legionella pneumophila* responsive DNAzymes. Starting from the 5' end, the construct comprises an RNA-containing substrate sequence of 30 nucleotides (nt) (SEQ ID NO: 2), a forward primer of 21 nt (SED ID NO: 4), a random domain of 40 nt, and a reverse primer of 21 nt (SEQ ID NO: 5).

FIG. 1B shows the selection approach in an exemplary embodiment of the disclosure. FIG. 1B shows the sequence of the random domain of the DNAzyme LP1 (SEQ ID NO: 72).

FIG. 1C shows the selection approach in an exemplary embodiment of the disclosure. FIG. 1C shows representative schematics of different versions of LP1. R: adenosine ribonucleotide; F: fluorescein-dT; Q: DABCYL-dT. LP1FQ, LP1F3' and LP1F5' have the same sequence but differ in F and Q modifications.

FIG. 2A shows kinetic profile of the cleavage reaction of LP1FQ. Lp=*Legionella pneumophila*. FP: the fluorophore-containing cleavage product. QP: the quencher-containing cleavage product. The percent cleavage of LP1FQ (0.1 μM) after 1-720 min incubation with crude extracellular mixture of *Legionella pneumophila* (CEM-LP) ($10^6$ CFU) at room temperature was fit using the equation $Y=Y_{max}[1-e^{-kt}]$ with Prism (GraphPad, 4.03). Three trials were performed. The observed rate constant ($k_{obs}$) and maximum cleavage yield ($Y_{max}$) are given in the graph.

FIG. 2B shows selectivity of LP1FQ. The RNA-cleaving activity of LP1FQ in the presence of crude extracellular mixture (CEM) from 26 different bacteria was determined by dPAGE. M1 and M2 comprise the full-length LP1FQ and FP, respectively. The Clv % refers to the cleavage percentage observed under this set of conditions, and is shown under the graphs. Where no cleavage was observed a line is shown. Bacteria on the top: *Ochrobactrum grignonense* (O.g), *Brevundimonas diminuta* (B.d), *Achromobacter xylosoxidans* (A.x), *Fusobacterium nucleatum* (F.n), *Streptococcus* sahvarius (S.s), *Enterococcus faecium* (E.f), *Listeria monocytogenes* (L.m), *Bacillus subtilis* (B.s), *Veillonella parvula* (V.p), *Clostridium difficile* (C.d), *Bacteroid fragilis* (B.f), *Actinomyces orientalis* (A.o). Bacteria on the bottom: *Klebsiella aerogenes* (K.a), *Klebsiella pneumoniae* (K.p), *Enterobacter aerogenes* (E.a), *Enterobacter cloacae* (E.c), *Salmonella enterica* (S.e), *Escherichia coli* k12 (E.ck), *Shigella sonnei* (S.s), *Shigella flexneri* (S.f), *Yersinia ruckeri* (Y.r), Hafnia *alvei* (H.a), *Serratia fonticola* (S.f.), *Acinetobacter lwoffii* (A.l), *Pseudomonas aeruginosa* (P.a), *Legionella pneumophila* (L.p). Reaction time: 1 h. The dash left to the gel indicates the location of the uncleaved LP1FG (top) and the cleaved fragment FP (bottom) within the gel.

FIG. 3A shows removal of F and Q enhances LP1 activity towards *Legionella pneumophila*. The percent cleavage of LP1P, LP1F3' and LP1F5' upon incubation with crude extracellular mixture of *Legionella pneumophila* (CEM-LP) at room temperature for 1-90 min was fit using the equation $Y=Y_{max}$ $[1-e^{-kt}]$ with Prism (GraphPad, 4.03). Three trials were performed. The observed rate constants ($k_{obs}$) and maximum cleavage yields ($Y_{max}$) are reported in the table.

FIG. 3B shows removal of F and Q reduces the specificity of LP1F3'. The RNA-cleaving activity of LP1F3' in response to various species of bacteria was determined by dPAGE. Lp=*Legionella pneumophila*. Incubation time: 1 h. See brief description of FIG. 2B for full bacteria names. The dash left to the gel indicates the location of the uncleaved LP1F3' (top) and the cleaved fragment F3'P (bottom) within the gel.

FIG. 3C shows addition of RNase inhibitor (the SUPERase-In RNase inhibitor) improves specificity of LP1F3'. The RNA-cleaving activity of LP1F3' in the presence of the RNase inhibitor towards species capable of inducing non-specific cleavage was determined by gel electrophoresis. Marker (M) lanes comprise the full-length LP1F3' (M1) and the fluorophore-carrying cleavage product F3'P (M2). Other lanes were reactions with the crude extracellular mixture (CEM) of a given bacterium. Incubation time: 1 h. See brief description of FIG. 2B for full bacteria names. The dash left to the gel indicates the location of the uncleaved LP1F3' (top) and the cleaved fragment F3'P (bottom) within the gel.

FIG. 4A shows cleavage reaction of LP1F5' which was used in this experiment. Lp=*Legionella pneumophila.*

FIG. 4B shows the activity of LP1F5' in the presence of four different *Legionella* species, determined by dPAGE. The marker lane (M) comprises the full-length LP1F5'. Lanes 1-8: *Legionella micdadei* (Lm), *Legionella dumofii* (Ld), *Legionella pneumophila* (Lp), and *Legionella longbeachae* (Ll), tested in duplicate. Incubation time: 1 h.

FIG. 4C shows the activity of LP1F5' in the presence of five *Legionella pneumophila* strains, determined by dPAGE. The marker lane (M) comprises the full-length DNAzyme LP1F5' and the fluorophore-carrying cleavage product 5'FP. Lanes 1-12: *Legionella pneumophila* strains Toronto-2005, Lens, 130b, Paris, and Philadelphia. All strains tested in duplicate. Incubation time: 1 h. The dash left to the gel in panels B and C indicates the location of the uncleaved LP1F5' (top) and the cleaved fragment 5'FP (bottom) within the gel.

FIG. 6A shows cleavage reaction of LP1F5' which was used for this experiment.

FIG. 6B shows estimation of target size by successive molecular weight exclusion filtration. The same crude extracellular mixture of *Legionella pneumophila* (CEM-LP) sample as in FIG. 6A was passed sequentially through molecular weight cut off filters of various sizes ranging from 300 kDa to 3 kDa in size. The filtrate (F) and concentrate (C) were collected and the cleavage activity of each was assessed by dPAGE after a 1 h incubation period with LP1F5', at room temperature.

FIG. 6C shows the activity of LP1F5' incubated with CEM-LP treated with Proteinase K was determined. Crude extracellular mixture of *Legionella pneumophila* (CEM-LP) was incubated with (+PK) and without Proteinase K (−PK) at 37° C. overnight, followed by incubation with LP1F5'. Ctl: controls with CEM-LP incubated without Proteinase K at room temperature overnight, followed by incubation with LP1F5'. The reaction mixtures were then analyzed by dPAGE. Incubation time with LP1F5' was 1 h. The marker lane (M) comprises the full-length DNAzyme LP1F5' and the fluorophore-carrying cleavage product 5'FP. The dash left to the gel in panels B and C indicates the location of the uncleaved LP1F5' (top) and the cleaved fragment 5'FP (bottom) within the gel.

FIG. 7A shows LP1 maintains its activity in cooling tower water in an exemplary embodiment of the disclosure. FIG. 7A shows cleavage reaction of LP1F5' which was used for this experiment.

FIG. 7B shows LP1 maintains its activity in cooling tower water in an exemplary embodiment of the disclosure. FIG. 7B shows locations and number of cooling tower water samples collected from Canada and the United States. The average percent cleavage activity of LP1F5' incubated for 1 h with cooling tower water spiked with crude extracellular mixture of *Legionella pneumophila* (CEM-LP) for each location is presented. The standard deviation (SD) for samples collected from Quebec and Pennsylvania is also shown. LP1F5' cleavage was determined by dPAGE. For each water sample, two tests were conducted.

FIG. 7C shows LP1 maintains its activity in cooling tower water in an exemplary embodiment of the disclosure. FIG. 7C shows a representative gel image of the cleavage reaction of LP1F5' after incubation for 1 h with either the cooling tower water spiked with crude extracellular mixture of *Legionella pneumophila* (CEM-LP) (+L.p) or cooling tower water alone (−L.p) as shown. The dash left to the gel in panels B and C indicates the location of the uncleaved LP1F5' (top) and the cleaved fragment 5'FP (bottom) within the gel.

Unported License and copyrighted in 2016 by Nature America, Inc. [13] Species investigated in this work include: *Legionella pneumophila, Legionella micdadei, Legionella dumofii*, and *Legionella longbeachae*.

Figure 15:
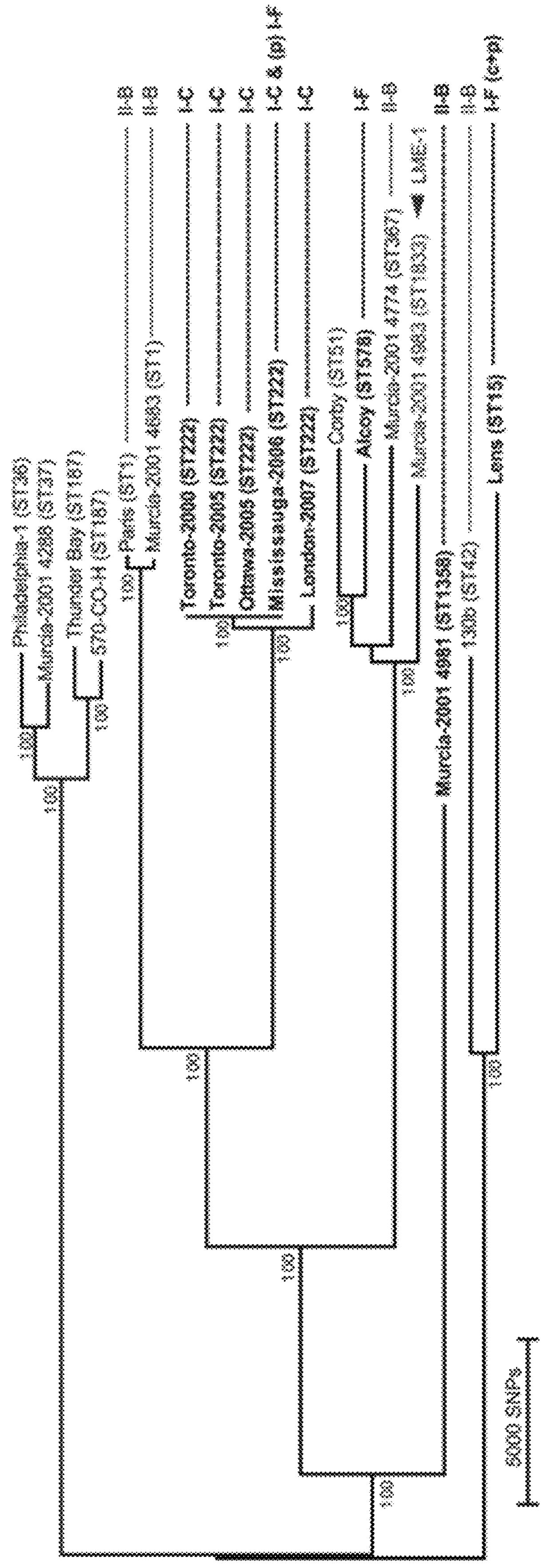

FIG. 15 shows the phylogenetic tree of *Legionella* strains in an exemplary embodiment of the disclosure. Reproduced from Rao, C., Guyard, C., Pelaz, C., Wasserscheid, J., Bondy-Denomy, J., Dewar, K., and Ensminger, A. W. Active and adaptive *Legionella* CRISPR-Cas reveals a recurrent challenge to the pathogen. *Cellular Microbiology* 18(10) 1319-1338 (2016) which was under a Creative Commons Attribution License and copyrighted in 2016 by Rao, C., Guyard, C., Pelaz, C., Wasserscheid, J., Bondy-Denomy, J., Dewar, K., and Ensminger, A. W. in Cellular Microbiology Published by John Wiley & Sons Ltd. [14]

Figure 16:
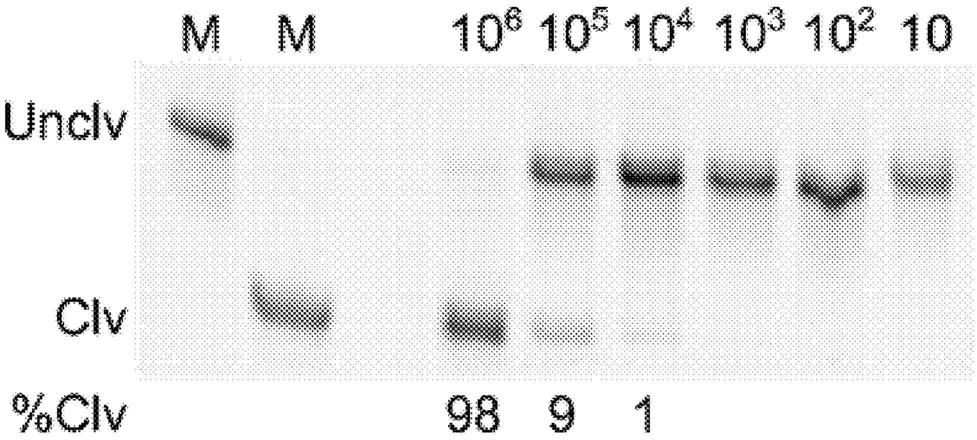

FIG. 16 shows the DNAzyme LP1F3' can detect as low as $10^4$ cfu after a 1 hour incubation in an exemplary embodiment of the disclosure. LP1F3' was incubated with the crude extracellular mixture (CEM) prepared from $10^6$ cfu-10 cfu of *Legionella pneumophila* in 1 mL for 1 hour at room temperature. RNA-cleaving activity was determined by gel electrophoresis. Lanes 1-2: marker (M) showing full length LP1F3' and cleaved LP1F3', respectively. Unclv and Clv denote un-cleaved LP1F3' and cleaved LP1F3'.

Figure 17:
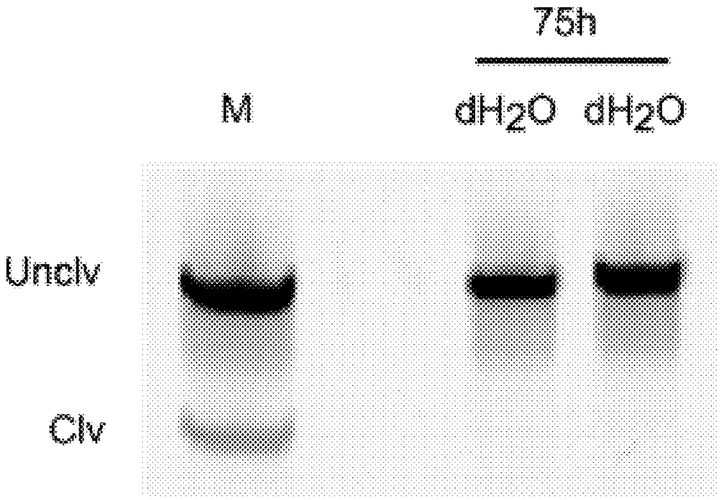

FIG. 17 shows DNAzyme stable at room temperature over extended time period in an exemplary embodiment of the disclosure. LP1F3' was incubated with selection buffer (containing deionized water rather than crude extracellular mixture of *Legionella pneumophila* (CEM-LP)) at room temperature over a period of 75 hours and RNA-cleaving activity was determined by gel electrophoresis. No significant cleavage band was observed. Unclv and Clv denote un-cleaved DNAzyme and cleaved DNAzyme.

Figure 18A:
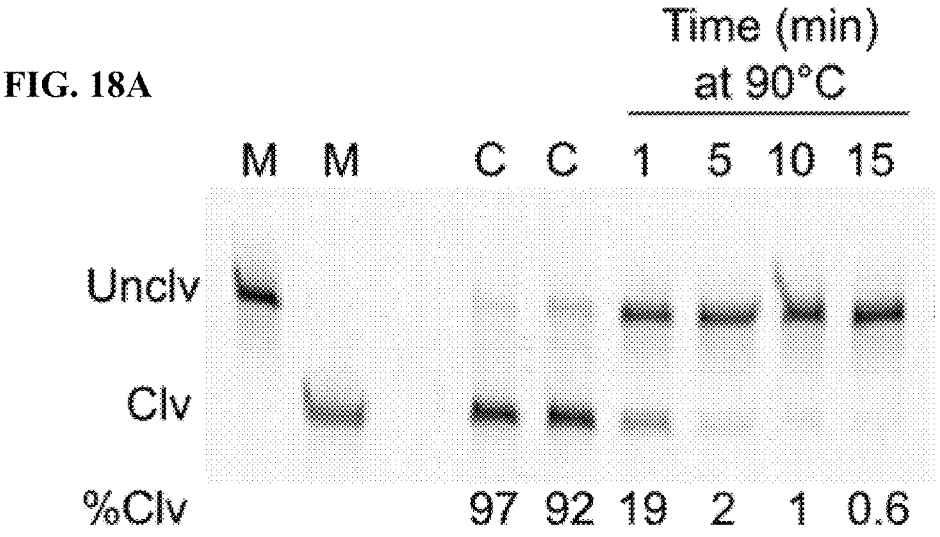

FIG. 18A shows the results of heating the crude extracellular mixture of *Legionella pneumophila* (CEM-LP) in exemplary embodiments of the disclosure. FIG. 18A shows heating CEM-LP results in decreased LP1F3' cleavage activity. CEM-LP was heated at 90° C. for various timepoints (1-15 min) and then the RNA-cleaving activity of LP1F3' in each heated CEM-LP timepoint was determined using dPAGE (lanes 5-8). Lanes 1-2: marker (M) showing full length LP1F3' and cleaved LP1F3', respectively. Lanes 3-4: control (C) demonstrating RNA-cleaving activity of LP1F3' in the presence of unheated CEM-LP. Unclv and Clv denote un-cleaved LP1 and cleaved LP1. Incubation time with LP1F3': 1 hour.

Figure 18B:
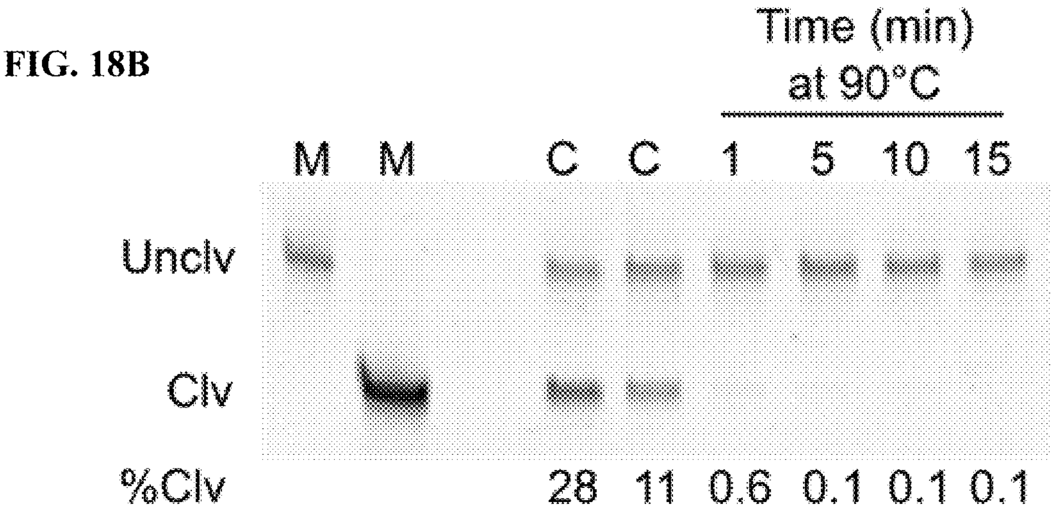

FIG. 18B shows the results of heating the crude extracellular mixture of *Legionella pneumophila* (CEM-LP) in exemplary embodiments of the disclosure. FIG. 18B shows heating CEM-LP results in decreased LP1FQ cleavage activity. The same investigation done in (A) was conducted for LP1FQ.

Figure 19:
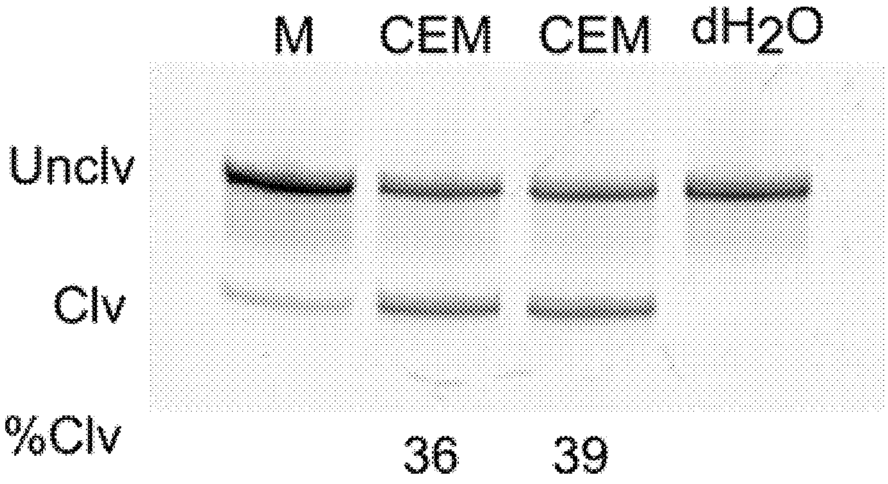

FIG. 19 shows the LP1F3' DNAzyme maintains its cleavage activity in the absence of selection buffer in an exemplary embodiment of the disclosure. As an investigation into the metal ion dependency of the DNAzyme, the RNA-cleaving activity of LP1F3' was assessed in the absence of selection buffer (SB). Lanes 1-4: marker (M) showing full length and cleaved LP1F3', cleavage of LP1F3' in CEM-LP (CEM) (no SB) in duplicate, cleavage of LP1F3' in water (no SB or CEM-LP) as a control ($dH_2O$). Unclv and Clv denote uncleaved DNAzyme and cleaved DNAzyme. Incubation time: 1 hour.

Figure 20A:
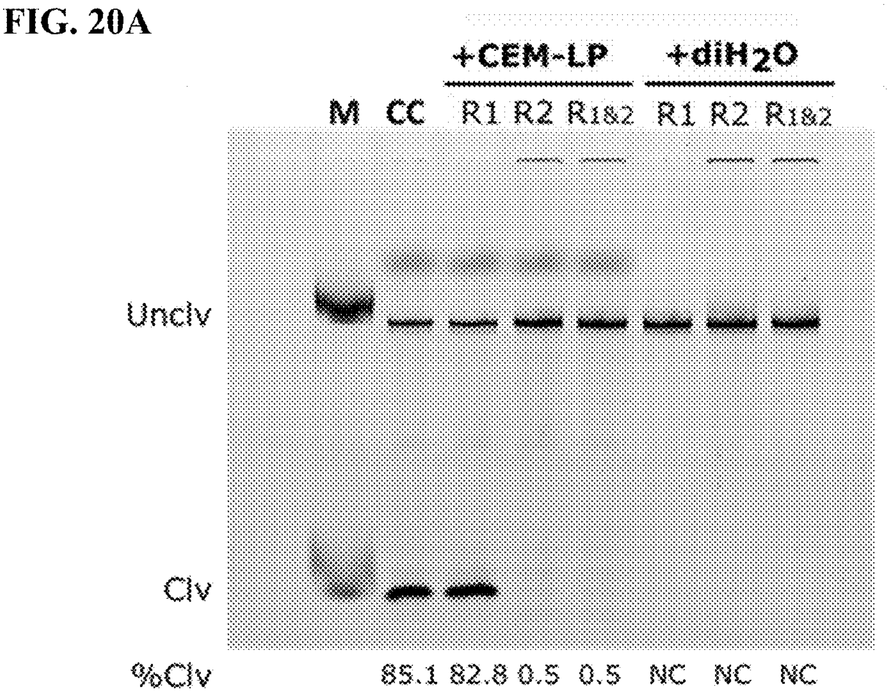

FIG. 20A shows the evaluation of DNAzyme stability in the presence of water treatment reagents obtained from TGWT Clean Technologies Inc. in an exemplary embodiment of the disclosure. The proprietary reagents manage the pH of the recirculating cooling tower water systems (reagent 1: R1) and remove organic deposits and biofilms from water system surfaces (reagent 2: R2). FIG. 20A shows the stability (+$diH_2O$) and cleavage (+CEM-LP) of LP1F5' was assessed in the presence of each reagent at the upper maintenance level. Firstly, the DNAzyme was stable in the presence of the reagents either individually (R1 or R2) or combined (R1&2), and deionized water ($diH_2O$) rather than crude extracellular mixture of *Legionella pneumophila* (CEM-LP). Secondly, when the samples were spiked with CEM-LP, cleavage was observed in the presence of R1 (at 236 ppm) which was comparable to the cleavage control (no reagents). No cleavage was observed in the presence of R2 (at 4000 ppm), likely because the reagent had degraded the bacterial target. Cleavage values shown on the image are from three replicates. The values with standard deviations were as follows: 85.1±7.2 (CC), 82.8±10.3 (R1+CEM-LP), 0.5±0.1 (R2+CEM-LP), and 0.5±0.1 (R1&R2+CEM-LP). Abbreviations: autoclaved and Rnase free deionized water ($diH_2O$), LP1F5' cleavage induced by NaOH in the absence of reagents or CEM-LP for size markers (M), LP1F5' cleavage induced by CEM-LP in a typical (no reagents) cleavage reaction (CC), uncleaved LP1F5' band (Unclv), cleavage product of Lp1F5' band (Clv), percent cleavage (% Clv), and no cleavage observed (NC).

Figure 20B:
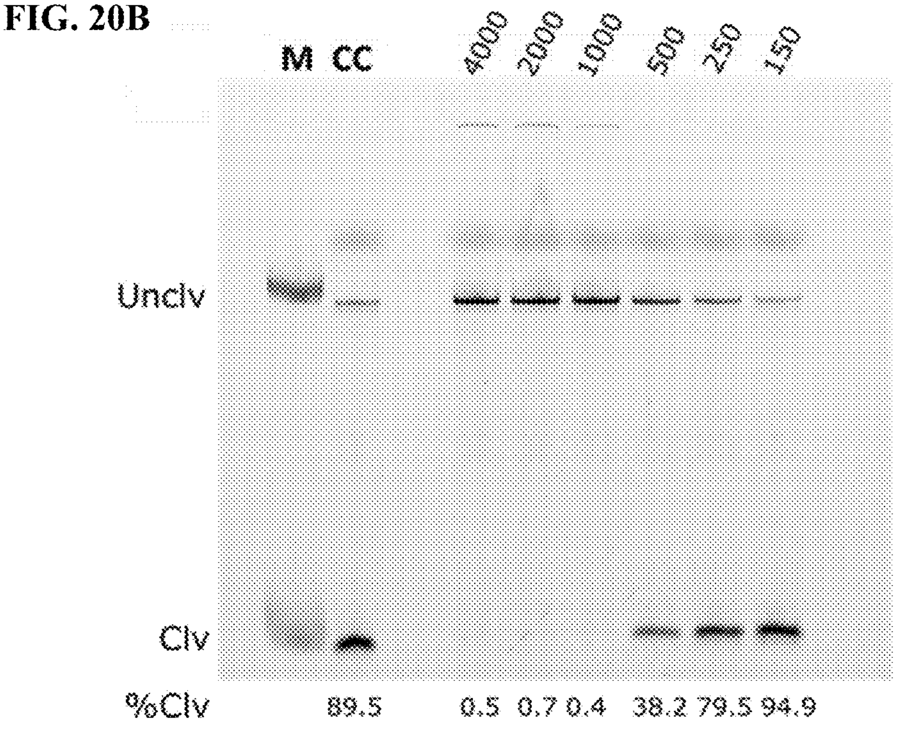

FIG. 20B shows the evaluation of DNAzyme stability in the presence of water treatment reagents obtained from TGWT Clean Technologies Inc. in an exemplary embodiment of the disclosure. FIG. 20B shows assessment of concentration dependent inhibitory effect of R2 on LP1F5' cleavage in the presence of crude extracellular mixture of *Legionella pneumophila* (CEM-LP). It is likely that at the highest level of R2 (evaluated in FIG. 20A), the target is destroyed by the reagent. Since the eventual disclosure of LP1F5' would likely be in cooling tower water before treatment, the activity of LP1F5' was assessed in the presence of R2 and CEM-LP at maintenance levels (150 and 250 ppm), and levels used to treat moderate (500 and 1000 ppm) to severe (2000 and 4000 ppm) biofouling. The average percent cleavage values calculated from duplicates, for LP1F5' in the presence of CEM-LP and various R2 concentrations are shown. The % values with standard deviations were: 89.5±3.2 (CC), 0.5±0.1 (4000 ppm), 0.7±0.3 (2000 ppm), 0.4±0.2 (1000 ppm), 38.2±7.0 (500 ppm), 79.5±1.2 (250 ppm), 94.9±0.8 (150 ppm). These data show that the LP1F5' is functional at maintenance levels of R2, which is most relevant for initial on-site testing. Abbreviations are the same as for panel A. Experimental notes: Briefly, LP1F5' was combined with buffer and the treatment reagents, and then heated to 90° C. for 30 sec. Either CEM-LP or deionized water ($diH_2O$) was added to each reaction and they were incubated at room temperature for 1 hour. Cleavage was assessed by dPAGE.

Figure 21:
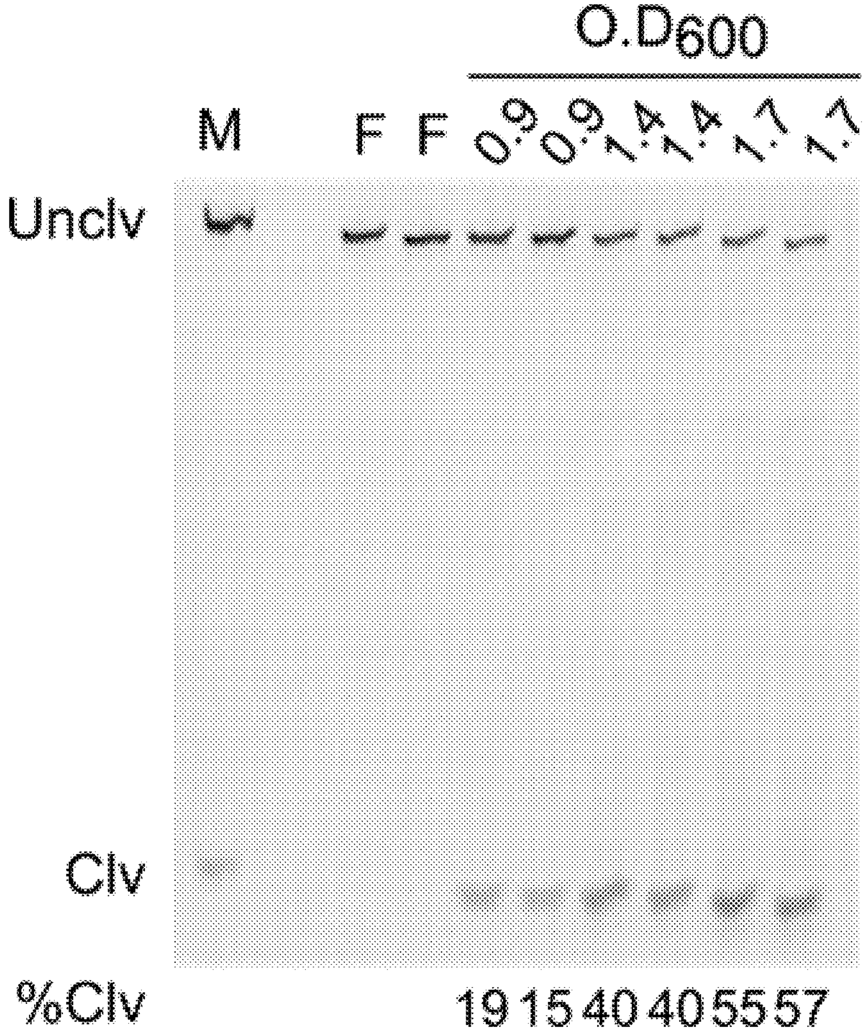

FIG. 21 shows DNAzyme maintains its RNA-cleaving activity in Fraquil in an exemplary embodiment of the disclosure. Fraquil is a defined freshwater medium in which *Legionella pneumophila* can remain culturable for an extended period. The Fraquil was prepared as previously described [15]. Briefly, *Legionella pneumophila* was cultured as described in methods but after inoculation was grown to post exponential phase (24 hr). The culture was spun down and rinsed twice with Fraquil. The bacteria were then resuspended in Fraquil at O.D600~1-2 and incubated at room temperature for 24 hours. After incubation, the RNA-cleaving activity of LP1F5' at each O.D600 was determined as previously described for cleavage reactions. Lanes 1-3: marker (M) showing full length LP1F5' and cleaved LP1F5' sequence, Fraquil (F) incubated with LP1F5' (no *Legionella pneumophila*) as control. Lanes 4-9: O.D600 of *Legionella pneumophila* resuspension in Fraquil. Unclv and Clv denote un-cleaved DNAzyme and cleaved DNAzyme. Incubation time with LP1F5': 1 hour. The decreased cleavage activity here is likely due to the fact that the subculture, rather than the crude extracellular mixture (CEM) was used in this assessment. It could also be that the bacteria exude less target under these conditions than in BYE. The Fraquil media is not enriched, and therefore lacks the nutrients that would be present in BYE or a cooling tower environment.

FIG. 22 shows the original selection (LP3) template (SEQ ID NO: 73), the best sequence candidate from the original selection (R11-R2 (SEQ ID NO: 74)), and the reselection (LP3Z1; SEQ ID NO: 75) template in an exemplary embodiment of the disclosure. The quencher (dT-Q, shown as QT) and fluorophore (dT-F, shown as TF) modifications of the substrate are shown. The cleavage site of the substrate is indicated by rA. The original library contained a 40-nt random region, whereas the reselection library was extended by 16 nt into the original primer region and mutagenized at 30% per nucleotide based of the R11-R2 sequence. In the original template sequence, a dash is used to separate the sub state and catalytic domains. For R11-R2, the first dash separates the substrate and catalytic regions, the second and third dashes indicate the random region, and the third and fourth dashes show the 16 nucleotides of the primer that are mutated in the reselection template. The CTTAG (underlined) sequence was suspected to be important in the secondary structure of R11-R2 and was kept constant. For the reselection template, the first dash separates the substrate and catalytic region, the 40 nucleotide random region is contained between the first and second dashes, and the 16 additional nucleotide extension of the random region is shown between the third and fourth dashes. The top 10 ranked sequences by abundance are shown in the summary table (SEQ ID NO: 76-85), along with their abundance in rounds 4 and 9, and their enrichment trend overall.

Figure 23A:
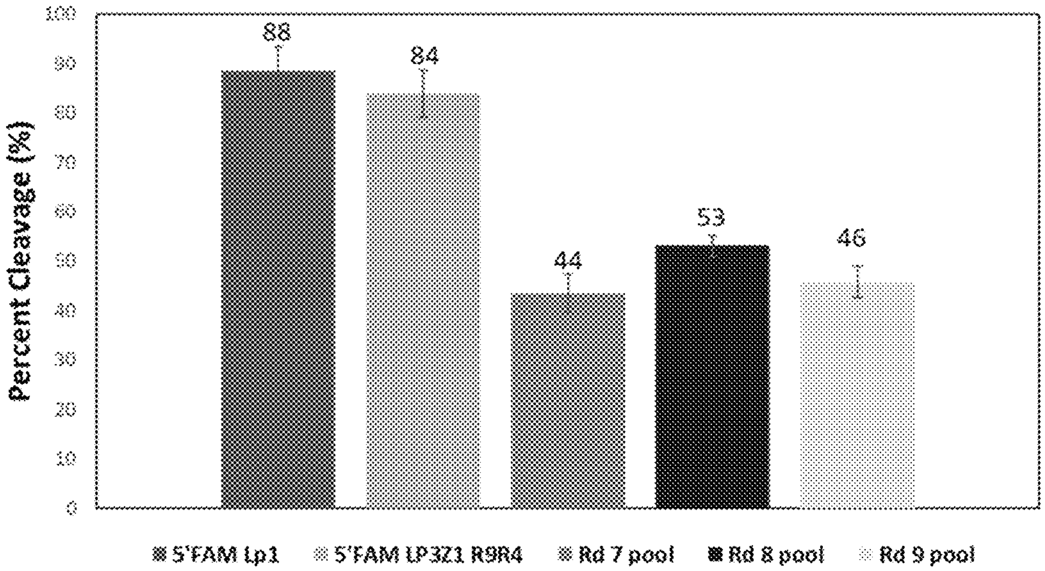

FIG. 23A shows summary of % cleavage after a 1 hr incubation with crude extracellular mixture of *Legionella pneumophila* (CEM-LP) of the LP1F5' control compared to the best preforming sequence from the reselection (LP3Z1 R9R4 F5' or Rank 4 in the main text), and the combined library from round (Rd) 7, 8 and 9.

Figure 23B:
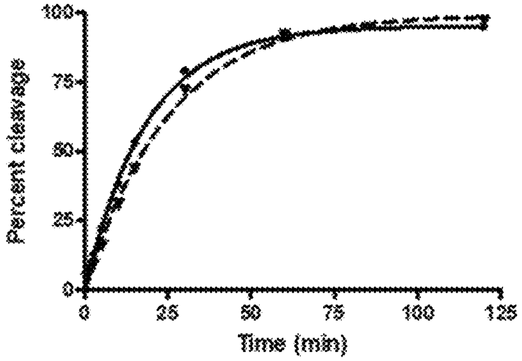

FIG. 23B shows kinetic analysis of LP3Z1 R9R4 F5' compared to LP1F5' in the presence of crude extracellular mixture of *Legionella pneumophila* (CEM-LP) for various time points ranging from 0.5 min to 120 min was assessed using the 5'-FAM modified substrate (lacking the F&Q modifications flanking the ribonucleotide site that was originally used in the selection). Kinetic activity of LP3Z1 R9R4 F5' from the reselection and LP1F5' from the original selection is comparable. The percent cleavage of LP3Z1 R9R4 F5' and LP1F5' upon incubation with CEM-LP at room temperature for 1-120 min was fit using the equation $Y=Y_{max}$ $[1-e^{-kt}]$ with Prism (GraphPad, 4.03). Three trials were performed. The observed rate constants ($k_{obs}$) and maximum cleavage yields ($Y_{max}$) are reported in the table in exemplary embodiments of the disclosure.

Figure 24:
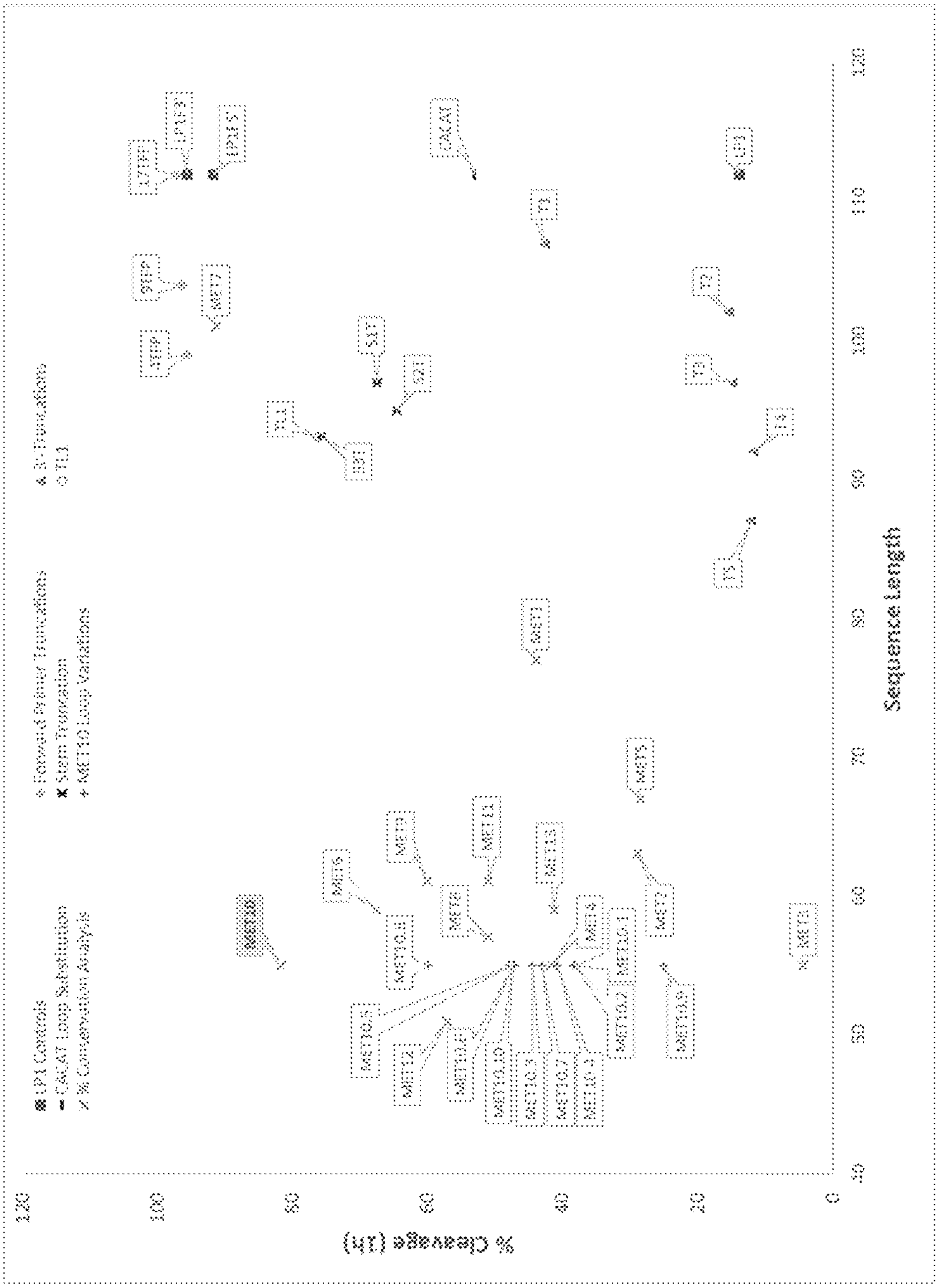

FIG. 24 shows comparison of sequence length by % cleavage after 1 h incubation with crude extracellular mixture of *Legionella pneumophila* (CEM-LP) of each truncated sequence in an exemplary embodiment of the disclosure. Truncation classes are coded with symbols, and the truncation name is stated in proximity to the respective datapoint. The most successful truncation was MET10, which is denoted by the grey label, as it was the shortest sequence with the highest activity.

Figure 25:
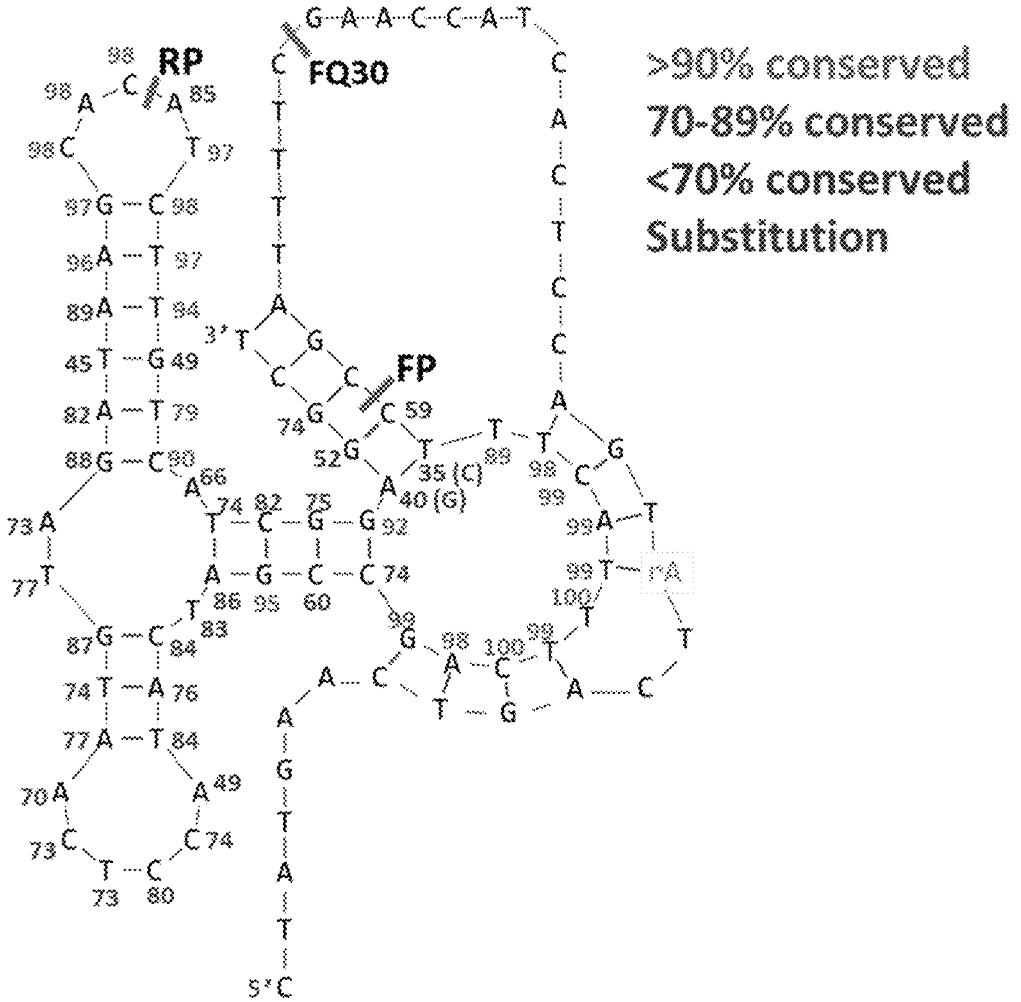

FIG. 25 shows percent conservation of mutagenized nucleotide positions mapped onto the predicted secondary structure of the 4TFP truncation with three non-bound 3'-terminal nucleotides (5'-TAG-3') removed (SEQ ID NO: 187; SEQ ID NO: 188) in an exemplary embodiment of the disclosure. Percent conservation was determined using the top 500 sequences from round 9 of the reselection. Given the mutation rate of the reselection library (30%), nucleotide positions that were conserved at greater than 90% were considered highly conserved and essential, whereas nucleotide positions that were conserved at less than 70% were considered to be either non-essential or disadvantageous.

FIG. 26A shows kinetic activity of MET10 from the reselection and LP1F5' from the original selection is comparable. The percent cleavage of MET10 and LP1F5' upon incubation with crude extracellular mixture of *Legionella pneumophila* (CEM-LP) at room temperature for 1-120 min was fit using the equation $Y=Y_{max}$ [1-e-kt] with Prism (GraphPad, 4.03). Three trials were performed.

FIG. 26B shows the observed rate constants ($k_{obs}$) and maximum cleavage yields ($Y_{max}$) calculated from the data in FIG. 26A.

FIG. 26C shows predicted secondary structure of MET10, showing the predicted stem-loop interactions. MET10=SEQ ID NO: 58.

FIG. 26D shows predicted secondary structure of MET10, showing the predicted pseudoknot interactions. MET10=SEQ ID NO: 58.

Figure 27A:
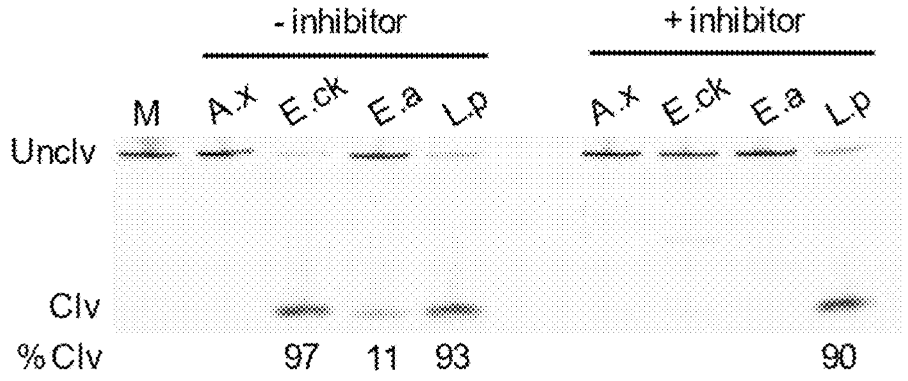

FIG. 27A shows removal of F and Q reduces specificity of 4TFP and MET10 but the addition of RNase inhibitor (SUPERase-In) improves specificity in an exemplary embodiment of the disclosure. FIG. 27A shows the RNA-cleaving activity of 4TFP in the presence (+ inhibitor) and absence (− inhibitor) of the RNase inhibitor towards species capable of inducing non-specific cleavage was determined by gel electrophoresis. Marker lane (M) comprises the full-length sequence. Other lanes are reactions with the crude extracellular mixture (CEM) of the given bacteria: *Achromobacter xylosoxidans* (A.x), *Escherichia coli* K12 (E.ck), *Enterobacter aerogenes* (E.a), and *Legionella pneumophila* (L.p). The dash left to the gel un panels A and B indicates the location of the uncleaved (top) and the cleaved fragment (bottom) within the gel. Incubation time: 1 h.

Figure 27B:
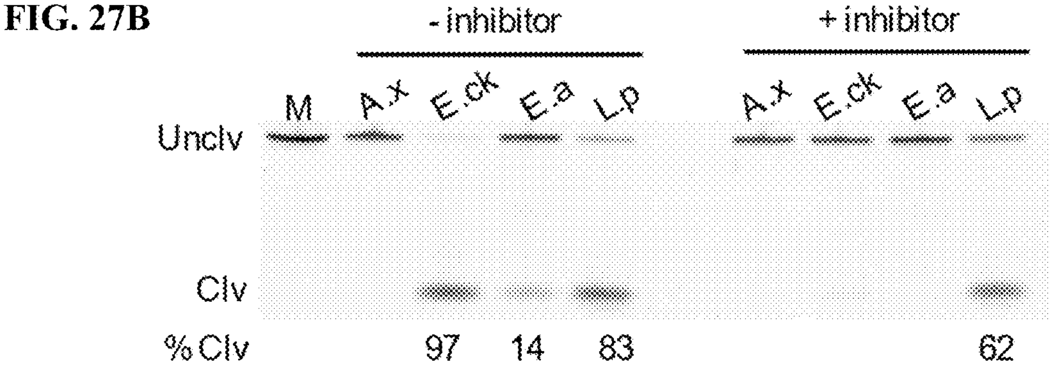

FIG. 27B shows removal of F and Q reduces specificity of 4TFP and MET10 but the addition of Rnase inhibitor (SUPERase-In) improves specificity in an exemplary embodiment of the disclosure. FIG. 27B shows the RNA-cleaving activity of MET10 in the presence (+ inhibitor) and absence (− inhibitor) of the Rnase inhibitor towards species capable of inducing non-specific cleavage was determined by gel electrophoresis. Marker lane (M) comprises the full-length sequence. Other lanes are reactions with the CEM of the given bacteria: *Achromobacter xylosoxidans* (A.x), *Escherichia coli* K12 (E.ck), *Enterobacter aerogenes* (E.a), and *Legionella pneumophila* (L.p). The dash left to the gel un panels A and B indicates the location of the uncleaved (top) and the cleaved fragment (bottom) within the gel. Incubation time: 1 h.

Figure 28:
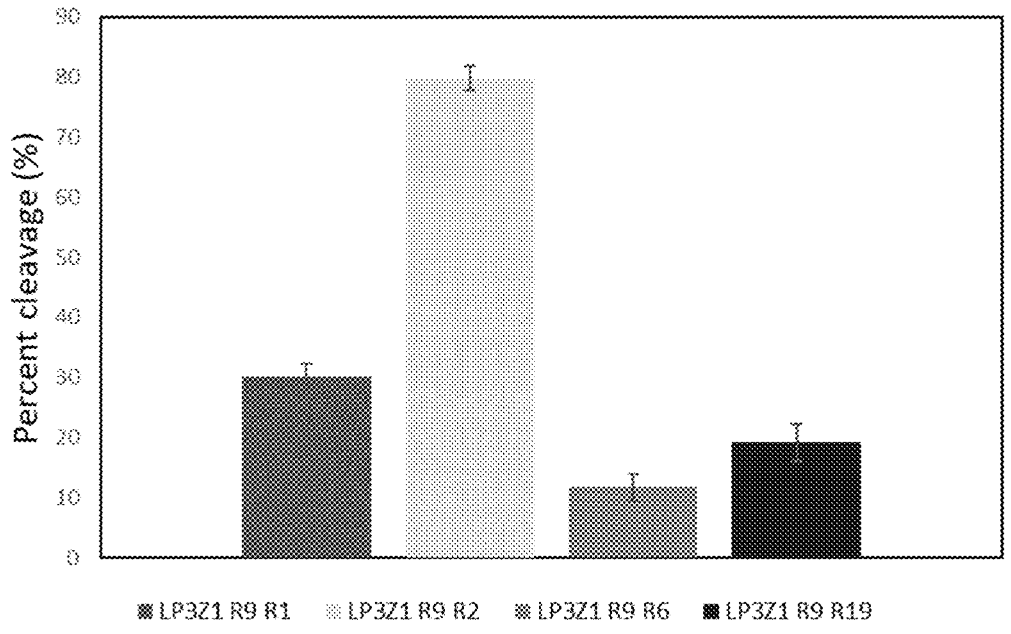

FIG. 28 shows % Cleavage assessment of Rank 1, 2, 6, and 19 from the reselection following a 1 hour incubation with Lp in buffer in an exemplary embodiment of the disclosure. The % cleavage observed from rank 1 (LP3Z1

R9 R1), rank 2 (LP3Z1 R9 R2), rank 6 (LP3Z1 R9 R6) and rank 19 (LP3Z1 R9 R19) were 30, 80, 12 and 19 respectively.

Figure 29:
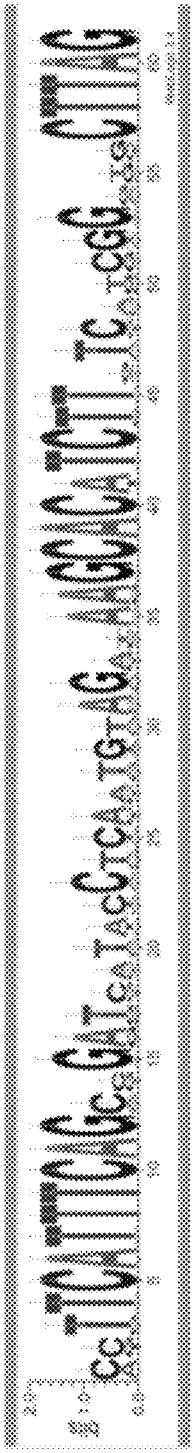

FIG. 29 shows top 50 cluster analysis from round 9 of the reselection aligned against R11-R2 (LP1) in an exemplary embodiment of the disclosure. The image is the sequence logo of a multiple sequence alignment (SEQ ID NO: 189) of the top 50 clusters from round 9 of the reselection population. Conserved positions are proportional to letter height, where 2.0 equals fully conserved. Importantly, only positions 1-56 were subject to selection, the last 5 nucleotides were fixed in the reverse primer and therefore fully conserved. Conservation of positions 3-12 correspond to the substrate binding loop (shown in FIG. 30), and position 39+ were originally fixed as part of the reverse primer in the initial selection. Of particular interest is the conserved region between position 35-48, the portion of which bound to the substrate region showed nearly 100% conservation. Additionally, the cluster analysis revealed that the nucleotide called for each position was identical to LP1, with the exception of position 2 (T→C), 54 (A→G) and 55 (G→T) (SEQ ID NO: 190). The mutations observed at position 2 and 54 were also observed in the % conservation analysis of the top 500 individual sequences shown in FIG. 25.

FIG. 30 shows schematic representation of truncations made to the 4TFP sequence during truncation in an exemplary embodiment of the disclosure. The regions that were truncated are labelled according to the regions that were deleted. Regions in solid lines represent deletions, the base pairs indicated by region 7 were mutated, and the arrows indicate regions of insertions. The cleavage site (rA) is highlighted in the grey circle with the dashed line. The end of the substrate region is indicated by a line labeled SB. Likewise, the end of the forward primer (FP) and beginning of the reverse primer (RP) are indicated. Also see sequences in Table 5, in particular SEQ ID NOS 49-61.

Figure 31:
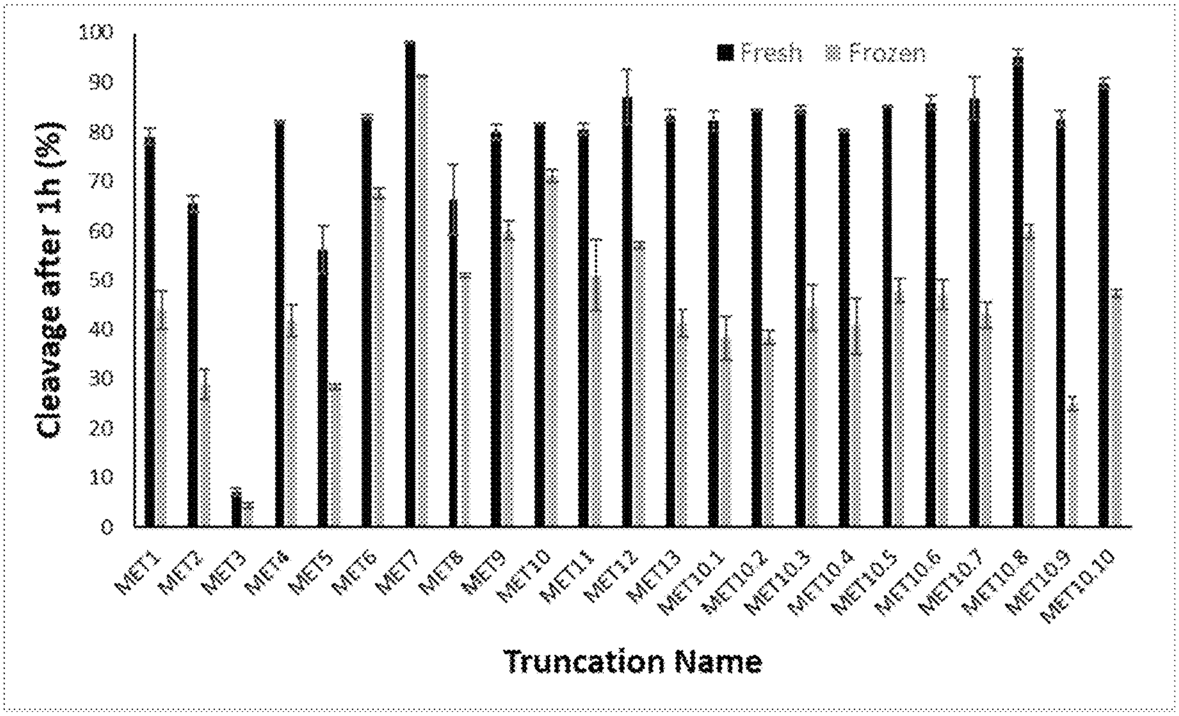

FIG. 31 shows truncated sequences exhibit increased RNA-cleaving activity when incubated with fresh crude extracellular mixture of *Legionella pneumophila* (CEM-LP) in an exemplary embodiment of the disclosure. The RNA-cleaving activity of each truncation in the presence of either fresh or frozen CEM-LP, following a 1 h incubation at room temperature, was determined by gel electrophoresis. Each truncation was evaluated in duplicate and the average percent cleavage for each truncation in either fresh or frozen CEM-LP is shown in the graph.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art.

The term "biosensor" as used herein refers to an analytical device used for the detection of an analyte, which comprises a biological component such as nucleic acids or proteins. A biosensor can be part of a larger biosensor system or is itself a biosensor system.

The term "analyte", "target" or "target molecule" as used herein refers to any agent, including, but not limited to, a small inorganic molecule, small organic molecule, metal ion, biomolecule, toxin, biopolymer (such as a nucleic acid, carbohydrate, lipid, peptide, protein), cell, tissue, microorganism, virus and pathogen, for which one would like to sense or detect. In an embodiment, the analyte is either isolated from a natural source or is synthetic. The analyte can be a single compound or a class of compounds, such as a class of compounds that share structural or functional features. The term analyte also includes combinations (e.g. mixtures) of compounds or agents such as, but not limited to, combinatorial libraries and samples from an organism or a natural environment. In some embodiments, the target is from *Legionella pneumophila*. In some embodiments, the target is a protein target. In some embodiments, the protein target is a protein target of 30-100 kDa.

As used herein, the term "sample" or "test sample" refers to any material in which the presence or amount of an analyte is unknown and can be determined in an assay. The sample can be from any source, for example, any biological (e.g. human or animal samples, including clinical samples), environmental (e.g. water, soil or air) or natural (e.g. plants) source, or from any manufactured or synthetic source (e.g. food or drinks). The sample can be comprised or is suspected of comprising one or more analytes. In some embodiments, the test sample is water. In some embodiments, the water is from a lake, a river, a creek, a hot spring, or other body of water. In some embodiments, the test sample is hot and cold water system water. In some embodiments, the test sample is humidifier water. In some embodiments, the test sample is whirlpool spa water. In some embodiments, the test sample is cooling tower water.

The term "test solution" as used herein refers to a solution that contains the sample. The test solution can be any aqueous solution compatible for the use of the presently disclosed DNAzyme, biosensor and methods for using same. The test solution can be entirely comprised of the sample or it can be a dilution of the sample.

The term "nucleic acid" as used herein refers to biopolymer comprising monomers of nucleotides, such as deoxyribonucleic acid (DNA), ribonucleic acid (RNA) and other polynucleotides of modified nucleotides and/or nucleotide derivatives, and can be either double stranded (ds) or single stranded (ss). "Modified" bases include, for example, tritiated bases and unusual bases such as inosine. A variety of modifications can be made to DNA and RNA; thus "nucleic acid molecule", "DNA molecule", and "RNA molecule" embrace chemically, enzymatically, or metabolically modified forms. Examples of modified nucleotides which can be used to generate the nucleic acids disclosed herein include xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine. Alternatively, the nucleic acid molecules can be produced biologically using an expression vector. In some embodiments, modified nucleotides comprise one or more modified bases (e.g. unusual bases such as inosine, and functional modifications to the bases such as amino modifications), modified backbones (e.g. peptide nucleic acid, PNA) and/or other chemically, enzymatically, or metabolically modified forms. The term "functional fragment" as used herein refers to a fragment of the nucleic acid that retains the functional property of the full-length nucleic acid, for example, the ability of the fragment to act as a DNAzyme for detecting a particular analyte, for example, *Legionella pneumophila*.

The term "nucleic acid cleaving enzyme" as used herein refers to any molecule that accelerates or catalyzes the cleavage of a nucleic acid. The term enzyme as used herein refers to all types of enzymes including protein enzymes, DNAzymes and ribozymes, including allosteric versions which activity is regulated by binding of an effector molecule at a site other than the enzyme's active site.

As used herein, the term "DNAzyme" or deoxyribozyme or aptazyme refers to DNA oligonucleotides that are capable of performing or catalyzing a specific chemical reaction, similar to the action of biological enzymes, which are proteins and ribozymes, upon detecting an analyte. In some embodiments, the DNAzyme or aptazyme is RNA-cleaving and catalyzes the cleavage of a particular substrate, for example a nucleic acid sequence comprising one or more ribonucleotides, at a defined cleavage site. In some embodiments, the DNAzyme or aptazyme cleaves a nucleic acid sequence at a single ribonucleotide linkage thereby producing a nucleic acid cleavage fragment or a cleavage product. In some embodiments, the DNAzyme is for detecting *Legionella pneumophila*. The term "functional fragment" as used herein refers to the ability of the fragment to act as a DNAzyme for detecting a particular analyte, for example, *Legionella pneumophila.*

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this disclosure, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about".

II. DNAzymes, Nucleic Acid, Biosensors, Kits, and Methods

Three versions of LP1 are disclosed: (a) LP1FQ wherein the RNA site is flanked by fluorophore (FAM, F) and quencher (Dabcyl, Q) modified thymidine nucleotides (SEQ ID NO: 7) (b) LP1F3' containing 3' fluorescein (SEQ ID NO: 8) and (c) LP1F5' containing 5' fluorescein (SEQ ID NO: 9). LP1F3' and LP1F5' demonstrate an improvement in the cleavage rate over LP1FQ by 40-fold. This disclosure also relates to truncated versions of LP1 resulting in RNA-cleaving DNAzymes, for example, MET10. MET10 is 55 nucleotides in length compared to the 112 nucleotides in LP1, with nearly maintained activity and favourable specificity compared to the original 112 nucleotide sequence, and a much more practical length for translation to a commercially available portable detection platform.

The DNAzymes in this disclosure are useful for incorporation in simple and user-friendly paper-based and/or solution-based biosensors for on-site monitoring of the contamination of *Legionella pneumophila* in exposure sources, such as cooling water towers.

Accordingly, the present disclosure provides DNAzymes for detecting an analyte, for example, *Legionella pneumophila*. In some embodiments, the DNAzyme comprises or consists of a sequence selected from the group consisting of SEQ ID NOS: 7-71, 187, and 188, or a functional fragment or modified derivative thereof. In some embodiments, the DNAzyme comprises or consists of the sequence of SEQ ID NO: 7, or a functional fragment or modified derivative thereof. In some embodiments, the DNAzyme comprises or consists of the sequence of SEQ ID NO: 8, or a functional fragment or modified derivative thereof. In some embodiments, the DNAzyme comprises or consists of the sequence SEQ ID NO: 9, or a functional fragment or modified derivative thereof. In some embodiments, the DNAzyme comprises or consists of the sequence SEQ ID NO: 10, or a functional fragment or modified derivative thereof. In some embodiments, the DNAzyme comprises or consists of the sequence SEQ ID NO: 11, or a functional fragment or modified derivative thereof. In some embodiments, the DNAzyme comprises or consists of the sequence SEQ ID NO: 12, or a functional fragment or modified derivative thereof. In some embodiments, the DNAzyme comprises or consists of the sequence SEQ ID NO: 13, or a functional fragment or modified derivative thereof. In some embodiments, the DNAzyme comprises or consists of the sequence SEQ ID NO: 14, or a functional fragment or modified derivative thereof. In some embodiments, the DNAzyme comprises or consists of the sequence SEQ ID NO: 15, or a functional fragment or modified derivative thereof. In some embodiments, the DNAzyme comprises or consists of the sequence SEQ ID NO: 16, or a functional fragment or modified derivative thereof. In some embodiments, the DNAzyme comprises or consists of the sequence SEQ ID NO: 17, or a functional fragment or modified derivative thereof. In some embodiments, the DNAzyme comprises or consists of the sequence SEQ ID NO: 18, or a functional fragment or modified derivative thereof. In some embodiments, the DNAzyme comprises or consists of the sequence SEQ ID NO: 19, or a functional fragment or modified derivative thereof. In some embodiments, the DNAzyme comprises or consists of the sequence SEQ ID NO: 20, or a functional fragment or modified derivative thereof. In some embodiments, the DNAzyme comprises or consists of the sequence SEQ ID NO: 21, or a functional fragment or modified derivative thereof. In some embodiments, the DNAzyme comprises or consists of the sequence SEQ ID NO: 22, or a functional fragment or modified derivative thereof. In some embodiments, the DNAzyme comprises or consists of the sequence SEQ ID NO: 23, or a functional fragment or modified derivative thereof. In some embodiments, the DNAzyme comprises or consists of the sequence SEQ ID NO: 24, or a functional fragment or modified derivative thereof. In some embodiments, the DNAzyme comprises or consists of the sequence SEQ ID NO: 25, or a functional fragment or modified derivative thereof. In some embodiments, the DNAzyme comprises or consists of the sequence SEQ ID NO: 26, or a functional fragment or modified derivative thereof. In some embodiments, the DNAzyme comprises or consists of the sequence SEQ ID NO: 27, or a functional fragment or modified derivative thereof. In some embodiments, the DNAzyme comprises or consists of the sequence SEQ ID NO: 28, or a functional fragment or modified derivative thereof. In some embodiments, the DNAzyme comprises or consists of the sequence SEQ ID NO: 29, or a functional fragment or modified derivative thereof. In some embodiments, the DNAzyme comprises or consists of the sequence SEQ ID NO: 30, or a functional fragment or modified derivative thereof. In some embodiments, the DNAzyme comprises or consists of the sequence SEQ ID NO: 31, or a functional fragment or modified derivative thereof. In some embodiments, the DNAzyme comprises or consists of the sequence SEQ ID NO: 32, or a functional fragment or modified derivative thereof. In some embodiments, the DNAzyme comprises or consists of the sequence SEQ ID NO: 33, or a functional fragment or modified derivative thereof. In some embodiments, the DNAzyme comprises or consists of the sequence SEQ ID NO: 34, or a functional fragment or modified derivative thereof. In some embodiments, the DNAzyme comprises or consists of the sequence SEQ ID NO: 35, or a functional fragment or modified derivative thereof. In some embodiments, the DNAzyme comprises or consists of the sequence SEQ ID NO: 36, or a functional fragment or modified derivative thereof. In some embodiments, the DNAzyme comprises or consists of the sequence SEQ ID NO: 37, or a functional fragment or modified derivative thereof. In some embodiments, the DNAzyme comprises or consists of the sequence SEQ ID NO: 38, or a functional fragment or modified derivative thereof. In some embodiments, the DNAzyme comprises or consists of the sequence SEQ ID NO: 39, or a functional fragment or modified derivative thereof. In some embodiments, the DNAzyme comprises or consists of the sequence SEQ ID NO: 40, or a functional fragment or modified derivative thereof. In some embodiments, the DNAzyme comprises or consists of the sequence SEQ ID NO: 41, or a functional fragment or modified derivative thereof. In some embodiments, the DNAzyme comprises or consists of the sequence SEQ ID NO: 42, or a functional fragment or modified derivative thereof. In some embodiments, the DNAzyme comprises or consists of the sequence SEQ ID NO: 43, or a functional fragment or modified derivative thereof. In some embodiments, the DNAzyme comprises or consists of the sequence SEQ ID NO: 44, or a functional fragment or modified derivative thereof. In some embodiments, the DNAzyme comprises or consists of the sequence SEQ ID NO: 45, or a functional fragment or modified derivative thereof. In some embodiments, the DNAzyme comprises or consists of the sequence SEQ ID NO: 46, or a functional fragment or modified derivative thereof. In some embodiments, the DNAzyme comprises or consists of the sequence SEQ ID NO: 47, or a functional fragment or modified derivative thereof. In some embodiments, the DNAzyme comprises or consists of the sequence SEQ ID NO: 48, or a functional fragment or modified derivative thereof. In some embodiments, the DNAzyme comprises or consists of the sequence SEQ ID NO: 49, or a functional fragment or modified derivative thereof. In some embodiments, the DNAzyme comprises or consists of the sequence SEQ ID NO: 50, or a functional fragment or modified derivative thereof. In some embodiments, the DNAzyme comprises or consists of the sequence SEQ ID NO: 51, or a functional fragment or modified derivative thereof. In some embodiments, the DNAzyme comprises or consists of the sequence SEQ ID NO: 52, or a functional fragment or modified derivative thereof. In some embodiments, the DNAzyme comprises or consists of the sequence SEQ ID NO: 53, or a functional fragment or modified derivative thereof. In some embodiments, the DNAzyme comprises or consists of the sequence SEQ ID NO: 54, or a functional fragment or modified derivative thereof. In some embodiments, the DNAzyme comprises or consists of the sequence SEQ ID NO: 55, or a functional fragment or modified derivative thereof. In some embodiments, the DNAzyme comprises or consists of the sequence SEQ ID NO: 56, or a functional fragment or modified derivative thereof. In some embodiments, the DNAzyme comprises or consists of the sequence SEQ ID NO: 57, or a functional fragment or modified derivative thereof. In some embodiments, the DNAzyme comprises or consists of the sequence SEQ ID NO: 58, or a functional fragment or modified derivative thereof. In some embodiments, the DNAzyme comprises or consists of the sequence SEQ ID NO: 59, or a functional fragment or modified derivative thereof. In some embodiments, the DNAzyme comprises or consists of the sequence SEQ ID NO: 60, or a functional fragment or modified derivative thereof. In some embodiments, the DNAzyme comprises or consists of the sequence SEQ ID NO: 61, or a functional fragment or modified derivative thereof. In some embodiments, the DNAzyme comprises or consists of the sequence SEQ ID NO: 62, or a functional fragment or modified derivative thereof. In some embodiments, the DNAzyme comprises or consists of the sequence SEQ ID NO: 63, or a functional fragment or modified derivative thereof. In some embodiments, the DNAzyme comprises or consists of the sequence SEQ ID NO: 64, or a functional fragment or modified derivative thereof. In some embodiments, the DNAzyme comprises or consists of the sequence SEQ ID NO: 65, or a functional fragment or modified derivative thereof. In some embodiments, the DNAzyme comprises or consists of the sequence SEQ ID NO: 66, or a functional fragment or modified derivative thereof. In some embodiments, the DNAzyme comprises or consists of the sequence SEQ ID NO: 67, or a functional fragment or modified derivative thereof. In some embodiments, the DNAzyme comprises or consists of the sequence SEQ ID NO: 68, or a functional fragment or modified derivative thereof. In some embodiments, the DNAzyme comprises or consists of the sequence SEQ ID NO: 69, or a functional fragment or modified derivative thereof. In some embodiments, the DNAzyme comprises or consists of the sequence SEQ ID NO: 70, or a functional fragment or modified derivative thereof. In some embodiments, the DNAzyme comprises or consists of the sequence SEQ ID NO: 71, or a functional fragment or modified derivative thereof. In some embodiments, the DNAzyme comprises or consists of the sequence SEQ ID NO: 187, or a functional fragment or modified derivative thereof. In some embodiments, the DNAzyme comprises or consists of the sequence SEQ ID NO: 188, or a functional fragment or modified derivative thereof. In some embodiments, the DNAzyme comprises (a) LP1FQ wherein the RNA site is flanked by fluorophore (FAM, F) and quencher (Dabcyl, Q) modified thymidine nucleotides (SEQ ID NO: 7), (b) LP1F3' containing 3' fluorescein (SEQ ID NO: 8), or (c) LP1F5' containing 5' fluorescein (SEQ ID NO: 9). LP1F3' and LP1F5' demonstrate an improvement in the cleavage rate over LP1FQ by 40-fold. In some embodiments, the DNAzyme detects at least 10 colony forming units of *Legionella pneumophila.*

In an embodiment, the DNAzyme is specific for *Legionella pneumophila*. In an embodiment, the DNAzyme is activated by *Legionella pneumophila*. In some embodiments, the DNAzyme is specific for *Legionella pneumophila* and inactive with other common bacteria. In some embodiments, the DNAzyme is inactive with *Ochrobactrum grignonense, Brevundimonas diminuta, Achromobacter xylosoxidans, Fusobacterium nucleatum, Streptococcus salivarius, Enterococcus faecium, Listeria monocytogenes, Bacillus subtilis, Veillonella parvula, Clostridium difficile, Bacteroid fragilis, Actinomyces orientalis, Klebsiella aerogenes, Klebsiella pneumoniae, Enterobacter aerogenes, Enterobacter cloacae, Salmonella enterica, Escherichia coli* k12, *Shigella sonnei, Shigella flexneri, Yersinia ruckeri, Hafnia alvei, Serratia fonticola, Acinetobacter lwoffii*, and *Pseudomonas aeruginosa.*

The DNAzyme of the present disclosure can comprise a detectable label. In some embodiments, the detectable label comprises a fluorescent, a colorimetric or other optical probe or electrochemical moiety. In some embodiments, the detectable label is a fluorescent moiety. In some embodiments, the fluorescent moiety is a fluorophore. In some embodiments, the fluorophore is a chemical fluorophore. In some embodiments, the fluorophore is fluorescein. In some embodiments, the fluorescein comprises eosin, calcein, fluorescein amidite (FAM), merbromin, erythrosine, Rose Bengal, or DyLight Fluor, or derivatives thereof, or any other fluorescein that can be incorporated into a DNAzyme. In some embodiments, the fluorophore is 6-Carboxyfluorescein (6-FAM). In some embodiments, the fluorophore is a rhodamine, a coumarin, a cyanine, a TYE™ dye, an ATTO™ dye, an Alexa Fluor® dye, LI-COR IRDyes®, or any other fluorescent dye that can be incorporated into a DNAzyme. In some embodiments, the cyanine is Cy2, Cy3, Cy3B, Cy3.5, Cy5, Cy5.5, or Cy7. In some embodiments, the cyanine is Cy5. In some embodiments, the fluorophore is FAM. The selection of the fluorophore is based upon one or more parameters including, but not limited to, (i) maximum excitation and emission wavelength, (ii) extinction coefficient, (iii) quantum yield, (iv) lifetime, (v) stokes shift, (vi) polarity of the fluorophore and (vii) size.

In some embodiments, the detectable label is a colorimetric moiety. In some embodiments, the colorimetric moiety is urea, nitroblue tetrazolium (NBT), 5-Bromo-4-Chloro-3-Indolyl Phosphate (BCIP), 3,3',5,5'-Tetramethylbenzidine (TMB), 3,3'-Diaminobenzidine (DAB), 2,2'-azino-bis(3-ethylbenzothiazoline-6-sulfonic acid) (ABTS), β-D-glucose, 5-Bromo-4-chloro-3-indolyl-β-galactopyranoside (X-gal), or any other colorimetric moiety that can be incorporated into a DNAzyme. In some embodiments, the colorimetric moiety is catalyzed by an enzymatic moiety. In some embodiments, the enzymatic moiety comprises urease, alkaline phosphatase, horseradish peroxidase, glucose oxidase, β-galactosidase, or any other suitable enzymatic moiety.

Also provided is a nucleic acid comprising or consisting of a sequence selected from the group consisting of SEQ ID NOS: 1-190. In some embodiments, the nucleic acid comprises or consists of a sequence selected from the group consisting of SEQ ID NOS:7-71, 187, and 188. In some embodiments, the nucleic acid comprises or consists of a sequence selected from the group consisting of SEQ ID NOS: 48-71, 187, and 188. In some embodiments, the nucleic acid comprises or consists of a sequence selected from the group consisting of SEQ ID NOS: 7-14, 20-24, 30-36, 45, 48, 54-60, 69, 187, and 188. In some embodiments, the nucleic acid comprises or consists of the sequence of SEQ ID NO: 34 or 58.

Also provided is a biosensor for detecting *Legionella pneumophila* comprising a DNAzyme described herein. In some embodiments, the biosensor comprises a support. In some embodiments, the support is a solid or semi-solid support. In some embodiments, the support comprises cellulose or paper. In some embodiments, the DNAzyme is immobilized on a support. In some embodiments, the biosensor is comprised in a solution. In some embodiments, the solution comprises a buffer described herein.

Further provided herein is a kit for detecting *Legionella pneumophila*, wherein the kit comprises a DNAzyme or biosensor disclosed herein, and instructions for use of the kit. In some embodiments, the kit comprises one or more of: i) a buffer, ii) an RNase inhibitor, and iii) a metal ion. In some embodiments, the buffer comprises phosphate, 4-(2-hydroxyethyl)-1-piperazineethanesulfonic acid (HEPES), Tris(Hydroxymethyl)aminomethane (TRIS), 3-(N-morpholino) propanesulfonic acid (MOPS), N,N-bis(2-hydroxyethyl)-2-aminoethanesulfonic acid (BES), 2-(N-morpholino)ethanesulfonic acid (IVIES), or any suitable buffer. In some embodiments, the RNase inhibitor is an RNase I inhibitor. In some embodiments, the RNAse inhibitor is SUPERase-in Rnase inhibitor. In some embodiments, the metal ion is a divalent ion. In some embodiments, the metal ion is $Mg^{2+}$, $Mn^{2+}$, $Ca^{2+}$, $Cu^{2+}$, $Fe^{2+}$, $Ni^{2+}$, $Co^{2+}$, $Sn^{2+}$, $Cd^{2+}$, or $Zn^{2+}$.

Also provided is a method for detecting the presence of *Legionella pneumophila* in a test sample, comprising contacting said sample with the DNAzyme or biosensor described herein, wherein the presence of *Legionella pneumophila* activates the RNA cleavage activity of the DNAzyme thereby generating a detectable signal. In some embodiments, the RNA cleavage activity of the DNAzyme is activated by unidentified protein targets from *Legionella pneumophila.*

Further provided is a method for detecting the presence of *Legionella pneumophila* in a test sample, comprising:

a) contacting said test sample with the DNAzyme or biosensor described herein, wherein the DNAzyme comprises a detectable label;
b) allowing cleavage of the DNAzyme if a target is present, thereby releasing the detectable label; and
c) measuring a detectable signal if the portion of the DNAzyme comprising the detectable label is released, wherein the RNA cleavage activity of the DNAzyme is activated by a target from *Legionella pneumophila.*

In some embodiments, the presence of *Legionella pneumophila* activates the RNA cleavage activity of the DNAzyme thereby generating a detectable signal. In some embodiments, the target is a protein target. In some embodiments, the protein target is a protein target of 30-100 kDa. In some embodiments, the DNAzyme is activated by at least 10 colony forming units of *Legionella pneumophila.*

Hereinafter are provided examples of specific embodiments and implementations for performing the methods and uses of the present disclosure. The examples are provided for illustrative purposes only, and are not intended to limit the scope of the present disclosure in any way:

EXAMPLES

Example 1: DNAzymes Selections

Materials and Methods

Oligonucleotides and other chemicals: The sequences of the oligonucleotides used in this work are listed in Table 1. They were purchased from Integrated DNA Technologies (IDT) or Yale University. All oligonucleotides were purified by 10% denaturing (8 M urea) polyacrylamide ((v/v) 29:1 bisacrylamide:acrylamide) gel electrophoresis (dPAGE) before use. Each random position in LPL1 DNA library (N40) represents a 25% probability of A, C, G or T nucleotide. γ-[32P]-ATP was purchased from Perkin Elmer. SUPERase-In Rnase inhibitor was purchased from Invitrogen. Water was purified with a Milli-Q Synthesis A10 water purification system.

TABLE 1

Sequences used. Sequences are written 5'-3'.

| Selection | | | SEQ ID No: |
|---|---|---|---|
| LPL1 (82 nt) | | CAAGC ATGGA CAATA CCGAG C-**N40**-ATCT TGTCA TCGGA GGCTT AG | SEQ ID NO: 1 |
| FQ30(30 nt) | | CTATG AACTG ACQRF GACCT CACTA CCAAG | SEQ ID NO: 2 |
| LT1 (30 nt) | | TATTG TCCAT GCTTG CTTGG TAGTG AGGTC | SEQ ID NO: 3 |
| FP1 Forward primer | | CAA GCA TGG ACA ATA CCG AGC | SEQ ID NO: 4 |
| Reverse primer | | CTA AGC CTC CGA TGA CAA GAT | SEQ ID NO: 5 |
| Reverse primer with poly T tail | | TTTTTTTTTTTTTTT-C18-CTA AGC CTC CGA TGA CAA GAT | SEQ ID NO: 6 |
| **DNAzymes** | | | |
| Name | # of nucleotides | | |
| LP1FQ | 112 | CTA TGA ACT GAC QRF GAC CTC ACT ACC AAG CAA GCA TGG ACA ATA CCG AGC CTT TCA TTT CAG CCG ATC ATA CCT CAA TGT AGA TAA GCA CAT CTT GTC ATC GGA GGC TTA G | SEQ ID NO: 7 |
| LP1F3' | 112 | CTA TGA ACT GAC TRT GAC CTC ACT ACC AAG CAA GCA TGG ACA ATA CCG AGC CTT TCA TTT CAG CCG ATC ATA CCT CAA TGT AGA TAA GCA CAT CTT GTC ATC GGA GGC TTA G-FAM | SEQ ID NO: 8 |
| LP1F5' | 112 | FAM - CTA TGA ACT GAC TRT GAC CTC ACT ACC AAG CAA GCA TGG ACA ATA CCG AGC CTT TCA TTT CAG CCG ATC ATA CCT CAA TGT AGA TAA GCA CAT CTT GTC ATC GGA GGC TTA G | SEQ ID NO: 9 |
| LP1P | 112 | CTA TGA ACT GAC TRT GAC CTC ACT ACC AAG PCAA GCA TGG ACA ATA CCG AGC CTT TCA TTT CAG CCG ATC ATA CCT CAA TGT AGA TAA GCA CAT CTT GTC ATC GGA GGC TTA G | SEQ ID NO: 10 |

Abbreviations include: 40 nucleotide random region (N40 in bold), adenosine ribonucleotide (R), fluorescein-dT (F), DABCYL-dT (Q), 6-FAM (fluorescein) (FAM), γ-[32P] (P). Underlined nucleotides in the DNAzymes denote the substrate sequence.

Bacterial strains and culture conditions: *Legionella pneumophila* serotypes 1, 2, and 3 were cultured from a frozen stock (ATCC® 33152™, 33154™, 33155™, respectively) on phosphate buffered charcoal yeast extract (BCYE) agar plates for 3-4 days in a 37° C. incubator, as previously described [16,17]. *Legionella micdadei, Legionella dumofii, Legionella longbeachae* NSW150 and the *Legionella pneumophila* strains Philadelphia-1 (CDC), Paris, 130b, Lens and Toronto-2005, were grown from frozen stock on BCYE plates for 4 days at 37° C. Single colonies were patched onto fresh plates and grown for 2 days at 37° C. A single patch was used to inoculate a series of dilutions grown overnight at 37° C. in BYE. To make crude extracellular mixture (CEM) (see below) the cultures for *L. dumofii* and *L. micdadei* were at an OD600 of, while *L. longbeachae* and *Legionella pneumophila* were at an OD600 of 1.2 and 1.6, respectively. For CEM preparation of the *Legionella pneumophila* strains series: Philadelphia, Paris, 130b, Lens, and Toronto-2005 the cultures were at OD600 2.6 and 1 for Philadelphia, 1.4 for Paris, 1 for 130b and Lens, and 1.4 for Toronto-2005.

Preparation of CEM from bacterial strains: After growing on BCYE plates for 3-4 days, a single colony of each *Legionella pneumophila* strain was inoculated in 5 mL of buffered yeast extract (BYE) until OD600 reached ~1. The bacterial cultures were then transferred into new microcentrifuge tubes and centrifuged at 6000 rpm at 4° C. for 5 min. The supernatant, now termed CEM-LP, was recovered and passed through a 0.22 μm filter using a syringe. CEM was aliquoted into microcentrifuge tubes and stored at −80° C. until further use. All other bacteria from this study were grown according to their designated growth conditions and CEM was prepared as described. CEM of other bacteria were kindly provided by Dingran Chang.

In vitro selection: In vitro selection was performed as previously described [18-21]. Briefly, 500 pmol of LP3 was phosphorylated (reaction volume: 50 μL) with 30 units of T4 polynucleotide kinase (PNK) for 30 min at 37° C. in 10×PNK buffer (Thermo Scientific). This was followed by ethanol precipitation. Equimolar LP3T and FQ30 along with $ddH_2O$ were then added to the resuspended pellet and the mixture was heated at 90° C. for 1 min and cooled to room temperature for 10 min. Then, 10 μL of 10×T4 DNA ligase buffer (Thermo Scientific) was added followed by 15 units of T4 DNA ligase (reaction volume: 100 μL) and incubated at room temperature for 2 h The DNA molecules in the mixture were concentrated by ethanol precipitation and the ligated FQ30-LP3 molecules were purified by 10% dPAGE.

The purified FQ30-LP3 was dissolved in 125 μL of 2× selection buffer (SB) (100 mM HEPES, pH 7.0, 300 mM NaCl, 30 mM $MgCl_2$) along with equal amounts (33.3 μL) of BYE, CEM-*Pseudomonas aeruginosa*, CEM-*Klebsiella pneumoniae* and the volume was adjusted to 250 μL with $ddH_2O$. This mixture was incubated at room temperature overnight. After ethanol precipitation, the un-cleaved FQ30-LP3 molecules were purified by 10% dPAGE and the pellet stored at −20° C. until further use. Thirteen point three μL of CEM-LP serotypes 1, 2, and 3 were mixed with 50 μL of 2×SB and added to 100 pmol of the un-cleaved FQ30-LP3 molecules (reaction volume: 100 μL). This mixture was incubated at room temperature for 2 h. After ethanol precipitation, the cleaved fragment was purified by 10% dPAGE and used as the template for PCR. The percentage of cleaved FQ30-LP3 was also determined and used to measure the progress of selection. The PCR1 mixture (50 μL) contained 5 μL of the template prepared above, 0.5 μM each of LP3-F and LP3-R, 200 μM each of dNTPs (dATP, dCTP, dGTP and dTTP), 10×PCR buffer (500 mM KCl, 100 mM Tris HCl (pH 9.0 at 25° C.), 15 mM MgCl2, 1% Triton X-100) and 2.5 units of *Thermus thermophilus* DNA polymerase (GenScript). The DNA was amplified using the following thermocycling steps: 95° C. for 1 min; 8 cycles of 95° C. for 45 s, 52° C. for 45 s, and 72° C. for 45 s. For the PCR2 reaction, 50 μL of the PCR1 product was diluted with $ddH_2O$ to 250 μL in a bulk amplification using primers LP3-F and LP3-R-SP18 and the same protocol for PCR1 for a total of 15 cycles. The LP3 strand was purified by 10% dPAGE (yield approximately 400-500 pmol) and used for the next selection round. A total of 11 cycles of selection were conducted. The DNA population from round 11 was cloned and sequenced.

Construction of substrate-DNAzyme cis constructs: The catalytic domain was first phosphorylated with PNK. Typically, 600 pmol of the catalytic domain was combined with 20 units of PNK, 10×PNK buffer, and $ddH_2O$ (reaction volume: 100 μL). The reaction mixture was incubated at 37° C. for 30 min, quenched at 90° C. for 5 min, then ethanol precipitated with 2.5× volume 100% ethanol. The remaining ethanol was evaporated on a 90° C. heat block. The phosphorylated catalytic domain was then combined with 600 pmol of template, 600 pmol of substrate, water (400 μL, total volume), and heated for 1 min at 90° C. then allowed to cool at room temperature for 10-15 min. Following this cooling period, 20 units of ligase and 10× ligase buffer was added and the reaction was incubated at room temperature for 2 h. After incubation the reaction was ethanol-precipitated and purified by 10% dPAGE. Construction of LP1P involved a small-scale phosphorylation whereby 5 pmol of the catalytic domain was phosphorylated (reaction volume: 10 μL) with 5 μCi [γ-32P]ATP (Perkin Elmer) and 10 units of PNK in 10×PNK buffer at 37° C. for 40 min. Thirty-six μL of $ddH_2O$ and 4 μL of PNK buffer were then added to the mixture resulting in a 50 μL final volume. This mixture was ethanol precipitated with 100% ethanol only and the remaining ethanol was evaporated on a 90° C. heat block. The phosphorylated catalytic sequence was then combined with 5 pmol of splint, 5 pmol of substrate, and water and heated for 1 min at 90° C. then allowed to cool at room temperature for 10-15 min. Following this cooling period, 5 units of ligase and 10× ligase buffer was added and the reaction (20 total volume) was incubated at room temperature for 2 h. Remaining steps follow same protocol as described above.

Cleavage reactions: Typically, the DNAzyme (1 μL of 1 μM stock) and 2×SB were combined and heated at 90° C. for 1 min then allowed to cool at room temperature for 10-15 min. After cooling, 4 μL of CEM was added and the reaction (10 total volume) was incubated at room temperature for a specified period. After the designated incubation time the reaction was terminated by the addition of 2× quenching buffer (QB) containing 60 mM EDTA, 7M urea and loading dye solution. The cleaved DNA products were separated from the un-cleaved by 10% dPAGE and images of the gel were obtained using a Typhoon 9200 variable mode imager (GE Healthcare). Imaging parameters were set as follows: emission filter: 526 SP Fluorescein, Cy2, AlexaFluor488; laser: blue (488 nm); PMT: 400; Focal plane: +3; 200 pixels. The images were analyzed using Image Quant software and the percent cleavage for each DNAzyme was calculated using the following formulas: % $Clv=(F_{Clv}/6)/[(F_{Clv}/6)+F_{Uncl}]$ for Lp1 and % $Clv=(F_{Clv})/(F_{Clv}+F_{Uncl})$ for all other DNAzymes. $F_{Clv}$: volume of cleaved band; $F_{Uncl}$: volume of un-cleaved band. The quencher molecule can only quench the fluorescence of the fluorophore when in close enough proximity to the fluorophore, approximately 100 angstroms [22]. This interaction is not perfect and therefore some fluorescence is still observed even when the quencher is neighbouring the fluorophore. To account for this, it is necessary to divide by 6, as previously determined experimentally [23].

Cooling tower water cleavage reactions: For the cooling tower water tests, a master mixture containing 0.1 μM of LPF5' DNAzyme and 10×SB was heated at 90° C. for 1 min then allowed to cool at room temperature for 10-15 min. Each cooling tower was subject to a positive test containing 5 μL of cooling tower water, 3 μL of CEM-LP serotype 1, 1 μL of Lp5, and 1 μL of 10×SB (10 μL total volume) and a negative test containing 8 μL of cooling tower water, 1 μL of Lp5 and 1 μL of 10×SB (10 μL total volume). The positive and negative tests were conducted in duplicate for each cooling tower and were incubated at room temperature for 1 h. After the 1 h incubation period the reaction was terminated via the addition of 2×QB. The cleaved DNA products were separated from the un-cleaved by 10% dPAGE and images of the gel were obtained using an Amersham Typhoon. Imaging parameters were set as follows: Filter—Cy2, laser—488 nm, Auto PMT, 100 pixels. The images were analyzed using Image Quant software and the percent cleavage for each DNAzyme was calculated using the following formula: % $Clv=(F_{Clv})/(F_{Clv},+F_{Unclv})$. Water from each cooling tower was sent for culturing to determine if it contained *Legionella pneumophila* and a report for each cooling tower detailing the treatment reagents and doses was completed.

Kinetic analysis of DNAzymes: All cleavage reactions were conducted in a 400 master mixture containing 0.1 μM of DNAzyme. The DNAzyme, 2×SB (200 μL) and water were heated for 1 min at 90° C. and cooled at room temperature for 15 min. After cooling CEM (160 μL) was added and the reaction (400 μL, total volume) was incubated at room temperature for specified time points, either: 1, 5, 10, 15, 30, 60, 90, 120, 240, 480, 720 min or 1, 5, 10, 15, 30, 60, 90 min. Ten μL was withdrawn from the master mixture at each given timepoint in triplicate and quenched with quenching buffer. The cleavage products from a reaction time course were separated by 10% dPAGE and quantified using a Typhoon 9200 variable mode imager (GE Healthcare) and Image Quant software. Imaging parameters were set as follows: emission filter: 526 SP Fluorescein, Cy2, AlexaFluor488; laser: blue (488 nm); PMT: 400; Focal plane: +3; 200 pixels. Apparent rate constants were determined by curve-fitting the percent cleavage of the DNAzyme in the presence of *Legionella pneumophila* CEM versus reaction time using Prism (GraphPad, 4.03) where $Y=Y_{max}[1-e^{-kt}]$, $Y_{max}$ represents the maximal cleavage yield and k is the observed first-order rate constant ($k_{obs}$).

Estimation of CEM-LP target size: Two 4004, aliquots of CEM-LP were taken and individually passed through a membrane based molecular sizing centrifugal column with molecular weight cut-off of 3K (3,000 Daltons), 10K, 30K, 50K, 100K (all Amicon Ultra-0.5 mL Centrifugal Filters), and 300K (Pall Nanosep® Centrifugal Devices with Omega™ membrane 300K), respectively. The filtrate and concentrate from each column was then used for LPF5' cleavage investigation using dPAGE analysis.

Cleavage test using CEM-LP treated with Proteinase K: To treat CEM-LP with proteinase K (PK; Thermo Scientific), 5 μL of 20 mg/mL PK stock was mixed with 1004, of CEM-LP and incubated at 37° C. for 1 h. Following this step, 1 μL of 1 μM LPF5' stock was added to 5 μL of 2×SB and 44, of PK treated CEM-LP and this mixture was further incubated at room temperature for 1 h. The reaction was then quenched with 2×QB and analyzed using 10% dPAGE.

Reselection: Typically, 300 pmol of LP3Z1 library (catalytic domain) was phosphorylated (reaction volume: 100 μL) with ATP (final concentration 10 mM), and 20 U of PNK for 30 min at 37° C. in 1×PNK buffer. The reaction was quenched by heating the mixture at 90° C. for 10 min. This was followed by ethanol precipitation. Equimolar LP3Z1-FQ30 ligation template and LP3Z1-FQ30 substrate along with $ddH_2O$ were then added to the resuspended pellet and the mixture was heated at 90° C. for 1 min and cooled at room temperature for 10 min. Then, 20 μL of 10×T4 DNA ligase buffer (Thermo Scientific) was added followed by 20 units of T4 DNA ligase (reaction volume: 200 μL) and incubated at room temperature for 2 h The ligation reaction was concentrated by ethanol precipitation and products purified on 7M urea 10% dPAGE. The purified LP3Z1-FQ30 library was dissolved in 50 μL of 2× Selection Buffer (SB) along with equal volumes (10 μL) of BYE, CEM-*Pseudomonas aeruginosa*, CEM-*Klebsiella pneumoniae* and balance water (reaction volume: 100 This mixture was incubated at room temperature overnight. After ethanol precipitation, the un-cleaved LP1FQ molecules were purified by 10% dPAGE and the pellet stored at −20° C. until further use. 10 μL each of CEM-LP serotypes 1, 2, and 3 were mixed with 50 μL of 2×SB and added to 100 pmol of the un-cleaved LP1FQ molecules, balance water (reaction volume: 100 This mixture was incubated at room temperature for 2 h for round 1, 1 h for rounds 2-5, and 30 min for rounds 6-10. After ethanol precipitation, the cleaved fragment was purified by 10% dPAGE and used as the template for PCR. The percentage of cleaved LP1FQ was also determined and used to measure the progress of selection. The PCR1 mixture (50 μL) contained 5 μL of the template, 0.5 μM each of forward (LP3Z1-F) and reverse (LP3Z1-R) primer, 200 μM each of dNTPs (dATP, dCTP, dGTP and dTTP), 10×PCR buffer (500 mM KCl, 100 mM Tris HCl (pH 9.0 at 25° C.), 15 mM $MgCl_2$, 1% Triton X-100) and 2.5 units of *Thermus thermophilus* DNA polymerase (GenScript). The DNA was amplified using the following thermocycling steps: 95° C. for 1 min 10-14 cycles of 95° C. for 30 s, 52° C. for 30 s, and 72° C. for 30 s. For the PCR2 reaction, 60 μL of the PCR1 product was diluted with $ddH_2O$ to 3000 μL in a bulk amplification using primers LP3Z1-F and LP3Z1-R-SP18 and the same protocol for PCR1 for 10-14 cycles. The LP1FQ strand was purified by 10% dPAGE (yield approximately 250 pmol) and used for the next selection round. A total of 10 cycles of selection were conducted. The DNA population from round 9 was cloned and sequenced as described for the original selection [24].

Assessment of cleavage activity (selection libraries, top ranked sequences from reselection, and selectivity): Cleavage reactions were conducted as previously described [24]. Typically, the DNAzyme (1 μL of 1 μM stock) and 2×SB were combined and heated at 90° C. for 1 min then allowed to cool at room temperature for 10-15 min. After cooling, 4 μL of CEM was added and the reaction (10 total volume) was incubated at room temperature for a specified period. After the designated incubation time the reaction was terminated by the addition of 2× quenching buffer (QB) containing 60 mM EDTA, 7M urea and loading dye solution. The cleaved DNA products were separated from the uncleaved by 10% dPAGE and images of the gel were obtained using a Typhoon 9200 variable mode imager (GE Healthcare). Imaging parameters were set as follows: emission filter: 526 SP Fluorescein, Cy2, AlexaFluor488; laser: blue (488 nm); PMT: 400; Focal plane: +3; 200 pixels. The images were analyzed using Image Quant software and the percent cleavage for each DNAzyme was calculated using the following formulas: % $Clv=(F_{Clv}/6)/[(F_{Clv}/6)+F_{Uncl}]$ for DNAzyme containing the fluorophore (F) and quencher (Q) moieties and % $Clv=(F_{Clv})/(F_{Clv}\ F_{Unclv})$ for all other DNAzymes containing only the fluorophore modified nucleotide. FClv: volume of cleaved band; Funclv: volume of un-cleaved band. The quencher molecule can only quench the fluorescence of the fluorophore when in close enough proximity to the fluorophore, approximately 100 angstroms [25]. This interaction is not perfect and therefore some fluorescence is still observed even when the quencher is neighbouring the fluorophore. To account for this, divide by 6, as previously determined experimentally [26]

Mutational Analysis: The percent conservation of each nucleotide position in the top 500 sequences from the reselection round 9 library were examined using Excel. Briefly, each sequence was expanded from a single cell in its own row such that each nt was in its own cell in a new column. The frequency of each nt at each position was determined and converted to a percent. The % conservation of each position was mapped onto the predicted secondary structure of 4TFP. Truncations were designed according to the following set of rules given that the reselection template was mutated at 30%: percent conservation values above 90% were considered highly conserved and essential, values from 70-89 were conserved and can be essential, and values below 70% indicated a nt was potentially destabilizing. A total of 23 truncations were designed using this method.

Example 2. Selection and Characterization of an RNA-Cleaving DNAzyme Specifically Activated by *Legionella pneumophila*

A DNAzyme activated by *Legionella pneumophila* was generated via in vitro selection: The selection approach is summarized schematically in FIG. 9. The DNA library used for the selection (FIG. 1A) contained 40 random nucleotides. The RFD candidate sequence examined in this work is shown in FIG. 1B. Candidate RFDs in the pool were designed to catalyze the cleavage of a single RNA linkage (R) embedded in an otherwise entirely DNA sequence. Unique to this design is that the RNA site is flanked by fluorophore (FAM, F) and quencher (Dabcyl, Q) modified thymidine nucleotides (FIG. 1C). In the absence of *Legionella pneumophila*, the DNAzyme remained inactivated and intact. However, in the presence of *Legionella pneumophila*, the DNAzyme cleaved itself at the RNA site.

Figure 9:
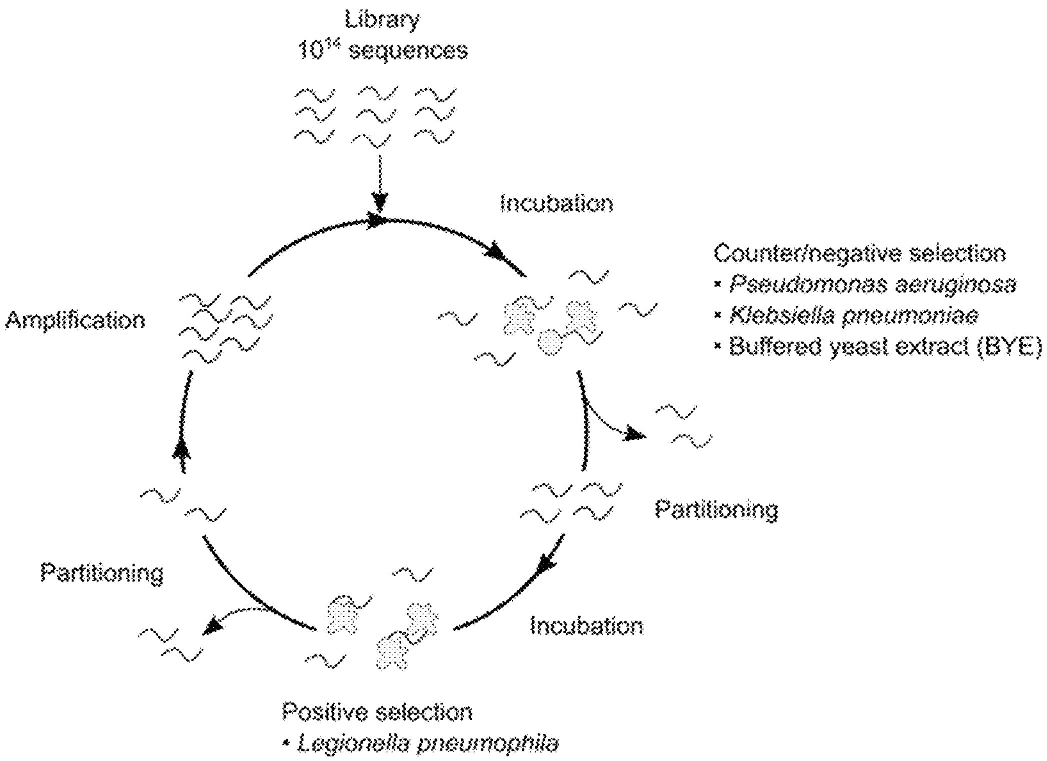
FIG. 9 shows the in vitro selection schematic for the isolation of a DNAzyme specific for *Legionella pneumophila* in an exemplary embodiment of the disclosure. The selection began with a library containing $10^{14}$ unique sequences. The library was first incubated in a counter selection step with *Pseudomonas aeruginosa* (PA) and *Klebsiella pneumoniae* (KP) to eliminate any non-specific cleaving sequences. dPAGE was used to isolate uncleaved sequences, which were then incubated with *Legionella pneumophila*. The sequences that were cleaved this time were isolated via dPAGE and amplified by PCR. One completion of the circle represents one round of selection. Eleven rounds of selection were conducted, with the negative selection applied at rounds 2, 4, 6, 8, 10.
Figure 10:
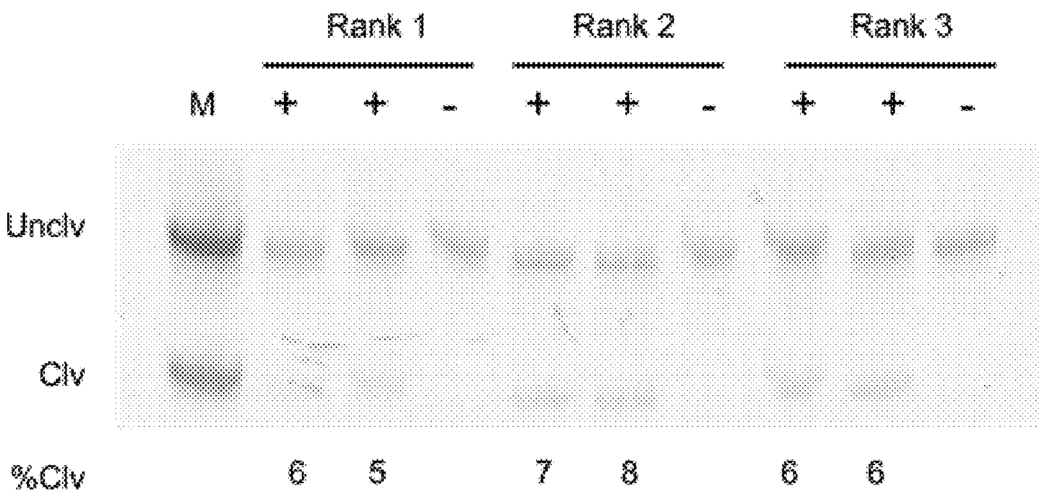
FIG. 10 shows that rank 2 exhibits highest RNA-cleaving activity in an exemplary embodiment of the disclosure. The RNA-cleaving activity of the top 3 ranked sequences was assessed in the presence of crude extracellular mixture of *Legionella pneumophila* (CEM-LP) (+) and reaction buffer only. Reaction time: 1 hour. Marker (M) lane comprises the full-length uncleaved LP1FQ sequence (Unclv) and the cleaved (Clv) LP1FQ sequence.
Figure 11:
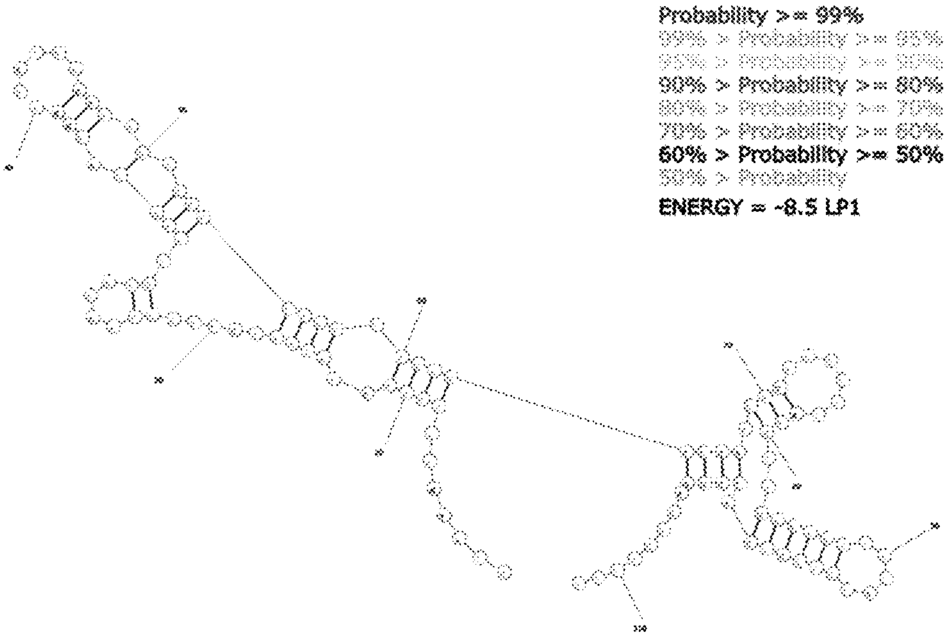
FIG. 11 shows the predicted secondary structure of the *Legionella pneumophila* DNAzyme LP1 in an exemplary embodiment of the disclosure: The secondary structure of LP1 was obtained using RNAstructure10 Web Servers for RNA Secondary Structure Prediction.
Figure 12:
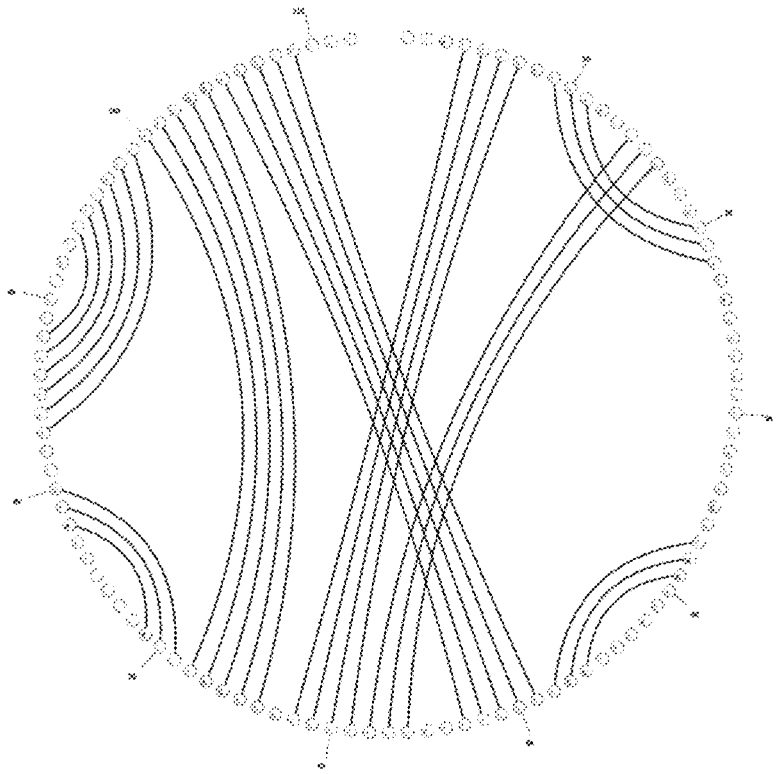
FIG. 12 shows the predicted secondary structure of the *Legionella pneumophila* DNAzyme LP1 in an exemplary embodiment of the disclosure: The sequence was also analyzed for its probability to form a pseudoknot, interactions of which are indicated by crossed lines.

Prior to the start of selection, crude extracellular mixture (CEM) was prepared from *Legionella pneumophila* serogroups 1, 2, and 3 (LP), *Pseudomonas aeruginosa* (PA) and *Klebsiella pneumoniae* (KP). The DNA library was first incubated with CEM-PA, CEM-KP and buffered yeast extract (BYE) at room temperature overnight, representing the counter selection step (FIG. 9). The uncleaved (intact) DNA molecules were purified and then incubated with CEM-LP for 2 h at room temperature, representing the positive selection step. Following incubation, the cleaved DNA molecules were purified by denaturing (8 M urea) polyacrylamide gel electrophoresis (dPAGE) and amplified to regenerate an enriched pool using a previously published protocol. [27] In total, 11 rounds were conducted with the negative selection step included every other round. The 11th DNA pool was sequenced, and the top 100 sequences (SEQ ID NOS: 86-195) were ranked based on abundance and enrichment (Table 2). The RNA-cleaving activity of the top three ranking sequences towards CEM-LP was assessed (FIG. 10). After a 1-h incubation at room temperature with CEM-LP, the rank 2 DNAzyme demonstrated the highest cleavage activity. This sequence was named LP1 (FIG. 1B and FIG. 1C) and chosen for further investigation. Its predicted secondary structure is shown in FIG. 11 and FIG. 12.

Figure 2A:
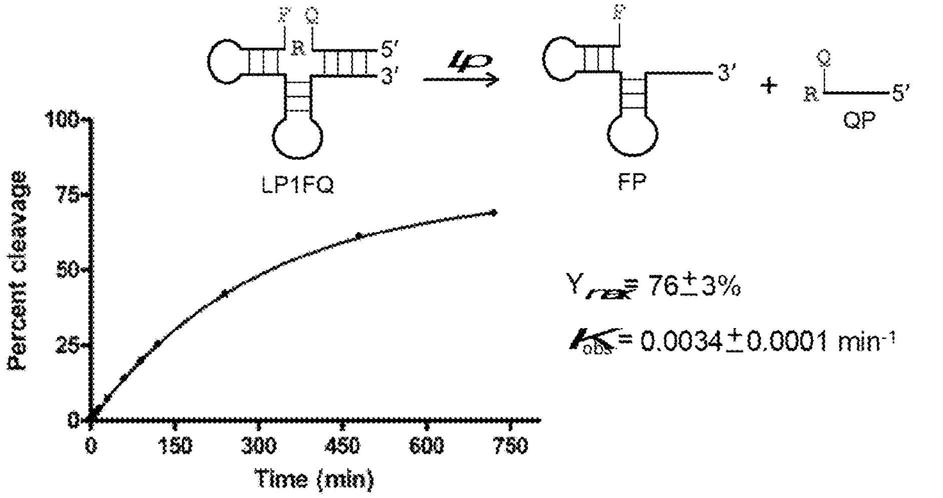
FIG. 2A shows the kinetic profile of LP1FQ in an exemplary embodiment of the disclosure.
Figure 2B:
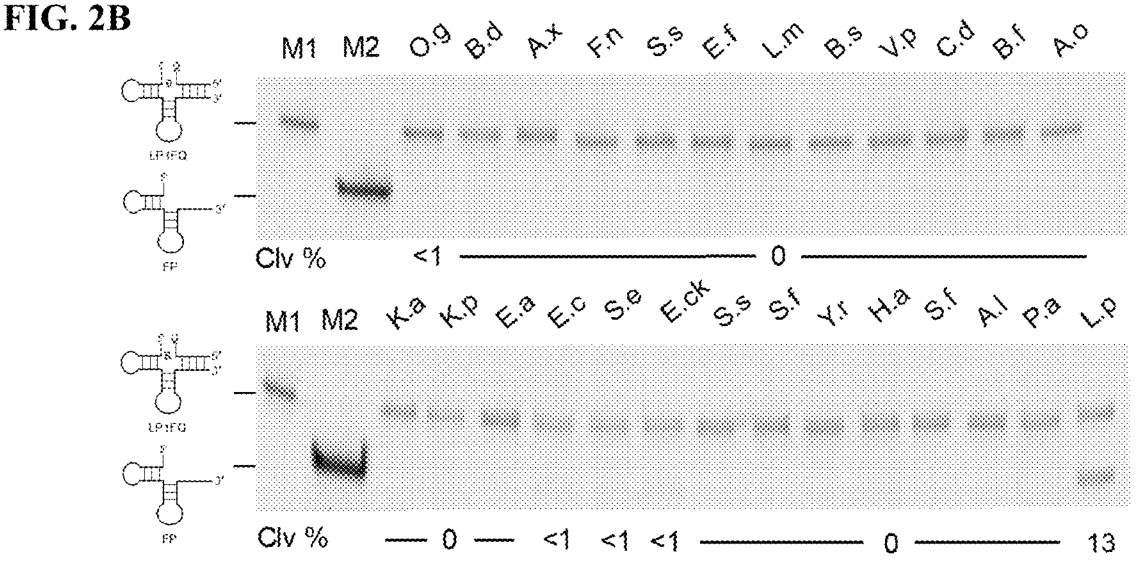
FIG. 2B shows the kinetic profile of LP1FQ in an exemplary embodiment of the disclosure.

RNA-cleaving activity of LP1 is specific to *Legionella pneumophila*: First it was determined how the selected RFD behaved in the presence of CEM-LP. The kinetic profile of LP1FQ was established to determine the apparent cleavage rate (FIG. 2A). A master mix of LP1FQ was prepared, with the addition of CEM-LP (prepared from $10^9$ CFUs/mL; CFU: colony forming units) representing the incubation start time. Aliquots were removed at each timepoint, then analysed using dPAGE. The percent cleavage for each timepoint was calculated and fit to a curve over reaction time. An apparent rate constant of $3.4\times10^{-3}$ $min^{-1}$ was determined for LP1FQ. The RNA-cleaving activity of LP1 towards 26 different bacterial species was also investigated (FIG. 2B). Following a 1-h incubation at room temperature, only CEM-LP was capable of robustly cleaving LP1FQ. A very weak activity (less than $1/10^{th}$ of the activity seen with *Legionella pneumophila*) was also observed for *Enterobacter cloacae, Salmonella enterica, E. coli* and *Ochrobactrum grignonense*.

TABLE 2

Top 100 Sequences from the $11^{th}$ Round of Selection

| Rank | Frequency | Sequence | SEQ ID NO: |
|---|---|---|---|
| 1 | 0.229751273 | AACGGTTGCTCTCATAAGAGTGATGCCGATTCATTTCCAC | 86 |
| 2 | 0.195808472 | CTTTCATTTCAGCCGATCATACCTCAATGTAGATAAGCAC | 87 |
| 3 | 0.177338884 | AGCAACTGGGACAGATCGACAGCCTTTCATTTCAAGTCAC | 88 |
| 4 | 0.074682003 | AACGGTTGCTCCCATAAGAGTGATGCCGATTCATTTCCAC | 89 |
| 5 | 0.038404042 | AACGGTTGCCCTCATAAGAGTGATGCCGATTCATTTCCAC | 90 |
| 6 | 0.037167857 | CTTTCATTTCAGCCGATTATACCTCAATATAGATAAGCAC | 91 |
| 7 | 0.032734058 | CTTTCATTTCAGCCGATCATACCTCAATATAGATAAGCAC | 92 |
| 8 | 0.02878637 | AGCAACTGGGACAGACCGACAGCCTTTCATTTCAAGTCAC | 93 |
| 9 | 0.015873078 | AGCAACTGTGACAGATCGACAGCCTTTCATTTCAAGTCAC | 94 |
| 10 | 0.013703875 | AGGAACTGGGACAGATCGACAGCCTTTCATTTCAAGTCAC | 95 |
| 11 | 0.010412175 | AACGGTTGCTCTCATAAGGGTGATGCCGATTCATTTCCAC | 96 |
| 12 | 0.009753573 | AGTAACTGGGACAGATCGACAGCCTTTCATTTCAAGTCAC | 97 |
| 13 | 0.006859125 | AGCAACTGGGACAGATCGACAGCCTTTCATTTCAAGCCAC | 98 |
| 14 | 0.006569026 | AACGGTTGTTCTCATAAGAGTGATGCCGATTCATTTCCAC | 99 |
| 15 | 0.005215235 | AGCAACTGGGACAGACCGACAGCCTTTCATTTCAAGCCAC | 100 |
| 16 | 0.003019897 | AACGGTTGCCCCCATAAGAGTGATGCCGATTCATTTCCAC | 101 |
| 17 | 0.00281343 | CTTTCATTTCAGCCGATCATACCTCAATATAGACAAGCAC | 102 |
| 18 | 0.002058129 | CCCAGGCATTGCAAGGTTGACTCTCCGATCATTTTCACAC | 103 |
| 19 | 0.001973191 | CTTTCATTTCAGCCGATCATACCCCAATGTAGATAAGCAC | 104 |
| 20 | 0.001935295 | AACGGTTGCTCACATAAGAGTGATGCCGATTCATTTCCAC | 105 |
| 21 | 0.001560258 | GACGGTTGCTCTCATAAGAGTGATGCCGATTCATTTCCAC | 106 |
| 22 | 0.001519749 | GGCAACTGGGACAGATCGACAGCCTTTCATTTCAAGTCAC | 107 |
| 23 | 0.001441344 | AGTAACTGGGACAGACCGACAGCCTTTCATTTCAAGTCAC | 108 |
| 24 | 0.001369473 | AGCAACTGGGACAGATCGACCGCCTTTCATTTCAAGTCAC | 109 |

TABLE 2-continued

Top 100 Sequences from the 11th Round of Selection

| Rank | Frequency | Sequence | SEQ ID NO: |
|---|---|---|---|
| 25 | 0.001272773 | AGGAACTGGGACAGATCGACAGCCTTTCATTTCAAGCCAC | 110 |
| 26 | 0.001232264 | CTTTCATTTCAGCCGATCATACCTCAATGTAGACAAGCAC | 111 |
| 27 | 0.00122181 | AACGGTTGGTCTCATAAGAGTGATGCCGATTCATTTCCAC | 112 |
| 28 | 0.001139485 | CTTTCATTTCAGCCGATTATACCTCAATGTAGATAAGCAC | 113 |
| 29 | 0.001016651 | AGTAACTGGGACAGATCGACAGCCTTTCATTTCAAGCCAC | 114 |
| 30 | 0.000993129 | CTTTCATTTCAGCCGATCATGCCTCAATGTAGATAAGCAC | 115 |
| 31 | 0.000935632 | AGAAACTGGGACAGATCGACAGCCTTTCATTTCAAGTCAC | 116 |
| 32 | 0.000866374 | AACGGTTGCCTTCATAAGAGTGATGCCGATTCATTTCCAC | 117 |
| 33 | 0.000852 | AGCGGTTGCTCTCATAAGAGTGATGCCGATTCATTTCCAC | 118 |
| 34 | 0.00084024 | AGCAACTGGGACAGATCGACAGCCTTTCATTTCCAC | 119 |
| 35 | 0.000816718 | CACGGTTGCTCACATAAGAGTGATGCCGATTCATTTCCAC | 120 |
| 36 | 0.000653374 | CTTTCATTTCAGCCGATCATACCTCTATGTAGATAAGCAC | 121 |
| 37 | 0.000628546 | GACGGTTGCTCCCATAAGAGTGATGCCGATTCATTTCCAC | 122 |
| 38 | 0.00058281 | AGCAACTGGGACAGATCGACGGCCTTTCATTTCAAGTCAC | 123 |
| 39 | 0.000572356 | CCCGGGCATTGCAAGGTTGATTCTCCGATCATTTTCACAC | 124 |
| 40 | 0.000552755 | AACGGTTGCTCCTATAAGAGTGATGCCGATTCATTTCCAC | 125 |
| 41 | 0.000548835 | AGCGGTTGCTCCCATAAGAGTGATGCCGATTCATTTCCAC | 126 |
| 42 | 0.000533154 | CTTTCATTTCAGCCGATCATACTTCAATGTAGATAAGCAC | 127 |
| 43 | 0.00053054 | AGGAACTGGGACAGACCGACAGCCTTTCATTTCAAGTCAC | 128 |
| 44 | 0.000521393 | AGCAACTGTGACAGACCGACAGCCTTTCATTTCAAGTCAC | 129 |
| 45 | 0.000507019 | AGCAACTGTGACAGATCGACAGCCTTTCATTTCAAGCCAC | 130 |
| 46 | 0.000505712 | CCCAGGCATTGCAAGGTTGATTCTCCGATCATTTTCACAC | 131 |
| 47 | 0.000475657 | CTTTCATTTCAGCCGATCATACCTCAATGCAGATAAGCAC | 132 |
| 48 | 0.000466509 | CTTTCATTTCAGCCGATCATACCTCAATACAGATAAGCAC | 133 |
| 49 | 0.000465203 | AACGGTTGCTTTCATAAGAGTGATGCCGATTCATTTCCAC | 134 |
| 50 | 0.000446908 | CTTTCATTTCAGCCGATCATACCCCAATATAGATAAGCAC | 135 |
| 51 | 0.000424693 | AACGGTTGCTCTCATAAGAGTGATGCCGATTCATCTCCAC | 136 |
| 52 | 0.000420773 | AACGGTTGCCCTCACAAGAGTGATGCCGATTCATTTCCAC | 137 |
| 53 | 0.000420773 | CTTTCATTTCAGCCGATTATACCTCAATATAGACAAGCAC | 138 |
| 54 | 0.000412933 | CTTTCATTTCAGCCGATCATACCTTAATGTAGATAAGCAC | 139 |
| 55 | 0.000401172 | CACGGTTGCTCTCATAAGAGTGATGCCGATTCATTTCCAC | 140 |
| 56 | 0.000397252 | AACGGTTGCTCTCACAAGAGTGATGCCGATTCATTTCCAC | 141 |
| 57 | 0.000382877 | CCTTCATTTCAGCCGATCATACCTCAATGTAGATAAGCAC | 142 |
| 58 | 0.000372423 | TACGGTTGCTCTCATAAGAGTGATGCCGATTCATTTCCAC | 143 |
| 59 | 0.000368503 | CTTTCATTTCAGCCGATTATACCCCAATATAGATAAGCAC | 144 |
| 60 | 0.000355436 | CTTTCATTTCAGCCGATCATTCCTCAATGTAGATAAGCAC | 145 |
| 61 | 0.000346288 | AACGGTTGCTCCCATAAGGGTGATGCCGATTCATTTCCAC | 146 |

TABLE 2-continued

Top 100 Sequences from the 11th Round of Selection

| Rank | Frequency | Sequence | SEQ ID NO: |
|---|---|---|---|
| 62 | 0.000346288 | AACGGTTGCTCTCATAAGAGTGGTGCCGATTCATTTCCAC | 147 |
| 63 | 0.000338448 | AGCAACTGGGACAGATCGACAGCCTCTCATTTCAAGTCAC | 148 |
| 64 | 0.000333221 | AACGGTTGCTCTCATAGGAGTGATGCCGATTCATTTCCAC | 149 |
| 65 | 0.000331914 | AACGGTTGCTCTCATAAGAGTGACGCCGATTCATTTCCAC | 150 |
| 66 | 0.000329301 | AACGGCTGCTCTCATAAGAGTGATGCCGATTCATTTCCAC | 151 |
| 67 | 0.000327994 | AGCAACTGGGACAGATCGACAGCCTTTCACTTCAAGTCAC | 152 |
| 68 | 0.000322767 | CTCTCATTTCAGCCGATCATACCTCAATGTAGATAAGCAC | 153 |
| 69 | 0.00032146 | AGCAACTGGGGCAGATCGACAGCCTTTCATTTCAAGTCAC | 154 |
| 70 | 0.00032146 | AGCAACTGGGACAGATCGACAGCCTTTCATTTCAAGTCGC | 155 |
| 71 | 0.00031754 | AGCAACTGGGACAGATCGACAGCCTTTCATCTCAAGTCAC | 156 |
| 72 | 0.000309699 | AGAAACTGGGACAGATCGACAGCCTTTCATTTCAAGCCAC | 157 |
| 73 | 0.000303166 | AACGGTTGCTCTCATAAGAGTGATGCCGACTCATTTCCAC | 158 |
| 74 | 0.000297939 | CTTTCATTTCAGCCGATCATACCTCGATGTAGATAAGCAC | 159 |
| 75 | 0.000296632 | CTTTCACTTCAGCCGATCATACCTCAATGTAGATAAGCAC | 160 |
| 76 | 0.000295325 | AACGGTTGCTCTCATAAGAGTGATGCCGATTCATTTCCGC | 161 |
| 77 | 0.000291405 | AACAACTGGGACAGATCGACAGCCTTTCATTTCAAGTCAC | 162 |
| 78 | 0.000291405 | AGCAACTGGGACAGATCGACAGCCCTTCATTTCAAGTCAC | 163 |
| 79 | 0.000288791 | CTTTCATTTCAGCCGATCATACCTCAGTGTAGATAAGCAC | 164 |
| 80 | 0.000284871 | CTTTCATTTCGGCCGATCATACCTCAATGTAGATAAGCAC | 165 |
| 81 | 0.000280951 | AACGGTTGCTCTCACAAGAGTGACGCCGATTCATTTCCAC | 166 |
| 82 | 0.000275724 | AGCAACTGGGACAGATCGACAGCCTTTCATTTCGAGTCAC | 167 |
| 83 | 0.000274417 | CTTTCATTTCAGCCGATCATACCACAATGTAGATAAGCAC | 168 |
| 84 | 0.000273111 | AACGGTTGCTTCCATAAGAGTGATGCCGATTCATTTCCAC | 169 |
| 85 | 0.00026919 | GACGGTTGCCCTCATAAGAGTGATGCCGATTCATTTCCAC | 170 |
| 86 | 0.000267884 | CACCCCTCGGATCTTCTTCTTTATTAGATTCATTTCAGAG | 171 |
| 87 | 0.000267884 | AACGGTTGCTCTCGTAAGAGTGATGCCGATTCATTTCCAC | 172 |
| 88 | 0.000258736 | AGCAACTGGGACAGATCGGCAGCCTTTCATTTCAAGTCAC | 173 |
| 89 | 0.00025743 | AACGGTTGCTCTCATAAGAGCGATGCCGATTCATTTCCAC | 174 |
| 90 | 0.000256123 | CTTTCATTTCAGCCGATCATATCTCAATGTAGATAAGCAC | 175 |
| 91 | 0.000254816 | AACGGTTGCTCTCATAAGAGTGATGCTGATTCATTTCCAC | 176 |
| 92 | 0.000254816 | AACGGTTGCTCTCATAAGAGTGATGCCGATTCACTTCCAC | 177 |
| 93 | 0.000253509 | CCCTGGCATTGCAAGGTTGATTCTCCGATCATTTTCACAC | 178 |
| 94 | 0.000252203 | AACGGTTGTTCCCATAAGAGTGATGCCGATTCATTTCCAC | 179 |
| 95 | 0.000249589 | AGCAACTGGGACGGATCGACAGCCTTTCATTTCAAGTCAC | 180 |
| 96 | 0.000248282 | CTTCCATTTCAGCCGATCATACCTCAATGTAGATAAGCAC | 181 |
| 97 | 0.000243055 | CTTTCATTTCAGCCGATCGTACCTCAATGTAGATAAGCAC | 182 |
| 98 | 0.000241749 | AACGGTTGCTCTCATAAGAGTGATGCCGATTCATTCCCAC | 183 |

TABLE 2-continued

| Top 100 Sequences from the $11^{th}$ Round of Selection | | | |
|---|---|---|---|
| Rank | Frequency | Sequence | SEQ ID NO: |
| 99 | 0.000241749 | CTTTCATTTCAGCCGATCATACCTCAACGTAGATAAGCAC | 184 |
| 100 | 0.000239135 | AGCAACTGGGACAGGTCGACAGCCTTTCATTTCAAGTCAC | 185 |

Table 2 shows the top 100 sequences from the $11^{th}$ round in an exemplary embodiment of the disclosure. After 11 rounds of selection, the DNA pool was sequenced, and the top 100 sequences ranked. Total reads defined as the number of sequence reads passing sequence processing, namely primer trimming, pair-end merging and perfect complementarity in the random domain. Frequency is defined as the fraction of total reads represented by a unique sequence.

Figure 3A:
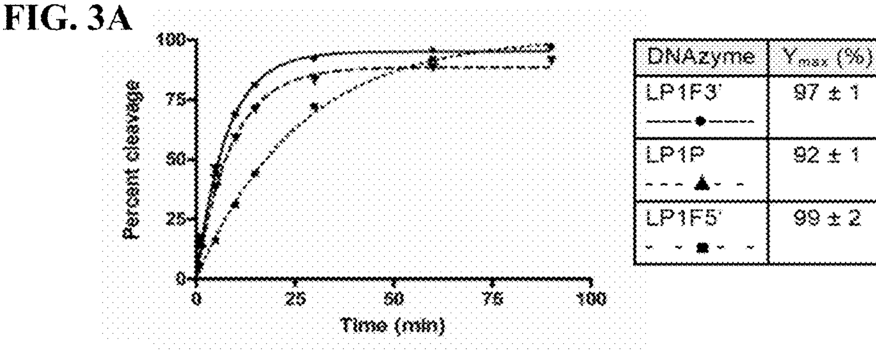
FIG. 3A shows the impact of removing the F and Q modifications on the catalytic activity of LP1 in an exemplary embodiment of the disclosure.
Figure 3B:
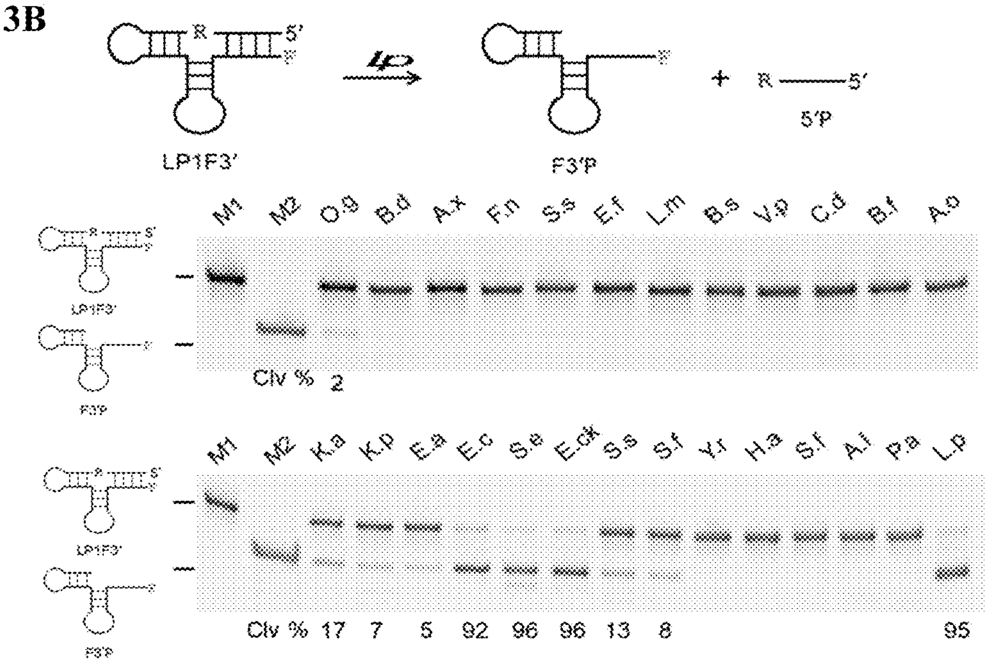
FIG. 3B shows the impact of removing the F and Q modifications on the catalytic activity of LP1 in an exemplary embodiment of the disclosure.
Figure 3C:
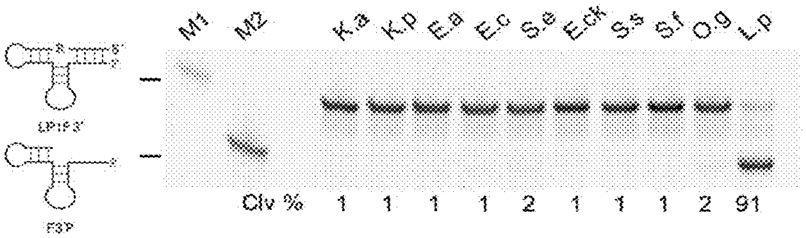
FIG. 3C shows the impact of removing the F and Q modifications on the catalytic activity of LP1 in an exemplary embodiment of the disclosure.

Removal of F and Q improves the activity of LP1: It was next determined whether or not the presence of the F and Q modifications affected the catalytic activity of LP1. To investigate this question, the original F and Q modifications present on LP1FQ were removed. Three new versions of LP1 were produced, which were named LP1P, LP1F3' and LP1F5', and contained 32P-labelled 5'-phosphate, 3'-fluorescein and 5'-fluorescein, respectively. The kinetic analysis of LP1P, LP1F3' and LP1F5' revealed a respective $k_{obs}$ of 0.103, 0.125, 0.040 min' (FIG. 3A). Interestingly, removal of the original F and Q modifications resulted in much more efficient DNAzyme constructs with ~12-40-fold rate enhancements. This finding indicates that the presence of the F and Q near the cleavage site had a significant effect on the catalytic activity of LP1FQ. It should be noted that previous studies with other RFDs have not examined the effect of removal of the F and Q on kinetics. Since the observed difference in the apparent rates was minimal, investigations were continued with LP1F3' as it was determined to have the highest rate and avoided the use of radioactivity. The LP1F3' construct was then investigated for specificity towards the 26 bacterial species previously assessed for LP1FQ. Intriguingly, a marked difference in selectivity was observed for LP1F3' (FIG. 3B). Following a 1-h incubation at room temperature with the CEM of all 26 bacteria, LP1F3' was cleaved by 10 species within 6 different genus of proteobacteria including: *Legionella pneumophila* (L.p; 95%), *Escherichia coli* K12 (E.ck; 96%), *Salmonella enterica* (S.e; 96%), *Enterobacter cloacae* (E.c; 92%), *Klebsiella aerogenes* (K.a; 17%), *Shigella sonnei* (S.s; 13%), *Shigella flexneri* (S.f; 8%) *Klebsiella pneumoniae* (K.p; 7%), *Enterobacter aerogenes* (E.a; 5%), and *Ochrobactrum grignonense* (O.g; 2%). Previously an RFD was discovered (RFA13-1) which was activated by Rnase I from several proteobacteria including those listed above, with the exception of *Legionella pneumophila* (not tested) and *O. gringonese* (no activity observed).[28] Therefore, the non-specific cleavage of LP1F3' observed was most likely due to the presence of RNase, and sought to evaluate the specificity of LP1F3' in the presence of RNase inhibitors that suppress the activity of RNases (A, B, C, I, and T1). By process of elimination, it was found that RNase I is likely responsible for the non-specific cleavage activity exhibited by LP1F3', given that non-specific cleavage was observed in the presence of an RNase A, B and C inhibitor (NxGen Rnase inhibitor), but not observed when an RNase A, B, C, I and T1 inhibitor (SUPERase-in Rnase inhibitor) was used (FIG. 3C). Since RNase T1 is a fungal ribonuclease that is not expressed by bacteria, it cannot be responsible for inducing the observed non-specific cleavage, leaving RNase I as the most likely cause. The conclusion that RNase I is likely responsible for the observed non-specific cleavage activity is the same conclusion made by the authors for the observed non-specific cleavage activity of RFA13-1.[28] Furthermore, RNase I protein sequences corresponding to the 8 bacterial species listed previously that were capable of inducing cleavage share high sequence identity.[28] These species express similar RNase I that can both non-specifically cleave LP1F3' and be inhibited by the addition of the SUPERase-in Rnase inhibitor.

Figure 13:
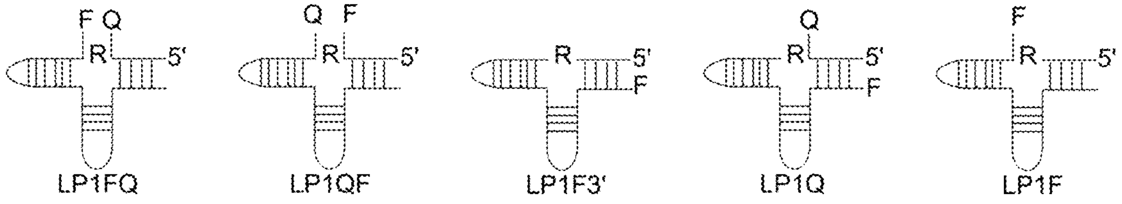
FIG. 13 shows RNA-cleaving activity of five DNAzyme constructs with varying F and Q modifications against selected bacteria in an exemplary embodiment of the disclosure. Each construct was incubated with the crude extracellular mixture (CEM) prepared from 9 different bacteria for 1 hour, followed by dPAGE analysis of the cleavage mixture. Cleavage activity is coded as follows: black boxes (90-100%), white boxes with bolded values (80-89%), light grey boxes (50-79%), dark grey boxes (20-49%), white boxes with underlined values (10-19%), and white boxes with diagonal line (0-9%).

A possible challenge posed by the selection of RFDs using modified oligonucleotides is the dependency of the cleavage activity on the modifications. To elucidate whether or not there was an effect on LP1, the F and Q modifications were partially or fully removed the selectivity of the sequence was assessed (FIG. 13). From these data it was concluded that the high specificity of LP1FQ towards CEM-LP is likely due to the presence of the internal F and Q, given that their removal results in the non-specific cleavage activity seen in LP1F3' in the absence of the RNase I inhibitor. In this case there are two types of cleavage occurring, target induced cleavage, and non-specific cleavage, caused by Rnase I. The fluorescein and dabcyl are bulky molecules that could sterically hinder access to the ribonucleotide. This potential steric hindrance seems to be beneficial for specificity, as demonstrated by the fact that LP1FQ is unaffected by non-specific cleavage. However, the apparent cleavage rate of LP1FQ is much lower, indicating that access to the ribonucleotide by the *Legionella pneumophila* target can also be sterically hindered. Though the specificity is high, the rate is compromised. Removal of the F and Q results in a cleavage rate 40-fold greater, indicating that the *Legionella pneumophila* target can readily access the ribonucleotide and induce cleavage, making the singly labeled LP1, along with the use of the SUPERase-In Rnase inhibitor, much more practical for use in biosensing.

Figure 4A:
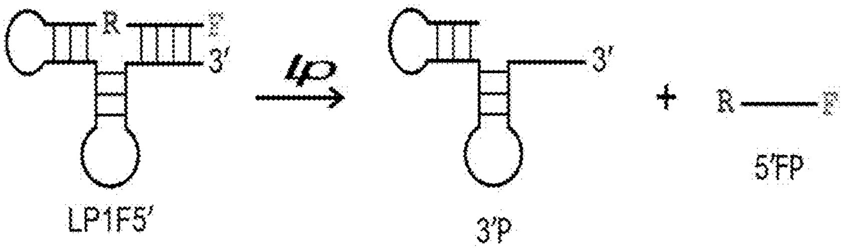
FIG. 4A shows the assessment of species and strain specificity of LP1 in an exemplary embodiment of the disclosure.
Figure 4B:
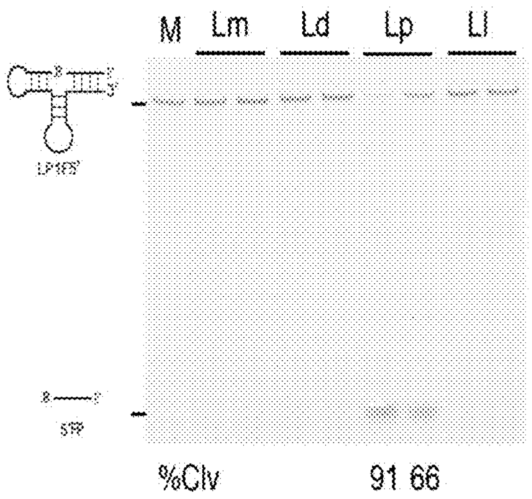
FIG. 4B shows the assessment of species and strain specificity of LP1 in an exemplary embodiment of the disclosure.
Figure 14:
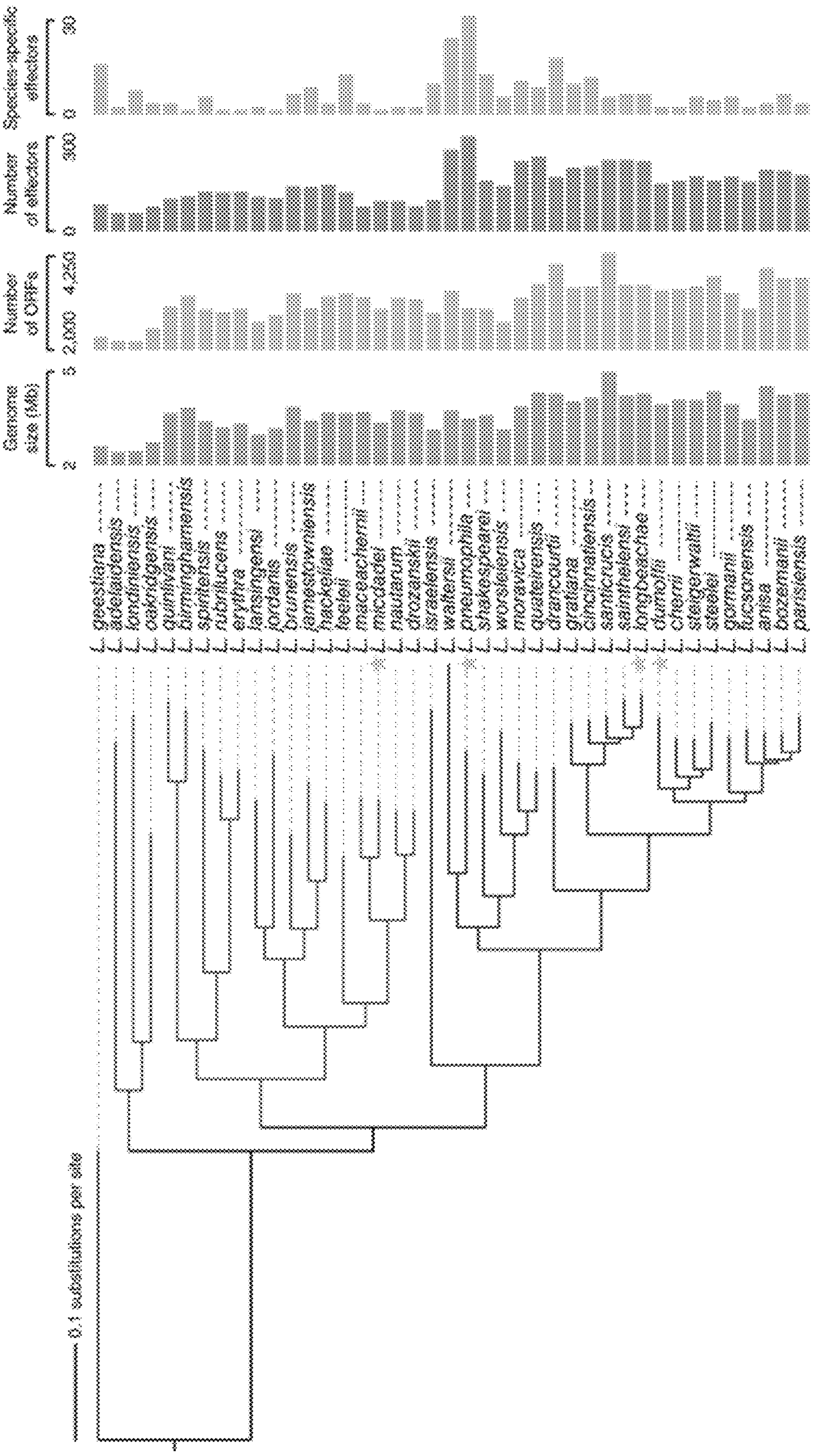
FIG. 14 shows the phylogenetic tree of the *Legionella* genus in an exemplary embodiment of the disclosure. Reproduced from Burstein, D., Amaro, F., Zusman, T., Lifshitz, Z., Cohen, O. Gilbert J. A., Pupko, T., Shuman, H. A., and Segal, G. Genomic analysis of 38 *Legionella* species identifies large and diverse effector repertoires. Nature Genetics 48, 167-175 (2016) which is under a Creative Commons Attribution-NonCommercial ShareAlike 3.0

DNAzyme target likely specific to *Legionella pneumophila*: Although all *Legionella* species have the potential to be pathogenic, *Legionella pneumophila* is responsible for the large majority of cases of Legionnaires' disease. [7, 29, 30] Encouraged by the high selectivity demonstrated by the previously reported DNAzymes for *Clostridium difficile* and *Vibrio anguillarum*,[31, 32] the specificity of LP1 towards other *Legionella* species was investigated. LP1F5' was used for these experiments. The following *Legionella* species were examined: *Legionella micdadei*, *Legionella dumofii*, and *Legionella longbeachae* (FIG. 14). After a 1-h incubation at room temperature, LP1F5' was only cleaved in the presence of *Legionella pneumophila* but not by the other three *Legionella* species (FIG. 4A and FIG. 4B).

Figure 4C:
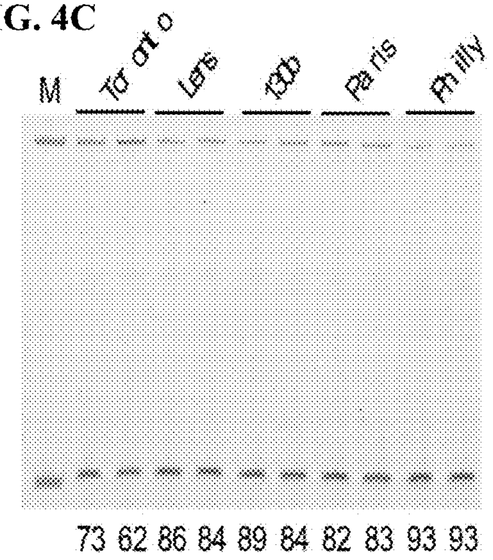
FIG. 4C shows the assessment of species and strain specificity of LP1 in an exemplary embodiment of the disclosure.

The specificity of the DNAzyme towards several *Legionella pneumophila* strains was tested which included Toronto-2005, Lens, 130b, and Paris, that are phylogenetically distant from the Philadelphia strain (FIG. 15) used in all experiments described above. After a 1-h incubation at room temperature, LP1F5' was cleaved by all the strains investigated (FIG. 4C). These findings indicate that LP1 is highly selective for *Legionella pneumophila* species yet is responsive to all *Legionella pneumophila* strains evaluated, a necessary characteristic for the detection of *Legionella pneumophila* in cooling towers world-wide.

Figure 5:
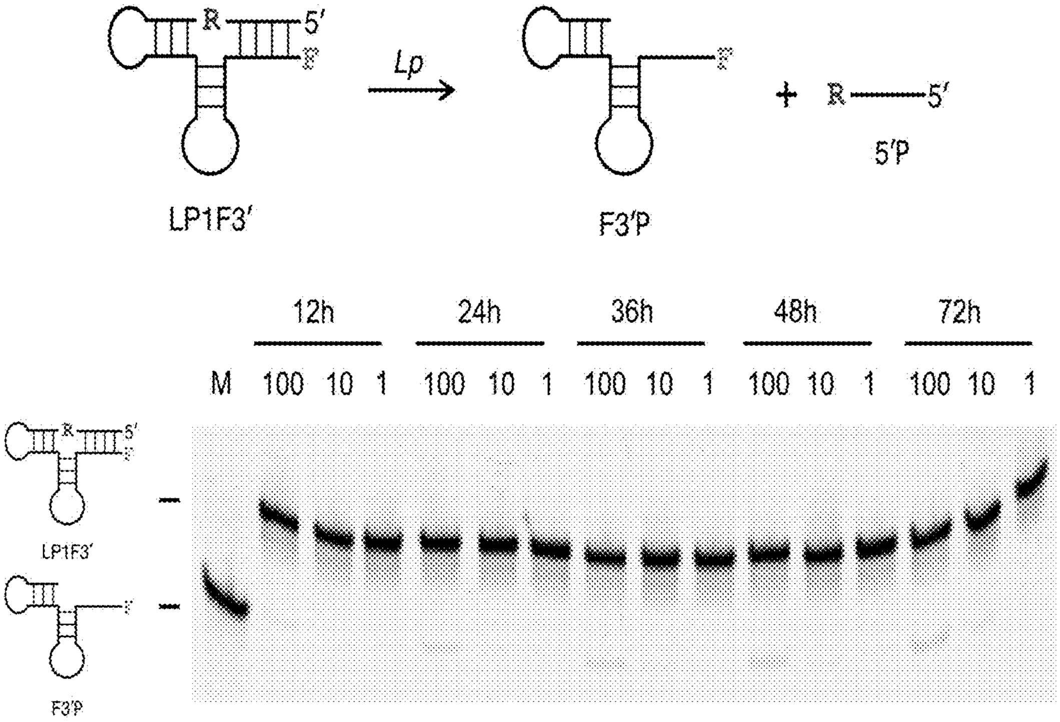
FIG. 5 shows the sensitivity of LP1 via dPAGE analysis using LP1F3' in an exemplary embodiment of the disclosure. LP1F3' is capable of detecting ~10 CFUs after 72-h incubation. LP1F3' was incubated with 100, 10, or 1 CFU of *Legionella pneumophila* (the Philadelphia strain) for various timepoints: 12, 24, 36, 48, 72 h, after which the RNA-cleaving activity of LP1F3' was determined by dPAGE. M: the fluorophore-carrying cleavage product F3'P. After a 72-h incubation with *Legionella pneumophila* at a concentration of 10 CFU/μL a cleavage band was seen. The dash left to the gel indicates the location of the uncleaved LP1F3' (top) and the cleaved fragment F3'P (bottom) within the gel.

LP1F3' can detect 10 CFU using gel-based method: The sensitivity of LP1 via dPAGE analysis using LP1F3' was next determined (FIG. 5). The DNAzyme was incubated with CEM-LP prepared from varying numbers of cells for various time points. At high CEM-LP levels (prepared from $10^4$-$10^6$ CFUs in 1 mL volume), the cleavage activity can be detected within 1 h (FIG. 16). After 12 h, the cleavage of LP1F3' was observed with 100 CFUs. When the reaction time was extended to 72 h, the cleavage activity was seen with 10 CFUs. It is important to note that no detectable cleavage was observed for LP1F3' upon 72-h incubation with reaction buffer only (FIG. 17). These results indicate LP1 exhibits a very high level of sensitivity and is able to produce a signal in response to as few as 10 *Legionella pneumophila* CFUs.

Figure 6A:
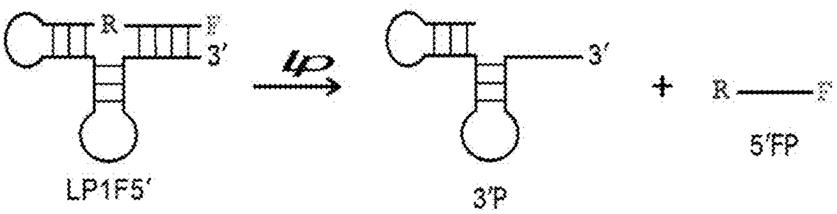
FIG. 6A shows assessment of the target that activates LP1 in an exemplary embodiment of the disclosure.
Figure 6B:
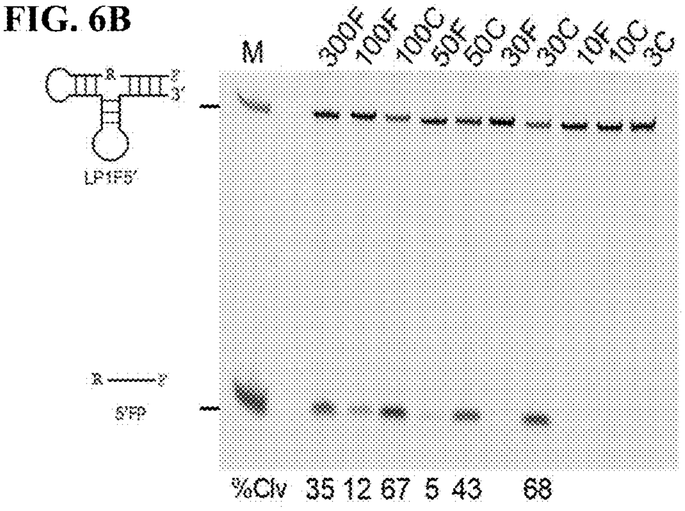
FIG. 6B shows assessment of the target that activates LP1 in an exemplary embodiment of the disclosure.

The activating target is likely a 30-100 kDa protein: LP1 was selected using the CEM produced by *Legionella pneumophila* and therefore the activating target for LP1 is unknown but it is found both inside and outside the bacteria cell. However, some knowledge on this target can be advantageous in future assay optimization and biosensor design. As an investigation into the LP1 target, the activity of the DNAzyme against CEM-LP fractionated by molecular weight was investigated. Briefly, CEM-LP was successively passed through centrifugal filters with molecular weight cut-offs from 300 kDa to 3 kDa. After centrifugation with each membrane size, a sample of both the filtrate and concentrate were collected and tested for cleavage activity. LP1F5' was used for this experiment (FIG. 6A). After a 1-h incubation at room temperature, cleavage of LP1F5' was observed in samples collected in the 30-100 kDa range (FIG. 6B).

Figure 6C:
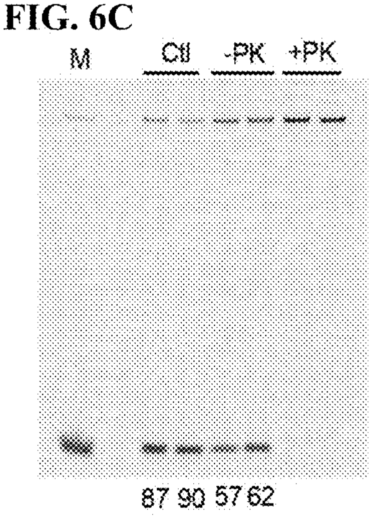
FIG. 6C shows assessment of the target that activates LP1 in an exemplary embodiment of the disclosure.
Figure 8:
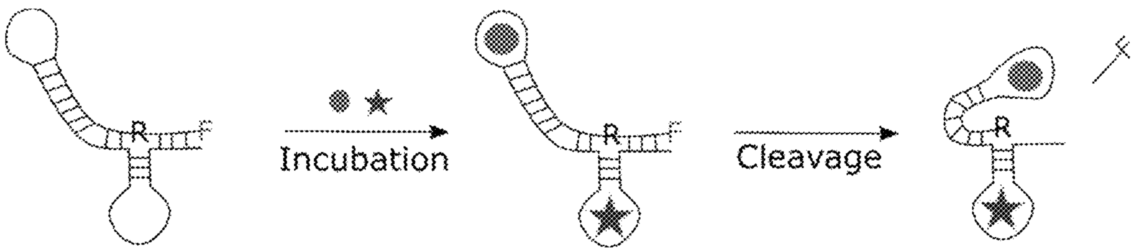
FIG. 8 shows a schematic representation of DNAzyme cleavage in the presence of a bacterial target in an exemplary embodiment of the disclosure. In this scheme, the intact DNAzyme is shown on the left, where R represents the RNA cleavage site, and F represents the reporter fluorophore. Prior to cleavage, the DNAzyme is then incubated with the crude extracellular mixture (CEM) of the target bacteria. Since the DNAzyme is specifically activated in the presence of the bacterial target, in this case *Legionella pneumophila*, the DNAzyme likely has an aptamer region (shown in the middle panel) that recognizes that specific target (shown as a solid sphere) and perhaps facilitates site specific cleavage. Given the known mechanisms of RNA-cleaving DNAzyme catalysis, it is likely that a cofactor molecule, perhaps a metal ion such as Mg' included in the selection buffer, is also required for efficient enzymatic activity. [12] The cofactor is represented by the star, and the cofactor region is shown in the middle panel. The exact mechanism of catalysis of RNA-cleaving DNAzymes for bacterial targets is unknown, since many of the specific targets are unknown. Without wishing to be bound by theory, it is conceptualized that binding of the target, or target and cofactor, facilitates a structural change, which improves access to the cleavage site, or somehow brings the catalytic region close enough to the cleavage site.

Given the size range of the target, and the propensity for functional nucleic acids to interact with protein targets, the activity of LP1 was investigated after the CEM-LP had been heated to 90° C., as well as in the presence of proteinase K. The first indication that the LP1 target was a protein was the drastically decreased activity observed after the CEM-LP was heated to 90° C. for as little as 1 min (FIG. 18). The second indication came from Proteinase K treatment. Briefly, CEM-LP was treated with Proteinase K (1 mg/mL) overnight, followed by incubation with LP1F5' at room temperature for 1 h (FIG. 6C). No cleavage was observed with the addition of Proteinase K and an overnight incubation at 37° C., indicating that the target is likely a protein.

LP1 maintains its activity in cooling tower water: All characterization experiments were conducted in buffered clean reaction solutions that are not representative of real-world environmental samples. It was important to determine if the DNAzyme could function in cooling tower water, given the proposed disclosure of LP1 for *Legionella pneumophila* detection. Contrary to clean reaction solutions made of deionized water and other pure reagents, cooling tower water can contain a variety of potential interferents including bacteria, metal ions, and chemical reagents used for water treatment. Therefore, the DNAzyme activity under more practical conditions was evaluated. The first assessment focused on the activity of the DNAzyme in deionized water or CEM-LP without selection buffer (FIG. 19). This assay revealed that the cleavage activity was absent in water and much reduced in CEM-LP without selection buffer. This is not surprising given the tendency of DNAzyme activity to be metal-ion dependent. The cleavage activity of LP1F5' in the presence of water treatment reagents was then assessed (FIG. 20). Importantly, LP1F5' was still active in the presence of CEM-LP. Subsequently, the activity of LP1F5' was assessed in Fraquil, a freshwater medium which mimics cooling tower water (FIG. 21). Briefly, bacteria were subcultured into the Fraquil media and incubated at room temperature for 24 h. The subculture was then incubated with LP1F5' for 1 h at room temperature, after which cleavage was observed using dPAGE.

Finally, the ability of LP1F5' to maintain its RNA-cleaving activity in actual cooling tower water, was assessed (FIG. 7). After a 1-h incubation at room temperature with over 50 independent cooling tower water samples collected from multiple geographic locations (where the water made up 80% final reaction volume), LP1F5' demonstrated no cleavage activity in cooling tower water absent of spiked CEM-LP (FIG. 7C). After a 1-h incubation at room temperature with the same cooling tower water samples (where the water made up 50% final volume), that had been spiked with CEM-LP, LP1F5' was cleaved in all samples. Over 50 different cooling tower water samples from Canada and the USA were tested, the locations and number of samples from each location are summarized in FIG. 7B. Detailed sample information is summarized in Table 3. Collectively, these data indicate that LP1 is stable and its activity is maintained in cooling tower water.

TABLE 3

Location and percent cleavage of all cooling tower water samples tested, in duplicate, with LP1F5'.

| Location | Cooling tower water sample | % Clv |
|---|---|---|
| Quebec | 1 | 76 |
| Quebec | 1 | 83 |
| Quebec | 2 | 98 |
| Quebec | 2 | 98 |
| Quebec | 3 | 72 |
| Quebec | 3 | 85 |
| Quebec | 4 | 87 |
| Quebec | 4 | 88 |
| Pennsylvania | 5 | 74 |
| Pennsylvania | 5 | 87 |
| Pennsylvania | 6 | 89 |
| Pennsylvania | 6 | 89 |
| Pennsylvania | 7 | 82 |
| Pennsylvania | 7 | 87 |
| Pennsylvania | 8 | 86 |
| Pennsylvania | 8 | 88 |
| Pennsylvania | 9 | 89 |
| Pennsylvania | 9 | 76 |
| Pennsylvania | 10 | 83 |
| Pennsylvania | 10 | 86 |
| Pennsylvania | 11 | 83 |
| Pennsylvania | 11 | 84 |
| Ohio | 12 | 84 |
| Ohio | 12 | 79 |
| Quebec | 13 | 85 |
| Quebec | 13 | 89 |
| Quebec | 14 | 93 |
| Quebec | 14 | 92 |
| Quebec | 15 | 100 |
| Quebec | 15 | 100 |
| Quebec | 16 | 93 |
| Quebec | 16 | 92 |
| Quebec | 17 | 93 |
| Quebec | 17 | 91 |
| Quebec | 18 | 94 |
| Quebec | 18 | 99 |
| Quebec | 19 | 92 |

TABLE 3-continued

Location and percent cleavage of all cooling tower
water samples tested, in duplicate, with LP1F5'.

| Location | Cooling tower water sample | % Clv |
|---|---|---|
| Quebec | 19 | 92 |
| Quebec | 20 | 98 |
| Quebec | 20 | 98 |
| Quebec | 21 | 97 |
| Quebec | 21 | 98 |
| Quebec | 22 | 98 |
| Quebec | 22 | 51 |
| Quebec | 23 | 88 |
| Quebec | 23 | 98 |
| Quebec | 24 | 45 |
| Quebec | 24 | 99 |
| Quebec | 25 | 95 |
| Quebec | 25 | 91 |
| Quebec | 26 | 100 |
| Quebec | 26 | 100 |
| Quebec | 27 | 63 |
| Quebec | 27 | 72 |
| Pennsylvania | 28 | 86 |
| Pennsylvania | 28 | 90 |
| Pennsylvania | 29 | 60 |
| Pennsylvania | 29 | 72 |
| Pennsylvania | 30 | 86 |
| Pennsylvania | 30 | 82 |
| Pennsylvania | 31 | 79 |
| Pennsylvania | 31 | 85 |
| Pennsylvania | 32 | 83 |
| Pennsylvania | 32 | 84 |
| Pennsylvania | 33 | 82 |
| Pennsylvania | 33 | 83 |
| Pennsylvania | 34 | 84 |
| Pennsylvania | 34 | 83 |
| Pennsylvania | 35 | 81 |
| Pennsylvania | 35 | 82 |
| Pennsylvania | 36 | 83 |
| Pennsylvania | 36 | 86 |
| Pennsylvania | 37 | 37 |
| Pennsylvania | 37 | 44 |
| Pennsylvania | 38 | 80 |
| Pennsylvania | 38 | 76 |
| Pennsylvania | 39 | 78 |
| Pennsylvania | 39 | 79 |
| Pennsylvania | 40 | 58 |
| Pennsylvania | 40 | 63 |
| Pennsylvania | 41 | 81 |
| Pennsylvania | 41 | 79 |
| New Jersey | 42 | 92 |
| New Jersey | 42 | 92 |
| Pennsylvania | 43 | 91 |
| Pennsylvania | 43 | 96 |
| Pennsylvania | 44 | 88 |
| Pennsylvania | 44 | 90 |
| Pennsylvania | 45 | 91 |
| Pennsylvania | 45 | 92 |
| Pennsylvania | 46 | 87 |
| Pennsylvania | 46 | 96 |
| Quebec | 47 | 91 |
| Quebec | 47 | 89 |
| Quebec | 48 | 98 |
| Quebec | 48 | 93 |
| Quebec | 49 | 79 |
| Quebec | 49 | 96 |
| Pennsylvania | 50 | 79 |
| Pennsylvania | 50 | 86 |
| Pennsylvania | 51 | 82 |
| Pennsylvania | 51 | 86 |
| Pennsylvania | 52 | 96 |
| Pennsylvania | 52 | 94 |
| Pennsylvania | 53 | 89 |
| Pennsylvania | 53 | 88 |
| Pennsylvania | 54 | 87 |
| Pennsylvania | 54 | 89 |
| Pennsylvania | 55 | 89 |
| Pennsylvania | 55 | 89 |
| Pennsylvania | 56 | 88 |
| Pennsylvania | 56 | 89 |

TABLE 3-continued

Location and percent cleavage of all cooling tower
water samples tested, in duplicate, with LP1F5'.

| Location | Cooling tower water sample | % Clv |
|---|---|---|
| Pennsylvania | 57 | 94 |
| Pennsylvania | 57 | 95 |

Each cooling tower water sample was subjected to a total of four cleavage tests with LP1F5'. The cooling tower water sample was either spiked with CEM-LP (positive) or not spiked with CEM-LP (negative) and tested in duplicate. Additionally, controls for each day of testing were prepared to ensure proper functioning of LP1F5' (details in methods). No cleavage activity was observed in the negative tests for any of the cooling tower water samples. Cleavage activity of LP1F5' in the positive tests for all cooling tower water samples is highlighted in the table along with corresponding cooling tower location.

Currently, bacterial levels in water sources are often monitored as total bacteria counts (via ATP assays), and specific regulation towards *Legionella pneumophila* detection is lacking.[33] The current 'gold standard' for *Legionella pneumophila* detection in water systems recommended by Public Health agencies around the world is bacterial culturing; however, this method is technically challenging and can take up to 10 days to confirm contamination. [8] This delay between sample collection and subsequent *Legionella* detection creates an opportunity for a Legionnaires disease outbreak to occur. Advancements in PCR-based detection methods have decreased detection time but are not without their own challenges. Sample preparation for PCR often requires several steps and the method itself can be inhibited by the components of real-world samples. [8]

Identifying a DNAzyme that is specific for *Legionella pneumophila* but inactive with other common bacteria, provides an important building block upon which more sensitive, and practically applicable detection platforms can be assembled, addressing the resource limited challenges of on-site cooling tower water monitoring.

Via in vitro selection, for the first time, a DNAzyme that is activated by *Legionella pneumophila* was successfully isolated, an important deadly waterborne pathogen. Extensive characterization work has revealed that the DNAzyme is highly specific for *Legionella pneumophila* and that the cleavage rate can be improved 40-fold when the internal F and Q modifications are removed. Loss of specificity as a consequence of the internal F and Q modification removal can be rescued with the addition of RNase inhibitors. This important observation offers researchers a practical strategy to address the challenges of non-specific degradation of RNA-cleaving DNAzymes in biosensing assays. Investigations into the target that activates the DNAzyme indicate that it is a protein between 30-100 kDa in size. The DNAzyme is highly sensitive and can detect as few as 10 CFU without amplification, a level of sensitivity not previously demonstrated with DNAzymes for other bacteria. Finally, the DNAzyme maintains its activity in cooling tower water without any manipulation of the samples. The DNAzymes are useful for incorporation in a simple, user-friendly biosensor for the on-site detection of *Legionella pneumophila* in cooling tower water.

Previously, RFDs selected to recognize a specific bacterium can be immediately translated into a fluorescent sensor due to their inherent quenching and dequenching modality. [27, 31] The reduced catalytic activity of LP1FQ is not favourable for direct translation to rapid fluorescent detection. However, a variety of signal production mechanisms have been devised specifically for RNA-cleaving DNAzymes. [34, 35] It is conceivable that some of these strategies can be used to convert the *Legionella pneumophila*-specific DNAzyme into a rapid and sensitive sensing system for on-site detection of *Legionella pneumophila* in cooling tower water. In fact, the efficiency of these approaches has been demonstrated by the commercial success of RNA-cleaving DNAzyme based testing platforms for water quality testing (ANDzyme and Urasensor for bacterial detection from InnovoGENE Biosciences; metal ion detection by ANDalyze). The bottleneck in DNAzyme based detection is the selection and characterization of a highly functional DNAzyme that works in the anticipated detection matrix. Some key challenges that researchers should consider in the selection of these reporter molecules and their translation to commercial detection platforms include the complexity of the detection matrix (environmental water samples, biological fluids, etc), intrinsic fluorescence of the target, pre-treatment and concentration of the sample, practical testing conditions, and testing storage. Considering these challenges at the selection stage can help ensure successful translation of the DNAzyme to an onsite testing device.

Example 3. Rational Truncation of an RNA-Cleaving DNAzyme by Reselection and Mutational Analysis The previously selected LP1 sequence was challenged to identify higher activity candidates and to elucidate a punitive secondary structure. The combination of these methods previously allowed Li and colleagues to improve the kinetics of a weakly catalytic RNA-cleaving DNAzyme sequence, G2501, by 500-fold following only a few mutations of the parent sequence to produce the mutant RF1.E1. [36] Recently, similar methods were applied to identify an RNA-cleaving DNAzyme which was active in the presence of $Ag^+$, that showed an ~200% increase in activity over the original DNAzyme. [37] Likewise, a mutant RNA-cleaving DNAzyme activated by Ca' was identified that showed improved catalytic activity, and an ~20-fold increase in selectivity compared to the parent sequence.[38] Reselection and mutational analysis had not been reported for an RNA-cleaving DNAzyme activated by a bacterial target.

Briefly, the LP1 sequence identified previously was selected against the crude extracellular mixture (CEM) derived from *Legionella pneumophila*. The 112-nucleotide sequence demonstrated efficient kinetic activity with a reported $K_{obs}$ of 0.125±0.005 min-1, and excellent selectivity in the presence of 25 other common bacteria and 3 other *Legionella* species. Interestingly, analyses of the highest ranked sequences of the enriched selection libraries revealed that a large portion of the 3'-primer region was likely involved in sequence secondary structure and activity. Therefore, the LP1 sequence was investigated by performing a reselection and mutational analysis using the most promising sequence from the original selection, with slight modifications (the random region was extended by 16 nucleotides), and an applied 30% mutation rate per nucleotide of the random region (FIG. 22).

Like the initial selection, the reselection included negative selections against buffered yeast extract, and CEM from both *Pseudomonas aeruginosa* and *Klebsiella pneumoniae*. A total of 10 selection rounds were completed. To challenge the library and increase stringency, the incubation time was decreased from 18 hours to 1 hour at round 2, then 30 min at round 6, whereas the negative selection rounds were kept consistent at 18 h. Additionally, the CEM mixtures for positive and negative selections were concentrated by a factor of 4 to increase the target concentration in the selection reaction. A general increasing trend in % cleavage was observed for the positive selection libraries, whereas the % cleavage of the negative selection libraries remained relatively consistent. However, the % cleavage of the $10^{th}$ positive selection library was slightly lower than the $9^{th}$ positive selection library, and so the $9^{th}$ round sequencing data was used for mutational analyses. The top 10 sequences (SEQ ID NOS: 76-85) ranked by round to round enrichment are shown in FIG. 22. Several sequence candidates that represented multiple clusters, or families, were assessed for their catalytic activity compared to that of the selection libraries as controls (FIG. 23A and FIG. 28).

A marked increase in catalytic activity of two (Rank 2 and 4) of the five sequence candidates (Rank 1, 2, 4, 6, and 19) assessed from the positive selection library of the $9^{th}$ round compared to the library activity was observed (FIG. 28). One candidate, Rank 4, demonstrated cleavage that was similar to LP1, and so their kinetics were compared (FIG. 23B). Interestingly, the Rank 4 sequence showed a slightly better $K_{obs}$ of 0.054±0.002 than LP1 (0.040±0.002) when assessed under the same conditions. Given the similar kinetics, the reselection data was used to focus truncation efforts on the LP1 sequence, given its reduced length compared to Rank 4.

Mutational analysis efforts began with several systematic truncations based on the analysis of nucleotide conservation within the top 50 clusters from the positive selection library of round 9 (FIG. 29). There were two distinct domains identified that were highly conserved. The first domain, TTCATTTCAG, was complementary to the substrate region and therefore deemed essential. The middle region AAGCACATCTT (SEQ ID NO: 186) was predicted to form a stem loop structure, where CACAT was in the loop and could potentially interact with the target. Given this information several systematic truncations were evaluated. The first set (T1-T5) focused on deleting 5 nucleotides at a time from the 3' end of the LP1 sequence. As shown in FIG. 24, elimination of these 3' nucleotides drastically decreased the cleavage activity.

The next truncation investigated substitution of the CACAT loop to $polyT_5$. Though the change in activity was not as dramatic as the 3' truncations, these substitutions led to a nearly 50% reduction in activity. Subsequently, the 5' primer region was investigated, to determine its role in catalysis and target binding. It was first determined that a 17-nucleotide region of the 5'-primer domain was non-essential by replacing the nucleotides with polyT17 (See 17TFP in FIG. 24). Since no dramatic effect on cleavage activity was observed, the poly-T region was shortened to polyT9 (9TFP) and polyT4 (4TFP). In both cases the cleavage activity was maintained. All subsequent truncations were performed on the 4TFP sequence. The necessity of a second loop region (FIG. 25, bottom loop with sequence CCTCAA) which was not highly conserved, was assessed as truncation TL1. In this case the 6 nucleotides from the loop were truncated to decrease the sequence length to 93, and the activity was ~76%. The final systematic truncation involved the shortening of the stem of the CACAT loop by 1 (ST1), 2 (ST2), or 3 (ST3) base pairs. Though some cleavage activity was lost compared to the full 112-nt sequence, these 97, 95, and 93 nt sequences demonstrated activity between ~65 and 76%. These truncations allowed the inventors to predict an initial secondary structure, which is shown in FIG. 25.

The top 500 ranked sequences were then examined using multiple sequence alignment to determine the percent nucleotide conservation of each nucleotide. Given that the reselection library had been mutated by 30% per nucleotide, positions conserved at percentages higher than 70% would be essential or advantageous, whereas conservations of 70% or lower would be either non-essential or destabilizing. From this analysis the areas of high conservation were consistent with the cluster analysis. Using these data 13 more truncations were designed (MET1-MET13) that removed various regions that were conserved less than 90%, substituted nucleotides that showed higher conservation, increased polyT length, or added original nucleotides back, yielding truncations ranging in size from 51-101 nucleotides. These are summarized in detail in FIG. 30. The % cleavage values obtained for these sequences ranged from ~4.4-91.4% (see also Table 4). The final set of sequences evaluated were based on MET10 and involved the substitution of specific nucleotides with either T or C to examine the effect of these nucleotides on cleavage activity (Table 4). In each case the activity was drastically reduced from the MET10 sequence. Additionally, the kinetic activities of the full length, and MET10 sequence were compared (FIG. 26A). From these data combined the essential role of the conserved domains predicted from the top 50 clusters of the reselection were confirmed. Further, a 55-nucleotide truncated sequence was identified, that was predicted to form a pseudoknot (FIG. 26C and FIG. 26D).

TABLE 4

All sequences evaluated in this work including length, percent cleavage (% clv), and standard deviation (SD) after 1 h cleavage assays.

| Name | Class | Length | % Clv | SD | Sequence | SEQ ID NO: |
|---|---|---|---|---|---|---|
| LP1F5' | control | 112 | 91.8 | 0.2 | FAM- CTA TGA ACT GAC QTrATF GAC CTC ACT ACC AAG CAA GCA TGG ACA ATA CCG AGC CTT TCA TTT CAG CCG ATC ATA CCT CAA TGT AGA TAA GCA CAT CTT GTC ATC GGA GGC TTA G | 11 |
| 4TFP | Forward primer replaced with poly T | 99 | 95.7 | 0.4 | FAM- CTA TGA ACT GAC TrAT GAC CTC ACT ACC AAG **CT TTT** AGC CTT TCA TTT CAG CCG ATC ATA CCT CAA TGT AGA TAA GCA CAT CTT GTC ATC GGA GGC TTA G | 12 |
| 9TFP | Forward primer replaced with poly T | 104 | 96.5 | 0.4 | FAM- CTA TGA ACT GAC TrAT GAC CTC ACT ACC AAG **CT TTT TTT TT**A GCC TTT CAT TTC AGC CGA TCA TAC CTC AAT GTA GAT AAG CAC ATC TTG TCA TCG GAG GCT TAG | 13 |
| 17TFP | Forward primer replaced with poly T | 112 | 97.2 | 0.3 | FAM- CTA TGA ACT GAC TrAT GAC CTC ACT ACC AAG **CT TTT TTT TTT TTT TTT T**AG CCT TTC ATT TCA GCC GAT CAT ACC TCA ATG TAG ATA AGC ACA TCT TGT CAT CGG AGG CTT AG | 14 |
| T1 | 3'-truncation | 107 | 42.8 | 1.6 | FAM- CTA TGA ACT GAC TrAT GAC CTC ACT ACC AAG CA AGC ATG GAC AAT ACC GAG CCT TTC ATT TCA GCC GAT CAT ACC TCA ATG TAG ATA AGC ACA TCT TGT CAT CGG AGG | 15 |
| T2 | 3'-truncation | 102 | 15.5 | 1.4 | FAM- CTA TGA ACT GAC TrAT GAC CTC ACT ACC AAG CA AGC ATG GAC AAT ACC GAG CCT TTC ATT TCA GCC GAT CAT ACC TCA ATG TAG ATA AGC ACA TCT TGT CAT C | 16 |
| T3 | 3'-truncation | 97 | 14.9 | 1.3 | FAM- CTA TGA ACT GAC TrAT GAC CTC ACT ACC AAG CA AGC ATG GAC AAT ACC GAG CCT TTC ATT TCA GCC GAT CAT ACC TCA ATG TAG ATA AGC ACA TCT TG | 17 |
| T4 | 3'-truncation | 92 | 11.7 | 3.5 | FAM- CTA TGA ACT GAC TrAT GAC CTC ACT ACC AAG CA AGC ATG GAC AAT ACC GAG CCT TTC ATT TCA GCC GAT CAT ACC TCA ATG TAG ATA AGC ACA | 18 |
| T5 | 3'-truncation | 87 | 12.1 | 3.6 | FAM- CTA TGA ACT GAC TrAT GAC CTC ACT ACC AAG CA AGC ATG GAC AAT ACC GAG CCT TTC ATT TCA GCC GAT CAT ACC TCA ATG TAG ATA A | 19 |

TABLE 4-continued

All sequences evaluated in this work including length, percent cleavage (% clv), and standard deviation (SD) after 1 h cleavage assays.

| Name | Class | Length | % Clv | SD | Sequence | SEQ ID NO: |
|---|---|---|---|---|---|---|
| CACAT | Loop replaced with polyT | 112 | 53.1 | 3.1 | FAM- CTA TGA ACT GAC TrAT GAC CTC ACT ACC AAG CA AGC ATG GAC AAT ACC GAG CCT TTC ATT TCA GCC GAT CAT ACC TCA ATG TAG ATA AG**T** **TTT T**CT TGT CAT CGG AGG CTT AG | 20 |
| S1T | Stem truncation | 97 | 67.6 | 1 | FAM- CTA TGA ACT GAC TrAT GAC CTC ACT ACC AAG C**TT TT**A GCC TTT CAT TTC AGC CGA TCA TAC CTC AAT GTA ATA AGC ACA TCT TGT ATC GGA GGC TTA G | 21 |
| S2T | Stem truncation | 95 | 64.6 | 1.1 | FAM- CTA TGA ACT GAC TrAT GAC CTC ACT ACC AAG C**TT TT**A GCC TTT CAT TTC AGC CGA TCA TAC CTC AAT GTA TAA GCA CAT CTT G ATC GGA GGC TTA G | 22 |
| S3T | Stem truncation | 94 | 75.8 | 2.1 | FAM- CTA TGA ACT GAC TrAT GAC CTC ACT ACC AAG C**TT TT**A GCC TTT CAT TTC AGC CGA TCA TAC CTC AAT GTAT AAG CAC ATC TTA TCG GAG GCT TAG | 23 |
| TL1 | Loop truncation | 93 | 76.3 | 0.4 | FAM- CTA TGA ACT GAC TrAT GAC CTC ACT ACC AAG C**TT TT**A GCC TTT CAT TTC AGC CGA TCA TA T GTA GAT AAG CAC ATC TTG TCA TCG GAG GCT TAG | 24 |
| MET1 | % CA | 77 | 44.0 | 3.9 | FAM-CTG ACT rATG ACC TCT TAG CCT TTC ATT TCA GCC GAT CAT ACC TCA ATG TAG ATA AGC ACA TCT TGT CAT CGG AGG CT | 25 |
| MET2 | % CA | 63 | 28.9 | 3 | FAM-CTG ACT rATG ACC TCT TAG CCT TTC ATT TCA GCC GAT GAT AAG CAC ATC TTG TCA TCG GAG GCT | 26 |
| MET3 | % CA | 55 | 4.4 | 0.4 | FAM-CTG ACT rATG ATT TTT CAT TTC AGC CGA TGA TAA GCA CAT CTT GTC ATC GGA GGC T | 27 |
| MET4 | % CA | 55 | 41.7 | 3.3 | FAM-CTG ACT rATG ACC TCT TAG CCT TTC ATT TCA GCC GAA AGC ACA TCT TTC GGA GGC T | 28 |
| MET5 | % CA | 67 | 28.5 | 0.5 | FAM-CTG ACT rATG ACC TCT TAG CCT TTC ATT TCA GCC GAT CGT AGA TAA GCA CAT CTT GTC ATC GGA GGC T | 29 |
| MET6 | % CA | 59 | 67.7 | 1 | FAM-CTG ACT rATG ACC TCT TTT TTA GCC TTT CAT TTC AGC CGA AAG CAC ATC TTT CGG AGG CT | 30 |
| MET7 | % CA | 101 | 91.4 | 0.1 | FAM-CTA TGA ACT GAC TrAT GAC CTC ACT ACC AAG CTT TTT TAG CCT TTC ATT TCA GCC GAT CAT ACC TCA ATG TAG ATA AGC ACA TCT TGT CAT CGG AGG CTT AG | 31 |
| MET8 | % CA | 57 | 51.0 | 0.4 | FAM-CTG ACT rATG ACC TCT TAG CCT TTC ATT TCA GCC GAT AAA GCA CAT CTT TCG GAG GCT | 32 |
| MET9 | % CA | 61 | 60.1 | 1.9 | FAM-CTG ACT rATG ACC TCT TTT TTA GCC TTT CAT TTC AGC CGA TAA AGC ACA TCT TTC GGA GGC T | 33 |
| MET10 | % CA | 55 | 81.7 | 0.1 | FAM-CTG ACT rATG ACC TCT TAG CCC TTC ATT TCA GCC GAA AGC ACA TCT TTC GGG GGC T | 34 |

TABLE 4-continued

All sequences evaluated in this work including length, percent cleavage (% clv), and standard deviation (SD) after 1 h cleavage assays.

| Name | Class | Length | % Clv | SD | Sequence | SEQ ID NO: |
|---|---|---|---|---|---|---|
| MET11 | % CA | 61 | 51.0 | 7.2 | FAM-CTG ACT rATG ACC TCT TCT AAG CCC TTC ATT TCA GCC GAA AGC ACA TCT TTC GGG GGC TTA G | 35 |
| MET12 | % CA | 51 | 57.2 | 0.6 | FAM-CTG ACT rATG ACC TCT TAG CCC TTC ATT TCA GCC AAG CAC ATC TTG GGG GCT | 36 |
| MET13 | % CA | 59 | 41.3 | 2.9 | FAM-CTG ACT rATG ACC TCT TTT TTA GCC CTT CAT TTC AGC CGA AAG CAC ATC TTT CGG GGG CT | 37 |
| MET10.1 | Loop variations | 55 | 38.2 | 4.4 | FAM- CTG ACT rATG A**T**C TCT TAG CCC TTC ATT TCA GCC GAA AGC ACA TCT TTC GGG GGC T | 38 |
| MET10.2 | Loop variations | 55 | 38.3 | 1.4 | FAM- CTG ACT rATG AC**T** TCT TAG CCC TTC ATT TCA GCC GAA AGC ACA TCT TTC GGG GGC T | 39 |
| MET10.3 | Loop variations | 55 | 44.5 | 4.7 | FAM- CTG ACT rATG ACC **C**CT TAG CCC TTC ATT TCA GCC GAA AGC ACA TCT TTC GGG GGC T | 40 |
| MET10.4 | Loop variations | 55 | 40.7 | 5.7 | FAM- CTG ACT rATG ACC **TTT** TAG CCC TTC ATT TCA GCC GAA AGC ACA TCT TTC GGG GGC T | 41 |
| MET10.5 | Loop variations | 55 | 47.9 | 2.4 | FAM- CTG ACT rATG ACC TC**C** TAG CCC TTC ATT TCA GCC GAA AGC ACA TCT TTC GGG GGC T | 42 |
| MET10.6 | Loop variations | 55 | 47.2 | 3 | FAM- CTG ACT rATG ACC TCT **C**AG CCC TTC ATT TCA GCC GAA AGC ACA TCT TTC GGG GGC T | 43 |
| MET10.7 | Loop variations | 55 | 43.0 | 2.6 | FAM- CTG A**TT** rATG ACC TCT TAG CCC TTC ATT TCA GCC GAA AGC ACA TCT TTC GGG GGC T | 44 |
| MET10.8 | Loop variations | 55 | 60.0 | 1.4 | FAM- CTG AC**C** rATG ACC TCT TAG CCC TTC ATT TCA GCC GAA AGC ACA TCT TTC GGG GGC T | 45 |
| MET10.9 | Loop variations | 55 | 25.0 | 2 | FAM- CTG ACT rATG ACC TCT TAG CCC TTC AT**C** TCA GCC GAA AGC ACA TCT TTC GGG GGC T | 46 |
| MET10.10 | Loop variations | 55 | 47.3 | 0.8 | FAM- CTG ACT rATG ACC TCT **TTT** **TTT** TTC ATT TCA GCC GAA AGC ACA TCT TTC GGG GGC T | 47 |

Abbreviations include: adenosine ribonucleotide (rA) and 6-FAM (fluorescein) (FAM), % conservation analysis (% CA). Sequences are written 5'-3'. Underlined nucleotides in the DNAzymes denote the substrate sequence. Nucleotides bolded in 4TFP-CACAT sequences represent changes from the original parent sequence of 112 nucleotides. Nucleotides in 4TFP-CACAT sequences missing from the original sequence were cut from the original parent sequence of 112 nucleotides. Nucleotides bolded in S1T-TL1 sequences represent the 4T's of 4TFP. All sequences from S1T-TL1 were based on 4TFP (99 nucleotides), not the original parent sequence of 112 nucleotides. Nucleotides in S1T-TL1 sequences missing from the original sequence were cut from the 4TFP sequence. All MET sequences were also based on 4TFP, while all MET 10.1-10.10 sequences were based on MET10 (55 nucleotides). For MET10.1-10.10, nucleotides in bold represent changes from the original MET10 parent sequence.

TABLE 5

| Nucleotide Sequences | | | | |
|---|---|---|---|---|
| Name | Class | Length | Sequence | SEQ ID NO: |
| LP1-nu | | 112 | CTA TGA ACT GAC TRT GAC CTC ACT ACC AAG CAA GCA TGG ACA ATA CCG AGC CTT TCA TTT CAG CCG ATC ATA CCT CAA TGT AGA TAA GCA CAT CTT GTC ATC GGA GGC TTA G | 48 |
| MET1-nu | % CA | 77 | CTG ACT rATG ACC TCT TAG CCT TTC ATT TCA GCC GAT CAT ACC TCA ATG TAG ATA AGC ACA TCT TGT CAT CGG AGG CT | 49 |
| MET2-nu | % CA | 63 | CTG ACT rATG ACC TCT TAG CCT TTC ATT TCA GCC GAT GAT AAG CAC ATC TTG TCA TCG GAG GCT | 50 |
| MET3-nu | % CA | 55 | FAM-CTG ACT rATG ATT TTT CAT TTC AGC CGA TGA TAA GCA CAT CTT GTC ATC GGA GGC T | 51 |
| MET4-nu | % CA | 55 | CTG ACT rATG ACC TCT TAG CCT TTC ATT TCA GCC GAA AGC ACA TCT TTC GGA GGC T | 52 |
| MET5-nu | % CA | 67 | CTG ACT rATG ACC TCT TAG CCT TTC ATT TCA GCC GAT CGT AGA TAA GCA CAT CTT GTC ATC GGA GGC T | 53 |
| MET6-nu | % CA | 59 | CTG ACT rATG ACC TCT TTT TTA GCC TTT CAT TTC AGC CGA AAG CAC ATC TTT CGG AGG CT | 54 |
| MET7-nu | % CA | 101 | CTA TGA ACT GAC TrAT GAC CTC ACT ACC AAG CTT TTT TAG CCT TTC ATT TCA GCC GAT CAT ACC TCA ATG TAG ATA AGC ACA TCT TGT CAT CGG AGG CTT AG | 55 |
| MET8-nu | % CA | 57 | CTG ACT rATG ACC TCT TAG CCT TTC ATT TCA GCC GAT AAA GCA CAT CTT TCG GAG GCT | 56 |
| MET9-nu | % CA | 61 | CTG ACT rATG ACC TCT TTT TTA GCC TTT CAT TTC AGC CGA TAA AGC ACA TCT TTC GGA GGC T | 57 |
| MET10 | % CA | 55 | CTG ACT rATG ACC TCT TAG CCC TTC ATT TCA GCC GAA AGC ACA TCT TTC GGG GGC T | 58 |
| MET11 | % CA | 61 | CTG ACT rATG ACC TCT TCT AAG CCC TTC ATT TCA GCC GAA AGC ACA TCT TTC GGG GGC TTA G | 59 |
| MET12 | % CA | 51 | CTG ACT rATG ACC TCT TAG CCC TTC ATT TCA GCC AAG CAC ATC TTG GGG GCT | 60 |
| MET13 | % CA | 59 | CTG ACT rATG ACC TCT TTT TTA GCC CTT CAT TTC AGC CGA AAG CAC ATC TTT CGG GGG CT | 61 |
| MET10.1 | Loop varia-tions | 55 | CTG ACT rATG A**T**C TCT TAG CCC TTC ATT TCA GCC GAA AGC ACA TCT TTC GGG GGC T | 62 |
| MET10.2 | Loop varia-tions | 55 | CTG ACT rATG AC**T** TCT TAG CCC TTC ATT TCA GCC GAA AGC ACA TCT TTC GGG GGC T | 63 |
| MET10.3 | Loop varia-tions | 55 | CTG ACT rATG ACC **C**CT TAG CCC TTC ATT TCA GCC GAA AGC ACA TCT TTC GGG GGC T | 64 |
| MET10.4 | Loop varia-tions | 55 | CTG ACT rATG ACC **TT**T TAG CCC TTC ATT TCA GCC GAA AGC ACA TCT TTC GGG GGC T | 65 |

TABLE 5-continued

| Name | Class | Length | Sequence | SEQ ID NO: |
|---|---|---|---|---|
| Nucleotide Sequences | | | | |
| MET10.5 | Loop variations | 55 | CTG ACT rATG ACC TCC TAG CCC TTC ATT TCA GCC GAA AGC ACA TCT TTC GGG GGC T | 66 |
| MET10.6 | Loop variations | 55 | CTG ACT rATG ACC TCT CAG CCC TTC ATT TCA GCC GAA AGC ACA TCT TTC GGG GGC T | 67 |
| MET10.7 | Loop variations | 55 | CTG ATT rATG ACC TCT TAG CCC TTC ATT TCA GCC GAA AGC ACA TCT TTC GGG GGC T | 68 |
| MET10.8 | Loop variations | 55 | CTG ACC rATG ACC TCT TAG CCC TTC ATT TCA GCC GAA AGC ACA TCT TTC GGG GGC T | 69 |
| MET10.9 | Loop variations | 55 | CTG ACT rATG ACC TCT TAG CCC TTC ATC TCA GCC GAA AGC ACA TCT TTC GGG GGC T | 70 |
| MET10.10 | Loop variations | 55 | CTG ACT rATG ACC TCT TTT TTT TTC ATT TCA GCC GAA AGC ACA TCT TTC GGG GGC T | 71 |
| FIG. 1B | Random Domain of LP1 | | CTT TCA TTT CAG CCG ATC ATA CCT CAA TGT AGA TAA GCA C | 72 |
| LP3 | | | CTA TGA ACT GAC QrAF GAC CTC ACT ACC AAG CAA GCATGG ACA ATA CCG AGC N40 ATC TTG TCA TCG GAG GCT TAG | 73 |
| R11-R2 | | | CTA TGA ACT GAC QrAF GAC CTC ACT ACC AAG CAA GCA TGG ACA ATA CCG AGC CTT TCA TTT CAG CCG ATC ATA CCT CAA TGT AGA TAA GCA C ATC TTG TCA TCG GAG G CTT AG | 74 |
| LP3Z1 | | | CTA TGA ACT GAC QrAF GAC CTC ACT ACC AAG CAA GCA TGG ACA ATA CCG AGC CTT TCA TTT CAG CCG ATC ATA CCT CAA TGT AGA TAA GCA C ATC TTG TCA TCG GAG G CTT AGT AGC CGA AGT TGC TGA | 75 |
| FIG. 22 Rank 1 | | | CGG TCA TTT CAG CGG GTA CTT CCT CAA AGA AGA AAA GCA CAT CTT TTC CGC GGA TC | 76 |
| FIG. 22 Rank 2 | | | CCT TCA TTT CAG CGG AGC ATA CCA CAC GGT AGA CAA GCA CAT CTT GTC CCG GGG CG | 77 |
| FIG. 22 Rank 3 | | | CCT TCA TTT CAG ACG ATG ATA CCT CAA TTT AGT TAA GCA CAT CTT ATC GTG GGC GC | 78 |
| FIG. 22 Rank 4 | | | CCT TCA TTT CAG CTG ATC ATA CCG CAA TAG CGG AAA GCA CAT CTT TTC AGG GGA TC | 79 |
| FIG. 22 Rank 5 | | | ACT TCA TTT CAG CTG ATC AAT CCA TAT TGT AGA TGA GCA CTT CTC GTC ATC TGG TG | 80 |
| FIG. 22 Rank 6 | | | CCT TCA TTT CAG ACG ATC TTC TCT CAG TCA AGA TAG GCA CAT CCT GTC ATC GGG GG | 81 |
| FIG. 22 Rank 7 | | | ACT TCA TTT CAG CCG TTC ACG ACC GAC AGT GGA TAA GCA CAT CTT ATC ACG GGT GC | 82 |
| FIG. 22 Rank 8 | | | ATT TCA TTT CAG CCG ATG TTA CCT TAC TGG AAA TAG CCA CCC CTG TTT ATC GGA TG | 83 |

TABLE 5-continued

| Nucleotide Sequences | | | | |
|---|---|---|---|---|
| Name | Class | Length | Sequence | SEQ ID NO: |
| FIG. 22 Rank 9 | | | CCT TCA TTT CAG CTG ATC GTA CCT CGA TTT AGG CAA GCA CAT CTT GTC AGG GGC GA | 84 |
| FIG. 22 Rank 10 | | | CGT TCA TTT CAG CCG ATC CTA CCT CCA TGG AGG CAA GCA CAT CTT GTC GGC GGA TC | 85 |
| Middle region | | | AAGCACATCTT | 186 |
| FIG. 25 | Truncated 4TFP | | CTA TGA ACT GAC TrAT GAC CTC ACT ACC AAG CT TTT AGC CTT TCA TTT CAG CCG ATC ATA CCT CAA TGT AGA TAA GCA CAT CTT GTC ATC GGA GGC T | 187 |
| FIG. 25 | Truncated 4TFP | | CTA TGA ACT GAC TrAT GAC CTC ACT ACC AAG CT TTT AGC CCT TCA TTT CAG CCG ATC ATA CCT CAA TGT AGA TAA GCA CAT CTT GTC ATC GGG GGC T | 188 |
| FIG. 29 | Multiple Sequence Alignment | | CTTTCATTTCAGCCGATCATACCTCAATGTA GATAAGCACATCTTGTCATCGGAGGCTTAG | 189 |
| FIG. 29 | Cluster Analysis | | CCTTCATTTCAGCCGATCATACCTCAATGTA GATAAGCACATCTTGTCATCGGAGGCTTAG | 190 |

Evidence to support the predicted pseudoknot interaction included the drastic increase in % cleavage observed between MET4 (41.7%) and MET10 (81.7%) where the only difference was the A-T to G-C substitution at positions 2 and 54 (FIG. 29). Interestingly, the G-C base pair seems to have stabilized the 5-nt 3'-tail interaction with a complementary stretch in the 5'-loop of MET10 (FIG. 26), where the deletion of 3'-terminal binding nt drastically decreased activity (MET3: 4.4% clv). Further evidence to support the pseudoknot structure included the covariation observed at positions 1 (C/A variants) and position 55 (T/G variants) in FIG. 29. Finally, a G variant emerged at position 3, which was an unpaired T, where the formation of a G-C base pair would have stabilized substrate region binding (FIG. 25 and FIG. 29).

Finally, the selectivity of the truncated sequence was assessed (FIG. 27). Previously, it was determined that the non-specific cleavage observed with terminally labeled LP1 sequence in the presence of other bacteria was due to endogenous RNase I. To investigate if the best truncated sequence candidates were also susceptible to non-specific RNase I cleavage, 4TFP and MET10 in the absence and presence of SUPERase-IN Rnase inhibitor that inhibits RNase A, B, C, I and T1, and select bacteria. As expected, some non-specific activation of the truncated DNAzymes were observed in the presence of *Escherichia coli* K12, and *Enterobacter aerogenes* and the absence of RNase I inhibitor. These bacteria were chosen as non-specific controls as cleavage was previously observed with the LP1 sequence in the absence of RNase inhibitor. Like the full-length sequence, in the presence of the inhibitor, non-specific activity was absent for both sequences.

Of note, there was a slight decrease of cleavage activity observed in both the 4TFP and MET10 sequences. This slight decrease can be due to non-specific degradation by other nucleases. Some evidence was provided when all of the MET truncations in CEM-LP that had been freshly prepared and never frozen were assessed (FIG. 31). Under these conditions, almost all of the truncations displayed relatively high % cleavage activities. All of the other assays preformed were evaluated from the same batch of CEM-LP that had been stored in the freezer after preparation. It is possible that either some of the protein target is degraded by freezing, or that nucleases contributing to non-specific activation are to some degree inactivated by freezing. [39] Either of these situations, or a combination of both, could explain the differences in the observed cleavage activities between freshly prepared and previously frozen CEM-LP. Nevertheless, it will be necessary to evaluate the sequence activity and specificity in the presence of naturally occurring *Legionella pneumophila* in cooling tower water in future studies. The first step towards this effort would be to evaluate target stability under various conditions, once the target is identified.

Reselection and mutational analysis are powerful methods for improving the activity of functional nucleic acids ranging from aptamers to aptazymes, however they are only two strategies of many to do so. [40] The advancement of high throughput sequencing has allowed researchers to change the way they think about sequence truncation and secondary structure analysis. Specifically, it allows for the ability to screen all sequence variants simultaneously, versus labour intensive and costly systematic deletion or rational mutation studies. The truncation of long sequences has always been desirable due to the practical limits of DNA synthesis, as well as for downstream applications.[40,41] Further, it is helpful in limiting the potential for misfolding of the sequence into nonfunctional conformations. Truncation is especially helpful for RNA-cleaving DNAzyme selections for complex targets, that typically utilize longer selection libraries to avoid reselecting variants of the 8-17 DNAzyme.[42] Tethering a sequence to a nanoparticle, immobilizing it on a sequence, or conjugating a sequence to another reporter probe/molecular recognition element is easier if the sequence is smaller. Techniques such as arbitrary truncation, partial fragmentation, enzymatic footprinting, and 1H NMR spectroscopy have proved useful in the past to identify shorter high-activity sequences and glean secondary structure information for DNAzymes.[40, 43-45] Additionally, the rational mutation of specific nucleotides and deletion of nucleotides in parent sequences to produce higher activity sequences is also an effective strategy.[45-48]

However, obtaining high throughput sequencing data allows several advantages. By performing a reselection on a sequence of interest, researchers can access a much larger sequence space, than if they were to perform systematic point mutations.[49, 50] Further, sequences can be clustered into families based on a set % identity using specifically designed programs. [51-53] Comparison of these families can identify multiple high affinity aptazymes, can identify common secondary structures, and can identify favourable point mutations in derivative sequences. Previously these types of comparisons were limited to multiple sequence alignments to identify conserved domains, and secondary structure prediction algorithms such as RNAStructure [54] and Mfold [55] to make hypotheses about potential sequence target interactions.[44] Though the main goal for selections is to identify sequences with high activity and high selectivity, there can be cases where it is desirable to balance these parameters within certain constraints. The versatility of the reselection technique has been used to fine-tune the activity of functional nucleic acids to within a range that is most compatible with a certain application, [56] and to identify sequences for related targets.[57] An alternative combinatorial approach which allows for the assessment of all possible single mutants of a DNAzyme as an alternative to reselection and mutational analysis has also been described.[58]

Following a reselection, and mutational analysis a series of systematic and rationally designed truncations of an RNA-cleaving DNAzyme called LP1 were investigated. These experiments revealed that the LP1 sequence could be minimized from 112 nucleotides to 55 nucleotides while maintaining relatively high activity and selectivity. Furthermore, this work illustrates another example of the power of reselection and mutational analysis to identify minimized sequences and variants with improved activity. The DNAzymes are useful for incorporation in user-friendly devices, specifically, MET10 DNAzyme is useful for incorporation in biosensing platform for the detection of *Legionella pneumophila* in cooling tower water, and other exposure sources.

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE DISCLOSURE

1. D. W. Fraser, T. R. Tsai, W. Orenstein, W. E. Parkin, H. J. Beecham, R. G. Sharrar, J. Harris, G. F. Mallison, S. M. Martin, J. E. McDade, et al., *N. Engl. J. Med.* 1977, 297, 1189-1197.
2. M. A. Horwitz, *J. Exp. Med.* 1983, 158, 2108-2126.
3. M. A. Horwitz, *Cell* 1984, 36, 27-33.
4. M. A. Horwitz, S. C. Silverstein, *J. Clin. Invest.* 1980, 66, 441-450.
5. M. A. Horwitz, *J. Cell Biol.* 2004, 99, 1936-1943.
6. B. M. W. Diederen, *J. Infect.* 2008, 56, 1-12.
7. J. E. Stout, V. L. Yu, *N. Engl. J. Med.* 1997, 337, 682-687.
8. H. Tronel, P. Hartemann, *Lett. Appl. Microbiol.* 2009, 48, 653-656.
9. R. P. McClung, D. M. Roth, M. Vigar, V. A. Roberts, A. M. Kahler, L. A. Cooley, E. D. Hilborn, T. J. Wade, K. E. Fullerton, J. S. Yoder, et al., *MMWR. Morb. Mortal. Wkly. Rep.* 2017, 66, 1222-1225.
10. World Health Organization, *Legionella and the Prevention of Legionellosis,* 2007.
11. C. Palazzolo, G. Maffongelli, A. D'Abramo, L. Lepore, A. Mariano, A. Vulcano, T. A. Bartoli, N. Bevilacqua, M. L. Giancola, E. Di Rosa, et al., *Euro Surveill.* 2020, 25, 1-3.
12. Hollenstein, M. DNA catalysis: The chemical repertoire of DNAzymes. *Molecules.* 20(11) 20777-20804 (2015).
13. Burstein, D., Amaro, F., Zusman, T., Lifshitz, Z., Cohen, O. Gilbert J. A., Pupko, T., Shuman, H. A., and Segal, G. Genomic analysis of 38 *Legionella* species identifies large and diverse effector repertoires. *Nature Genetics* 48, 167-175 (2016)
14. Rao, C., Guyard, C., Pelaz, C., Wasserscheid, J., Bondy-Denomy, J., Dewar, K., and Ensminger, A. W. Active and adaptive *Legionella* CRISPR-Cas reveals a recurrent challenge to the pathogen. *Cellular Microbiology* 18(10) 1319-1338 (2016)
15. Braun, R. S., Mendis, N., Li, L., Faucher, S. P. *Methods Mol. Biol.* 1921, 45-53 (2019).
16. Feeley, J. C. et al. Charcoal-yeast extract agar: primary isolation medium for *Legionella pneumophila. J. Clin. Microbiol.* 10, 437-41 (1979).
17. Chatfield, C. H. & Cianciotto, N. P. Culturing, media, and handling of *legionella. Methods Mol. Biol.* 954, 151-62 (2013).
18. Shen, Z. et al. A Catalytic DNA Activated by a Specific Strain of Bacterial Pathogen. *Angew. Chemie—Int. Ed.* 55, 2431-2434 (2016).
19. Zhang, W., Feng, Q., Chang, D., Tram, K. & Li, Y. In vitro selection of RNA-cleaving DNAzymes for bacterial detection. *Methods* 106, 66-75 (2016).
20. Li, Y. & Breaker, R. R. In vitro selection of kinase and ligase deoxyribozymes. *Methods* 23, 179-190 (2001).
21. Schlosser, K., Gu, J., Lam, J. C. F. & Li, Y. In vitro selection of small RNA-cleaving deoxyribozymes that cleave pyrimidine-pyrimidine junctions. *Nucleic Acids Res.* 36, 4768-77 (2008).
22. Jares-Erijman, E. A. & Jovin, T. M. FRET imaging. *Nat. Biotechnol.* 21, 1387-95 (2003).
23. Mei, S. H. J., Liu, Z., Brennan, J. D. & Li, Y. An efficient RNA-cleaving DNA enzyme that synchronizes catalysis with fluorescence signaling. *J. Am. Chem. Soc.* 125, 412-420 (2003).

24. Rothenbroker M., McConnell E. M., Gu J., Urbanus M. L., Samani S. E., Ensminger A. W., Filipe C. D. M., Li Y. *Angewandte Chemie* 2020, 60(9), 4782-4788
25. C. Tuerk, L. Gold, *Science* 1990, 249, 505-510.
26. A. D. Ellington, J. W. Szostak, *Nature* 1990, 346, 818-822.
27. M. M. Ali, S. D. Aguirre, H. Lazim, Y. Li, *Angew. Chemie Int. Ed.* 2011, 50, 3751-3754.
28. D. Chang, T. Chang, B. Salena, Y. Li, *ChemBioChem* 2020, 21, 464-468.
29. B. A. Cunha, A. Burillo, E. Bouza, *Lancet* 2016, 387, 376-385.
30. V. L. Yu, J. F. Plouffe, M. C. Pastoris, J. E. Stout, M. Schousboe, A. Widmer, J. Summersgill, T. File, C. M. Heath, D. L. Paterson, et al., *J. Infect. Dis.* 2002, 186, 127-8.
31. Z. Shen, Z. Wu, D. Chang, W. Zhang, K. Tram, C. Lee, P. Kim, B. J. Salena, Y. Li, *Angew. Chemie Int. Ed.* 2016, 55, 2431-2434.
32. L. Gu, W. Yan, H. Wu, S. Fan, W. Ren, S. Wang, M. Lyu, J. Liu, *Anal. Chem.* 2019, 91, 7887-7893.
33. S. Duda, J. L. Baron, M. M. Wagener, R. D. Vidic, J. E. Stout, *Environ. Monit. Assess.* 2015, 187, 393.
34. M. Liu, D. Chang, Y. Li, *Acc. Chem. Res.* 2017, 50, 2273-2283.
35. M. M. Ali, M. Wolfe, K. Tram, J. Gu, C. D. M. M. Filipe, Y. Li, J. D. Brennan, *Angew. Chem. Int. Ed.* 2019, 1, 9907-9911.
36. R. Gysbers, K. Tram, J. Gu, Y. Li, *Sci. Rep.* 2015, 5, 1-8.
37. L. Gu, R. Saran, W. Yan, P. J. J. Huang, S. Wang, M. Lyu, J. Liu, *ACS Omega* 2018, 3, 15174-15181.
38. T. Yu, W. Zhou, J. Liu, *Anal. Methods* 2018, 10, 1740-1746.
39. B. S. Bhatnagar, R. H. Bogner, M. J. Pikal, Pharm. Dev. Technol. 2007, 12, 505-523.
40. S. Gao, X. Zheng, B. Jiao, L. Wang, *Anal. Bioanal. Chem.* 2016, 408, 4567-4573.
41. T. K. Sharma, J. G. Bruno, A. Dhiman, *Biotechnol. Adv.* 2017, 35, 275-301.
42. J. C. F. Lam, S. O. Kwan, Y. Li, *Mol. Biosyst.* 2011, 7, 2139-2146.
43. N. R. Frost, M. McKeague, D. Falcioni, M. C. DeRosa, *Analyst* 2015, 140, 6643-6651.
44. S. K. Silverman, in *Funct. Nucleic Acids Anal. Appl.*, Springer New York, N.Y., NY, 2009, pp. 47-108.
45. M. Cheng, J. Zhou, G. Jia, X. Ai, J. L. Mergny, C. Li, *Biochim. Biophys. Acta—Gen. Subj.* 2017, 1861, 1913-1920.
46. A. K. Brown, J. Liu, Y. He, Y. Lu, *ChemBioChem* 2009, 10, 486-492.
47. Z. Zaborowska, S. Schubert, J. Kurreck, V. A. Erdmann, *FEBS Lett.* 2005, 579, 554-558.
48. W. Zhou, Y. Zhang, P. J. J. Huang, J. Ding, J. Liu, *Nucleic Acids Res.* 2016, 44, 354-363.
49. K. Schlosser, J. C. F. Lam, Y. Li, *Nucleic Acids Res.* 2009, 37, 3545-3557.
50. N. Lehman, P. J. Unrau, *J. Mol. Evol.* 2005, 61, 245-252.
51. J. Hoinka, A. Berezhnoy, P. Dao, Z. E. Sauna, E. Gilboa, T. M. Przytycka, *Nucleic Acids Res.* 2015, 43, 5699-5707.
52. J. Hoinka, A. Berezhnoy, Z. E. Sauna, E. Gilboa, T. M. Przytycka, *Lect. Notes Comput. Sci.* (including *Subser. Lect. Notes Artif. Intell. Lect. Notes Bioinformatics*) 2014, 8394 *LNBI,* 115-128.
53. K. K. Alam, J. L. Chang, D. H. Burke, *Mol. Ther. Acids* 2015, 4, e230.
54. D. H. Mathews, *Curr. Protoc. Bioinformatics* 2014, 46, 12.6.1-12.6.25.
55. M. Zuker, *Nucleic Acids Res.* 2003, 31, 3406-3415.
56. R. J. Lake, Z. Yang, J. J. Zhang, Y. Lu, *Acc. Chem. Res.* 2019, 52, 3275-3286.
57. L. Ma, J. Liu, *ChemBioChem* 2019, 20, 537-542.
58. F. Wachowius, F. Javadi-Zarnaghi, C. Hobartner, *Angew. Chemie—Int. Ed.* 2010, 49, 8504-8508.

The invention claimed is:

1. A DNAzyme for detecting *Legionella pneumophila* comprising a sequence selected from the group consisting of SEQ ID NOS: 7-17, 21-71, 187, and 188, or a functional fragment or modified derivative thereof, wherein the functional fragment or the modified derivative comprises a first domain comprising nucleotides 3-12 of SEQ ID NO: 189 and a second domain comprising the nucleotide sequence of SEQ ID NO: 186.

2. The DNAzyme of claim 1, comprising a sequence selected from the group consisting of SEQ ID NOS: 7-14, 21-24, 30-36, 45, 48, 54-60, 69, 187, and 188.

3. The DNAzyme of claim 1, comprising the sequence of SEQ ID NO: 34 or 58.

4. The DNAzyme of claim 1, comprising a detectable label.

5. The DNAzyme of claim 4, wherein the detectable label comprises a fluorescent, a colorimetric, or other optical or electrochemical moiety.

6. The DNAzyme of claim 5, wherein the fluorescent moiety is a fluorophore.

7. The DNAzyme of claim 6, wherein the fluorophore is fluorescein.

8. A biosensor for detecting *Legionella pneumophila* comprising the DNAzyme of claim 1.

9. The biosensor of claim 8, further comprising a support.

10. The biosensor of claim 9, wherein the support comprises cellulose or paper.

11. A kit for detecting *Legionella pneumophila*, wherein the kit comprises the DNAzyme of claim 1 and instructions for use of the kit.

12. The kit of claim 11, further comprising one or more of: i) a buffer, ii) an RNase inhibitor, and iii) a metal ion.

13. A method for detecting the presence of *Legionella pneumophila* in a test sample, comprising:

a) contacting said test sample with the DNAzyme of claim 1, wherein the DNAzyme comprises a detectable label;
b) allowing cleavage of the DNAzyme if a target is present, thereby releasing the detectable label; and
c) measuring a detectable signal if the portion of the DNAzyme comprising the detectable label is released, wherein the RNA cleavage activity of the DNAzyme is activated by a target from *Legionella pneumophila*.

14. The method of claim 13, wherein the target is a protein target.

15. The method of claim 14, wherein the protein target is a protein target of 30-100 kDa.

16. The method of claim 13, wherein the DNAzyme detects at least 10 colony forming units of *Legionella pneumophila*.

17. A method for detecting the presence of *Legionella pneumophila* in a test sample, comprising:

a) contacting said test sample with the biosensor of claim 8, wherein the DNAzyme comprises a detectable label;

b) allowing cleavage of the DNAzyme if a target is present, thereby releasing the detectable label; and c) measuring a detectable signal if the portion of the DNAzyme comprising the detectable label is released, wherein the RNA cleavage activity of the DNAzyme is activated by a target from *Legionella pneumophila*.

18. The method of claim 17, wherein the target is a protein target.

19. The method of claim 18, wherein the protein target is a protein target of 30-100 kDa.

20. The method of claim 17, wherein the biosensor detects at least 10 colony forming units of *Legionella pneumophila*.

* * * * *

SEQUENCE LISTING

```
<160> NUMBER OF SEQ ID NOS: 190

<210> SEQ ID NO 1
<211> LENGTH: 82
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (22)..(61)
<223> OTHER INFORMATION: n is a, c, g, or t

<400> SEQUENCE: 1

caagcatgga caataccgag cnnnnnnnnn nnnnnnnnnn nnnnnnnnnn nnnnnnnnnn      60

natcttgtca tcggaggctt ag                                                82


<210> SEQ ID NO 2
<211> LENGTH: 30
<212> TYPE: DNA
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (13)..(13)
<223> OTHER INFORMATION: n is DABCYL-dT
<220> FEATURE:
```

-continued

<221> NAME/KEY: MISC_FEATURE
<222> LOCATION: (14)..(14)
<223> OTHER INFORMATION: n is adenosine ribonucleotide
<220> FEATURE:
<221> NAME/KEY: MISC_FEATURE
<222> LOCATION: (15)..(15)
<223> OTHER INFORMATION: n is fluorescein-dT

<400> SEQUENCE: 2
ctatgaactg acnnngacct cactaccaag 30

<210> SEQ ID NO 3
<211> LENGTH: 30
<212> TYPE: DNA
<213> ORGANISM: Artificial
<220> FEATURE:
<223> OTHER INFORMATION: Synthetic Construct

<400> SEQUENCE: 3
tattgtccat gcttgcttgg tagtgaggtc 30

<210> SEQ ID NO 4
<211> LENGTH: 21
<212> TYPE: DNA
<213> ORGANISM: Artificial
<220> FEATURE:
<223> OTHER INFORMATION: Synthetic Construct

<400> SEQUENCE: 4
caagcatgga caataccgag c 21

<210> SEQ ID NO 5
<211> LENGTH: 21
<212> TYPE: DNA
<213> ORGANISM: Artificial
<220> FEATURE:
<223> OTHER INFORMATION: Synthetic Construct

<400> SEQUENCE: 5
ctaagcctcc gatgacaaga t 21

<210> SEQ ID NO 6
<211> LENGTH: 36
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: n is 18-atom hexa-ethyleneglycol ("Int Spacer 18")

<400> SEQUENCE: 6
tttttttttt tttttntaag cctccgatga caagat 36

<210> SEQ ID NO 7
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is DABCYL-dT
<220> FEATURE:
<221> NAME/KEY: misc_feature
<222> LOCATION: (15)..(15)

-continued

<223> OTHER INFORMATION: n is fluorescein-dT

<400> SEQUENCE: 7
ctatgaactg acnrngacct cactaccaag caagcatgga caataccgag cctttcattt 60
cagccgatca tacctcaatg tagataagca catcttgtca tcggaggctt ag 112

<210> SEQ ID NO 8
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (112)..(112)
<223> OTHER INFORMATION: n is is fluorescein-guanine

<400> SEQUENCE: 8
ctatgaactg actrtgacct cactaccaag caagcatgga caataccgag cctttcattt 60
cagccgatca tacctcaatg tagataagca catcttgtca tcggaggctt an 112

<210> SEQ ID NO 9
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine

<400> SEQUENCE: 9
ntatgaactg actrtgacct cactaccaag caagcatgga caataccgag cctttcattt 60
cagccgatca tacctcaatg tagataagca catcttgtca tcggaggctt ag 112

<210> SEQ ID NO 10
<211> LENGTH: 113
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (31)..(31)
<223> OTHER INFORMATION: n is gamma-[p32]-adenosine

<400> SEQUENCE: 10
ctatgaactg actrtgacct cactaccaag ncaagcatgg acaataccga gcctttcatt 60
tcagccgatc atacctcaat gtagataagc acatcttgtc atcggaggct tag 113

<210> SEQ ID NO 11
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (13)..(13)
<223> OTHER INFORMATION: n is dT-Q (DABCYL-dT)
<220> FEATURE:
<221> NAME/KEY: misc_feature
<222> LOCATION: (14)..(14)
<223> OTHER INFORMATION: n is adenosine ribonucleotide
<220> FEATURE:
<221> NAME/KEY: misc_feature
<222> LOCATION: (15)..(15)
<223> OTHER INFORMATION: n is dT-F (fluorescein-dT)

<400> SEQUENCE: 11
ntatgaactg acnnngacct cactaccaag caagcatgga caataccgag cctttcattt 60
cagccgatca tacctcaatg tagataagca catcttgtca tcggaggctt ag 112

<210> SEQ ID NO 12
<211> LENGTH: 99
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 12
ntatgaactg actntgacct cactaccaag cttttagcct ttcatttcag ccgatcatac 60
ctcaatgtag ataagcacat cttgtcatcg gaggcttag 99

<210> SEQ ID NO 13
<211> LENGTH: 104
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 13
ntatgaactg actntgacct cactaccaag cttttttttt agcctttcat ttcagccgat 60
catacctcaa tgtagataag cacatcttgt catcggaggc ttag 104

<210> SEQ ID NO 14
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 14
ntatgaactg actntgacct cactaccaag cttttttttt ttttttttag cctttcattt 60
cagccgatca tacctcaatg tagataagca catcttgtca tcggaggctt ag 112

<210> SEQ ID NO 15
<211> LENGTH: 107
<212> TYPE: DNA
<213> ORGANISM: Artificial
<220> FEATURE:
<223> OTHER INFORMATION: Synthetic Construst
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 15
ntatgaactg actntgacct cactaccaag caagcatgga caataccgag cctttcattt 60
cagccgatca tacctcaatg tagataagca catcttgtca tcggagg 107

<210> SEQ ID NO 16
<211> LENGTH: 102
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 16
ntatgaactg actntgacct cactaccaag caagcatgga caataccgag cctttcattt 60
cagccgatca tacctcaatg tagataagca catcttgtca tc 102

<210> SEQ ID NO 17
<211> LENGTH: 97
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 17
ntatgaactg actntgacct cactaccaag caagcatgga caataccgag cctttcattt 60
cagccgatca tacctcaatg tagataagca catcttg 97

<210> SEQ ID NO 18
<211> LENGTH: 92
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature -continued
<222> LOCATION: (14)..(14)
<223> OTHER INFORMATION: n is adenosine ribonucleotide

<400> SEQUENCE: 18
ntatgaactg actntgacct cactaccaag caagcatgga caataccgag cctttcattt 60
cagccgatca tacctcaatg tagataagca ca 92

<210> SEQ ID NO 19
<211> LENGTH: 87
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 19
ntatgaactg actntgacct cactaccaag caagcatgga caataccgag cctttcattt 60
cagccgatca tacctcaatg tagataa 87

<210> SEQ ID NO 20
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 20
ntatgaactg actntgacct cactaccaag caagcatgga caataccgag cctttcattt 60
cagccgatca tacctcaatg tagataagtt tttcttgtca tcggaggctt ag 112

<210> SEQ ID NO 21
<211> LENGTH: 97
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 21
ntatgaactg actntgacct cactaccaag cttttagcct ttcatttcag ccgatcatac 60
ctcaatgtaa taagcacatc ttgtatcgga ggcttag 97

<210> SEQ ID NO 22
<211> LENGTH: 95
<212> TYPE: DNA

-continued

<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 22
ntatgaactg actntgacct cactaccaag cttttagcct ttcatttcag ccgatcatac 60
ctcaatgtat aagcacatct tgatcggagg cttag 95

<210> SEQ ID NO 23
<211> LENGTH: 94
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 23
ntatgaactg actntgacct cactaccaag cttttagcct ttcatttcag ccgatcatac 60
ctcaatgtat aagcacatct tatcggaggc ttag 94

<210> SEQ ID NO 24
<211> LENGTH: 93
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 24
ntatgaactg actntgacct cactaccaag cttttagcct ttcatttcag ccgatcatat 60
gtagataagc acatcttgtc atcggaggct tag 93

<210> SEQ ID NO 25
<211> LENGTH: 77
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 25
ntgactntga cctcttagcc tttcatttca gccgatcata cctcaatgta gataagcaca 60
tcttgtcatc ggaggct 77

<210> SEQ ID NO 26
<211> LENGTH: 63
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 26
ntgactntga cctcttagcc tttcatttca gccgatgata agcacatctt gtcatcggag 60
gct 63

<210> SEQ ID NO 27
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 27
ntgactntga tttttcattt cagccgatga taagcacatc ttgtcatcgg aggct 55

<210> SEQ ID NO 28
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 28
ntgactntga cctcttagcc tttcatttca gccgaaagca catctttcgg aggct 55

<210> SEQ ID NO 29
<211> LENGTH: 67
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:

-continued

```
<221> NAME/KEY: misc_feature
<222> LOCATION: (7)..(7)
<223> OTHER INFORMATION: n is adenosine ribonucleotide

<400> SEQUENCE: 29

ntgactntga cctcttagcc tttcatttca gccgatcgta gataagcaca tcttgtcatc     60

ggaggct                                                              67

<210> SEQ ID NO 30
<211> LENGTH: 59
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 30

ntgactntga cctctttttt agcctttcat ttcagccgaa agcacatctt tcggaggct     59

<210> SEQ ID NO 31
<211> LENGTH: 101
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (14)..(14)
<223> OTHER INFORMATION: n is adenosine ribonucleotide

<400> SEQUENCE: 31

ntatgaactg actntgacct cactaccaag cttttttagc ctttcatttc agccgatcat     60

acctcaatgt agataagcac atcttgtcat cggaggctta g                       101

<210> SEQ ID NO 32
<211> LENGTH: 57
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 32

ntgactntga cctcttagcc tttcatttca gccgataaag cacatctttc ggaggct       57

<210> SEQ ID NO 33
<211> LENGTH: 61
<212> TYPE: DNA
<213> ORGANISM: Artificial
<220> FEATURE:
<223> OTHER INFORMATION: Synthetic Construct
```

-continued

<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 33
ntgactntga cctctttttt agcctttcat ttcagccgat aaagcacatc tttcggaggc 60
t 61

<210> SEQ ID NO 34
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 34
ntgactntga cctcttagcc cttcatttca gccgaaagca catctttcgg gggct 55

<210> SEQ ID NO 35
<211> LENGTH: 61
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 35
ntgactntga cctcttctaa gcccttcatt tcagccgaaa gcacatcttt cgggggctta 60
g 61

<210> SEQ ID NO 36
<211> LENGTH: 51
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 36
ntgactntga cctcttagcc cttcatttca gccaagcaca tcttgggggc t 51

<210> SEQ ID NO 37

-continued

```
<211> LENGTH: 59
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 37

ntgactntga cctctttttt agcccttcat ttcagccgaa agcacatctt tcgggggct          59

<210> SEQ ID NO 38
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 38

ntgactntga tctcttagcc cttcatttca gccgaaagca catctttcgg gggct          55

<210> SEQ ID NO 39
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 39

ntgactntga cttcttagcc cttcatttca gccgaaagca catctttcgg gggct          55

<210> SEQ ID NO 40
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 40

ntgactntga ccccttagcc cttcatttca gccgaaagca catctttcgg gggct          55
```

<210> SEQ ID NO 41
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 41
ntgactntga ccttttagcc cttcatttca gccgaaagca catctttcgg gggct 55

<210> SEQ ID NO 42
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 42
ntgactntga cctcctagcc cttcatttca gccgaaagca catctttcgg gggct 55

<210> SEQ ID NO 43
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 43
ntgactntga cctctcagcc cttcatttca gccgaaagca catctttcgg gggct 55

<210> SEQ ID NO 44
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 44
ntgattntga cctcttagcc cttcatttca gccgaaagca catctttcgg gggct 55

<210> SEQ ID NO 45
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 45
ntgaccntga cctcttagcc cttcatttca gccgaaagca catctttcgg gggct 55

<210> SEQ ID NO 46
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 46
ntgactntga cctcttagcc cttcatctca gccgaaagca catctttcgg gggct 55

<210> SEQ ID NO 47
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is fluorescein-cytosine
<220> FEATURE:
<221> NAME/KEY: misc_feature
<222> LOCATION: (7)..(7)
<223> OTHER INFORMATION: n is adenosine ribonucleotide

<400> SEQUENCE: 47
ntgactntga cctctttttt tttcatttca gccgaaagca catctttcgg gggct 55

<210> SEQ ID NO 48
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: n is adenosine ribonucleotide

<400> SEQUENCE: 48
ctatgaactg actntgacct cactaccaag caagcatgga caataccgag cctttcattt 60
cagccgatca tacctcaatg tagataagca catcttgtca tcggaggctt ag 112

-continued

<210> SEQ ID NO 49
<211> LENGTH: 77
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 49
ctgactntga cctcttagcc tttcatttca gccgatcata cctcaatgta gataagcaca 60
tcttgtcatc ggaggct 77

<210> SEQ ID NO 50
<211> LENGTH: 63
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 50
ctgactntga cctcttagcc tttcatttca gccgatgata agcacatctt gtcatcggag 60
gct 63

<210> SEQ ID NO 51
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 51
ctgactntga tttttcattt cagccgatga taagcacatc ttgtcatcgg aggct 55

<210> SEQ ID NO 52
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 52
ctgactntga cctcttagcc tttcatttca gccgaaagca catctttcgg aggct 55

<210> SEQ ID NO 53
<211> LENGTH: 67
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 53
ctgactntga cctcttagcc tttcatttca gccgatcgta gataagcaca tcttgtcatc 60
ggaggct 67

<210> SEQ ID NO 54
<211> LENGTH: 59
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 54
ctgactntga cctctttttt agcctttcat ttcagccgaa agcacatctt tcggaggct 59

<210> SEQ ID NO 55
<211> LENGTH: 101
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: n is adenosine ribonucleotide

<400> SEQUENCE: 55
ctatgaactg actntgacct cactaccaag ctttttttagc ctttcatttc agccgatcat 60
acctcaatgt agataagcac atcttgtcat cggaggctta g 101

<210> SEQ ID NO 56
<211> LENGTH: 57
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 56
ctgactntga cctcttagcc tttcatttca gccgataaag cacatctttc ggaggct 57

<210> SEQ ID NO 57
<211> LENGTH: 61
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 57
ctgactntga cctctttttt agcctttcat ttcagccgat aaagcacatc tttcggaggc 60
t 61

<210> SEQ ID NO 58
<211> LENGTH: 55
<212> TYPE: DNA
<213> ORGANISM: Artificial

<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 58
ctgactntga cctcttagcc cttcatttca gccgaaagca catctttcgg gggct 55

<210> SEQ ID NO 59
<211> LENGTH: 61
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 59
ctgactntga cctcttctaa gcccttcatt tcagccgaaa gcacatcttt cgggggctta 60
g 61

<210> SEQ ID NO 60
<211> LENGTH: 51
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 60
ctgactntga cctcttagcc cttcatttca gccaagcaca tcttgggggc t 51

<210> SEQ ID NO 61
<211> LENGTH: 59
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 61
ctgactntga cctctttttt agcccttcat ttcagccgaa agcacatctt tcgggggct 59

<210> SEQ ID NO 62
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 62
ctgactntga tctcttagcc cttcatttca gccgaaagca catctttcgg gggct 55

<210> SEQ ID NO 63

<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 63
ctgactntga cttcttagcc cttcatttca gccgaaagca catctttcgg gggct 55

<210> SEQ ID NO 64
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 64
ctgactntga ccccttagcc cttcatttca gccgaaagca catctttcgg gggct 55

<210> SEQ ID NO 65
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 65
ctgactntga ccttttagcc cttcatttca gccgaaagca catctttcgg gggct 55

<210> SEQ ID NO 66
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 66
ctgactntga cctcctagcc cttcatttca gccgaaagca catctttcgg gggct 55

<210> SEQ ID NO 67
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 67
ctgactntga cctctcagcc cttcatttca gccgaaagca catctttcgg gggct 55

<210> SEQ ID NO 68
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 68
ctgattntga cctcttagcc cttcatttca gccgaaagca catctttcgg gggct 55

<210> SEQ ID NO 69
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 69
ctgaccntga cctcttagcc cttcatttca gccgaaagca catctttcgg gggct 55

<210> SEQ ID NO 70
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 70
ctgactntga cctcttagcc cttcatctca gccgaaagca catctttcgg gggct 55

<210> SEQ ID NO 71
<211> LENGTH: 55
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: n is adenosine ribonucleotide

<400> SEQUENCE: 71
ctgactntga cctctttttt tttcatttca gccgaaagca catctttcgg gggct 55

<210> SEQ ID NO 72
<211> LENGTH: 40
<212> TYPE: DNA
<213> ORGANISM: Artificial
<220> FEATURE:
<223> OTHER INFORMATION: Synthetic Construct

<400> SEQUENCE: 72
ctttcatttc agccgatcat acctcaatgt agataagcac 40

<210> SEQ ID NO 73
<211> LENGTH: 112
<212> TYPE: DNA

```
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is DABCYL-dT
<220> FEATURE:
<221> NAME/KEY: misc_feature
<222> LOCATION: (14)..(14)
<223> OTHER INFORMATION: n is adenosine ribonucleotide
<220> FEATURE:
<221> NAME/KEY: misc_feature
<222> LOCATION: (15)..(15)
<223> OTHER INFORMATION: n is fluorescein-dT
<220> FEATURE:
<221> NAME/KEY: misc_feature
<222> LOCATION: (52)..(91)
<223> OTHER INFORMATION: n is a, c, g, or t

<400> SEQUENCE: 73

ctatgaactg acnnngacct cactaccaag caagcatgga caataccgag cnnnnnnnnn     60

nnnnnnnnnn nnnnnnnnnn nnnnnnnnnn natcttgtca tcggaggctt ag           112


<210> SEQ ID NO 74
<211> LENGTH: 112
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is DABCYL-dT
<220> FEATURE:
<221> NAME/KEY: misc_feature
<222> LOCATION: (14)..(14)
<223> OTHER INFORMATION: n is adenosine ribonucleotide
<220> FEATURE:
<221> NAME/KEY: misc_feature
<222> LOCATION: (15)..(15)
<223> OTHER INFORMATION: n is fluorescein-dT

<400> SEQUENCE: 74

ctatgaactg acnnngacct cactaccaag caagcatgga caataccgag cctttcattt     60

cagccgatca tacctcaatg tagataagca catcttgtca tcggaggctt ag           112


<210> SEQ ID NO 75
<211> LENGTH: 128
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is DABCYL-dT
<220> FEATURE:
<221> NAME/KEY: misc_feature
<222> LOCATION: (14)..(14)
<223> OTHER INFORMATION: n is adenosine ribonucleotide
<220> FEATURE:
<221> NAME/KEY: misc_feature
<222> LOCATION: (15)..(15)
<223> OTHER INFORMATION: n is fluorescein-dT

<400> SEQUENCE: 75

ctatgaactg acnnngacct cactaccaag caagcatgga caataccgag cctttcattt     60

cagccgatca tacctcaatg tagataagca catcttgtca tcggaggctt agtagccgaa    120

gttgctga                                                             128
```

<210> SEQ ID NO 76
<211> LENGTH: 56
<212> TYPE: DNA
<213> ORGANISM: Artificial
<220> FEATURE:
<223> OTHER INFORMATION: Synthetic Construct

<400> SEQUENCE: 76
cggtcatttc agcgggtact tcctcaaaga agaaaagcac atcttttccg cggatc 56

<210> SEQ ID NO 77
<211> LENGTH: 56
<212> TYPE: DNA
<213> ORGANISM: Artificial
<220> FEATURE:
<223> OTHER INFORMATION: Synthetic Construct

<400> SEQUENCE: 77
ccttcatttc agcggagcat accacacggt agacaagcac atcttgtccc ggggcg 56

<210> SEQ ID NO 78
<211> LENGTH: 56
<212> TYPE: DNA
<213> ORGANISM: Artificial
<220> FEATURE:
<223> OTHER INFORMATION: Synthetic Construct

<400> SEQUENCE: 78
ccttcatttc agacgatgat acctcaattt agttaagcac atcttatcgt gggcgc 56

<210> SEQ ID NO 79
<211> LENGTH: 56
<212> TYPE: DNA
<213> ORGANISM: Artificial
<220> FEATURE:
<223> OTHER INFORMATION: Synthetic Construct

<400> SEQUENCE: 79
ccttcatttc agctgatcat accgcaatag cggaaagcac atcttttcag gggatc 56

<210> SEQ ID NO 80
<211> LENGTH: 56
<212> TYPE: DNA
<213> ORGANISM: Artificial
<220> FEATURE:
<223> OTHER INFORMATION: Synthetic Construct

<400> SEQUENCE: 80
acttcatttc agctgatcaa tccatattgt agatgagcac ttctcgtcat ctggtg 56

<210> SEQ ID NO 81
<211> LENGTH: 56
<212> TYPE: DNA
<213> ORGANISM: Artificial
<220> FEATURE:
<223> OTHER INFORMATION: Synthetic Construct

<400> SEQUENCE: 81
ccttcatttc agacgatctt ctctcagtca agataggcac atcctgtcat cggggg 56

<210> SEQ ID NO 82
<211> LENGTH: 56
<212> TYPE: DNA
<213> ORGANISM: Artificial
<220> FEATURE:

-continued

<223> OTHER INFORMATION: Synthetic Construct

<400> SEQUENCE: 82
acttcatttc agccgttcac gaccgacagt ggataagcac atcttatcac gggtgc 56

<210> SEQ ID NO 83
<211> LENGTH: 56
<212> TYPE: DNA
<213> ORGANISM: Artificial
<220> FEATURE:
<223> OTHER INFORMATION: Synthetic Construct

<400> SEQUENCE: 83
atttcatttc agccgatgtt accttactgg aaatagccac ccctgtttat cggatg 56

<210> SEQ ID NO 84
<211> LENGTH: 56
<212> TYPE: DNA
<213> ORGANISM: Artificial
<220> FEATURE:
<223> OTHER INFORMATION: Synthetic Construct

<400> SEQUENCE: 84
ccttcatttc agctgatcgt acctcgattt aggcaagcac atcttgtcag gggcga 56

<210> SEQ ID NO 85
<211> LENGTH: 56
<212> TYPE: DNA
<213> ORGANISM: Artificial
<220> FEATURE:
<223> OTHER INFORMATION: Synthetic Construct

<400> SEQUENCE: 85
cgttcatttc agccgatcct acctccatgg aggcaagcac atcttgtcgg cggatc 56

<210> SEQ ID NO 86
<211> LENGTH: 40
<212> TYPE: DNA
<213> ORGANISM: Artificial
<220> FEATURE:
<223> OTHER INFORMATION: Synthetic Construct

<400> SEQUENCE: 86
aacggttgct ctcataagag tgatgccgat tcatttccac 40

<210> SEQ ID NO 87
<211> LENGTH: 40
<212> TYPE: DNA
<213> ORGANISM: Artificial
<220> FEATURE:
<223> OTHER INFORMATION: Synthetic Construct

<400> SEQUENCE: 87
ctttcatttc agccgatcat acctcaatgt agataagcac 40

<210> SEQ ID NO 88
<211> LENGTH: 40
<212> TYPE: DNA
<213> ORGANISM: Artificial
<220> FEATURE:
<223> OTHER INFORMATION: Synthetic Construct

<400> SEQUENCE: 88
agcaactggg acagatcgac agcctttcat ttcaagtcac 40

-continued

<210> SEQ ID NO 89
<211> LENGTH: 40
<212> TYPE: DNA
<213> ORGANISM: Artificial
<220> FEATURE:
<223> OTHER INFORMATION: Synthetic Construct

<400> SEQUENCE: 89
aacggttgct cccataagag tgatgccgat tcatttccac 40

<210> SEQ ID NO 90
<211> LENGTH: 40
<212> TYPE: DNA
<213> ORGANISM: Artificial
<220> FEATURE:
<223> OTHER INFORMATION: Synthetic Construct

<400> SEQUENCE: 90
aacggttgcc ctcataagag tgatgccgat tcatttccac 40

<210> SEQ ID NO 91
<211> LENGTH: 40
<212> TYPE: DNA
<213> ORGANISM: Artificial
<220> FEATURE:
<223> OTHER INFORMATION: Synthetic Construct

<400> SEQUENCE: 91
ctttcatttc agccgattat acctcaatat agataagcac 40

<210> SEQ ID NO 92
<211> LENGTH: 40
<212> TYPE: DNA
<213> ORGANISM: Artificial
<220> FEATURE:
<223> OTHER INFORMATION: Synthetic Construct

<400> SEQUENCE: 92
ctttcatttc agccgatcat acctcaatat agataagcac 40

<210> SEQ ID NO 93
<211> LENGTH: 40
<212> TYPE: DNA
<213> ORGANISM: Artificial
<220> FEATURE:
<223> OTHER INFORMATION: Synthetic Construct

<400> SEQUENCE: 93
agcaactggg acagaccgac agcctttcat ttcaagtcac 40

<210> SEQ ID NO 94
<211> LENGTH: 40
<212> TYPE: DNA
<213> ORGANISM: Artificial
<220> FEATURE:
<223> OTHER INFORMATION: Synthetic Construct

<400> SEQUENCE: 94
agcaactgtg acagatcgac agcctttcat ttcaagtcac 40

<210> SEQ ID NO 95
<211> LENGTH: 40
<212> TYPE: DNA
<213> ORGANISM: Artificial
<220> FEATURE:
<223> OTHER INFORMATION: Synthetic Construct -continued

<400> SEQUENCE: 95
aggaactggg acagatcgac agcctttcat ttcaagtcac 40

<210> SEQ ID NO 96
<211> LENGTH: 40
<212> TYPE: DNA
<213> ORGANISM: Artificial
<220> FEATURE:
<223> OTHER INFORMATION: Synthetic Construct

<400> SEQUENCE: 96
aacggttgct ctcataaggg tgatgccgat tcatttccac 40

<210> SEQ ID NO 97
<211> LENGTH: 40
<212> TYPE: DNA
<213> ORGANISM: Artificial
<220> FEATURE:
<223> OTHER INFORMATION: Synthetic Construct

<400> SEQUENCE: 97
agtaactggg acagatcgac agcctttcat ttcaagtcac 40

<210> SEQ ID NO 98
<211> LENGTH: 40
<212> TYPE: DNA
<213> ORGANISM: Artificial
<220> FEATURE:
<223> OTHER INFORMATION: Synthetic Construct

<400> SEQUENCE: 98
agcaactggg acagatcgac agcctttcat ttcaagccac 40

<210> SEQ ID NO 99
<211> LENGTH: 40
<212> TYPE: DNA
<213> ORGANISM: Artificial
<220> FEATURE:
<223> OTHER INFORMATION: Synthetic Construct

<400> SEQUENCE: 99
aacggttgtt ctcataagag tgatgccgat tcatttccac 40

<210> SEQ ID NO 100
<211> LENGTH: 40
<212> TYPE: DNA
<213> ORGANISM: Artificial
<220> FEATURE:
<223> OTHER INFORMATION: Synthetic Construct

<400> SEQUENCE: 100
agcaactggg acagaccgac agcctttcat ttcaagccac 40

<210> SEQ ID NO 101
<211> LENGTH: 40
<212> TYPE: DNA
<213> ORGANISM: Artificial
<220> FEATURE:
<223> OTHER INFORMATION: Synthetic Construct

<400> SEQUENCE: 101
aacggttgcc cccataagag tgatgccgat tcatttccac 40

<210> SEQ ID NO 102
<211> LENGTH: 40

<212> TYPE: DNA
<213> ORGANISM: Artificial
<220> FEATURE:
<223> OTHER INFORMATION: Synthetic Construct

<400> SEQUENCE: 102
ctttcatttc agccgatcat acctcaatat agacaagcac 40

<210> SEQ ID NO 103
<211> LENGTH: 40
<212> TYPE: DNA
<213> ORGANISM: Artificial
<220> FEATURE:
<223> OTHER INFORMATION: Synthetic Construct

<400> SEQUENCE: 103
cccaggcatt gcaaggttga ctctccgatc attttcacac 40

<210> SEQ ID NO 104
<211> LENGTH: 40
<212> TYPE: DNA
<213> ORGANISM: Artificial
<220> FEATURE:
<223> OTHER INFORMATION: Synthetic Construct

<400> SEQUENCE: 104
ctttcatttc agccgatcat accccaatgt agataagcac 40

<210> SEQ ID NO 105
<211> LENGTH: 40
<212> TYPE: DNA
<213> ORGANISM: Artificial
<220> FEATURE:
<223> OTHER INFORMATION: Synthetic Construct

<400> SEQUENCE: 105
aacggttgct cacataagag tgatgccgat tcatttccac 40

<210> SEQ ID NO 106
<211> LENGTH: 40
<212> TYPE: DNA
<213> ORGANISM: Artificial
<220> FEATURE:
<223> OTHER INFORMATION: Synthetic Construct

<400> SEQUENCE: 106
gacggttgct ctcataagag tgatgccgat tcatttccac 40

<210> SEQ ID NO 107
<211> LENGTH: 40
<212> TYPE: DNA
<213> ORGANISM: Artificial
<220> FEATURE:
<223> OTHER INFORMATION: Synthetic Construct

<400> SEQUENCE: 107
ggcaactggg acagatcgac agcctttcat ttcaagtcac 40

<210> SEQ ID NO 108
<211> LENGTH: 40
<212> TYPE: DNA
<213> ORGANISM: Artificial
<220> FEATURE:
<223> OTHER INFORMATION: Synthetic Construct

<400> SEQUENCE: 108
agtaactggg acagaccgac agcctttcat ttcaagtcac 40

<210> SEQ ID NO 109
<211> LENGTH: 40
<212> TYPE: DNA
<213> ORGANISM: Artificial
<220> FEATURE:
<223> OTHER INFORMATION: Synthetic Construct

<400> SEQUENCE: 109
agcaactggg acagatcgac cgcctttcat ttcaagtcac 40

<210> SEQ ID NO 110
<211> LENGTH: 40
<212> TYPE: DNA
<213> ORGANISM: Artificial
<220> FEATURE:
<223> OTHER INFORMATION: Synthetic Construct

<400> SEQUENCE: 110
aggaactggg acagatcgac agcctttcat ttcaagccac 40

<210> SEQ ID NO 111
<211> LENGTH: 40
<212> TYPE: DNA
<213> ORGANISM: Artificial
<220> FEATURE:
<223> OTHER INFORMATION: Synthetic Construct

<400> SEQUENCE: 111
ctttcatttc agccgatcat acctcaatgt agacaagcac 40

<210> SEQ ID NO 112
<211> LENGTH: 40
<212> TYPE: DNA
<213> ORGANISM: Artificial
<220> FEATURE:
<223> OTHER INFORMATION: Synthetic Construct

<400> SEQUENCE: 112
aacggttggt ctcataagag tgatgccgat tcatttccac 40

<210> SEQ ID NO 113
<211> LENGTH: 40
<212> TYPE: DNA
<213> ORGANISM: Artificial
<220> FEATURE:
<223> OTHER INFORMATION: Synthetic Construct

<400> SEQUENCE: 113
ctttcatttc agccgattat acctcaatgt agataagcac 40

<210> SEQ ID NO 114
<211> LENGTH: 40
<212> TYPE: DNA
<213> ORGANISM: Artificial
<220> FEATURE:
<223> OTHER INFORMATION: Synthetic Construct

<400> SEQUENCE: 114
agtaactggg acagatcgac agcctttcat ttcaagccac 40

<210> SEQ ID NO 115
<211> LENGTH: 40
<212> TYPE: DNA
<213> ORGANISM: Artificial

<220> FEATURE:
<223> OTHER INFORMATION: Synthetic Construct

<400> SEQUENCE: 115
ctttcatttc agccgatcat gcctcaatgt agataagcac 40

<210> SEQ ID NO 116
<211> LENGTH: 40
<212> TYPE: DNA
<213> ORGANISM: Artificial
<220> FEATURE:
<223> OTHER INFORMATION: Synthetic Construct

<400> SEQUENCE: 116
agaaactggg acagatcgac agcctttcat ttcaagtcac 40

<210> SEQ ID NO 117
<211> LENGTH: 40
<212> TYPE: DNA
<213> ORGANISM: Artificial
<220> FEATURE:
<223> OTHER INFORMATION: Synthetic Construct

<400> SEQUENCE: 117
aacggttgcc ttcataagag tgatgccgat tcatttccac 40

<210> SEQ ID NO 118
<211> LENGTH: 40
<212> TYPE: DNA
<213> ORGANISM: Artificial
<220> FEATURE:
<223> OTHER INFORMATION: Synthetic Construct

<400> SEQUENCE: 118
agcggttgct ctcataagag tgatgccgat tcatttccac 40

<210> SEQ ID NO 119
<211> LENGTH: 36
<212> TYPE: DNA
<213> ORGANISM: Artificial
<220> FEATURE:
<223> OTHER INFORMATION: Synthetic Construct

<400> SEQUENCE: 119
agcaactggg acagatcgac agcctttcat ttccac 36

<210> SEQ ID NO 120
<211> LENGTH: 40
<212> TYPE: DNA
<213> ORGANISM: Artificial
<220> FEATURE:
<223> OTHER INFORMATION: Synthetic Construct

<400> SEQUENCE: 120
cacggttgct cacataagag tgatgccgat tcatttccac 40

<210> SEQ ID NO 121
<211> LENGTH: 40
<212> TYPE: DNA
<213> ORGANISM: Artificial
<220> FEATURE:
<223> OTHER INFORMATION: Synthetic Construct

<400> SEQUENCE: 121
ctttcatttc agccgatcat acctctatgt agataagcac 40

<210> SEQ ID NO 122
<211> LENGTH: 40
<212> TYPE: DNA
<213> ORGANISM: Artificial
<220> FEATURE:
<223> OTHER INFORMATION: Synthetic Construct

<400> SEQUENCE: 122
gacggttgct cccataagag tgatgccgat tcatttccac 40

<210> SEQ ID NO 123
<211> LENGTH: 40
<212> TYPE: DNA
<213> ORGANISM: Artificial
<220> FEATURE:
<223> OTHER INFORMATION: Synthetic Construct

<400> SEQUENCE: 123
agcaactggg acagatcgac ggcctttcat ttcaagtcac 40

<210> SEQ ID NO 124
<211> LENGTH: 40
<212> TYPE: DNA
<213> ORGANISM: Artificial
<220> FEATURE:
<223> OTHER INFORMATION: Synthetic Construct

<400> SEQUENCE: 124
cccgggcatt gcaaggttga ttctccgatc attttcacac 40

<210> SEQ ID NO 125
<211> LENGTH: 40
<212> TYPE: DNA
<213> ORGANISM: Artificial
<220> FEATURE:
<223> OTHER INFORMATION: Synthetic Construct

<400> SEQUENCE: 125
aacggttgct cctataagag tgatgccgat tcatttccac 40

<210> SEQ ID NO 126
<211> LENGTH: 40
<212> TYPE: DNA
<213> ORGANISM: Artificial
<220> FEATURE:
<223> OTHER INFORMATION: Synthetic Construct

<400> SEQUENCE: 126
agcggttgct cccataagag tgatgccgat tcatttccac 40

<210> SEQ ID NO 127
<211> LENGTH: 40
<212> TYPE: DNA
<213> ORGANISM: Artificial
<220> FEATURE:
<223> OTHER INFORMATION: Synthetic Construct

<400> SEQUENCE: 127
ctttcatttc agccgatcat acttcaatgt agataagcac 40

<210> SEQ ID NO 128
<211> LENGTH: 40
<212> TYPE: DNA
<213> ORGANISM: Artificial
<220> FEATURE:
<223> OTHER INFORMATION: Synthetic Construct

<400> SEQUENCE: 128
aggaactggg acagaccgac agcctttcat ttcaagtcac 40

<210> SEQ ID NO 129
<211> LENGTH: 40
<212> TYPE: DNA
<213> ORGANISM: Artificial
<220> FEATURE:
<223> OTHER INFORMATION: Synthetic Construct

<400> SEQUENCE: 129
agcaactgtg acagaccgac agcctttcat ttcaagtcac 40

<210> SEQ ID NO 130
<211> LENGTH: 40
<212> TYPE: DNA
<213> ORGANISM: Artificial
<220> FEATURE:
<223> OTHER INFORMATION: Synthetic Construct

<400> SEQUENCE: 130
agcaactgtg acagatcgac agcctttcat ttcaagccac 40

<210> SEQ ID NO 131
<211> LENGTH: 40
<212> TYPE: DNA
<213> ORGANISM: Artificial
<220> FEATURE:
<223> OTHER INFORMATION: Synthetic Construct

<400> SEQUENCE: 131
cccaggcatt gcaaggttga ttctccgatc attttcacac 40

<210> SEQ ID NO 132
<211> LENGTH: 40
<212> TYPE: DNA
<213> ORGANISM: Artificial
<220> FEATURE:
<223> OTHER INFORMATION: Synthetic Construct

<400> SEQUENCE: 132
ctttcatttc agccgatcat acctcaatgc agataagcac 40

<210> SEQ ID NO 133
<211> LENGTH: 40
<212> TYPE: DNA
<213> ORGANISM: Artificial
<220> FEATURE:
<223> OTHER INFORMATION: Synthetic Construct

<400> SEQUENCE: 133
ctttcatttc agccgatcat acctcaatac agataagcac 40

<210> SEQ ID NO 134
<211> LENGTH: 40
<212> TYPE: DNA
<213> ORGANISM: Artificial
<220> FEATURE:
<223> OTHER INFORMATION: Synthetic Construct

<400> SEQUENCE: 134
aacggttgct ttcataagag tgatgccgat tcatttccac 40

<210> SEQ ID NO 135

<211> LENGTH: 40
<212> TYPE: DNA
<213> ORGANISM: Artificial
<220> FEATURE:
<223> OTHER INFORMATION: Synthetic Construct

<400> SEQUENCE: 135
ctttcatttc agccgatcat accccaatat agataagcac 40

<210> SEQ ID NO 136
<211> LENGTH: 40
<212> TYPE: DNA
<213> ORGANISM: Artificial
<220> FEATURE:
<223> OTHER INFORMATION: Synthetic Construct

<400> SEQUENCE: 136
aacggttgct ctcataagag tgatgccgat tcatctccac 40

<210> SEQ ID NO 137
<211> LENGTH: 40
<212> TYPE: DNA
<213> ORGANISM: Artificial
<220> FEATURE:
<223> OTHER INFORMATION: Synthetic Construct

<400> SEQUENCE: 137
aacggttgcc ctcacaagag tgatgccgat tcatttccac 40

<210> SEQ ID NO 138
<211> LENGTH: 40
<212> TYPE: DNA
<213> ORGANISM: Artificial
<220> FEATURE:
<223> OTHER INFORMATION: Synthetic Construct

<400> SEQUENCE: 138
ctttcatttc agccgattat acctcaatat agacaagcac 40

<210> SEQ ID NO 139
<211> LENGTH: 40
<212> TYPE: DNA
<213> ORGANISM: Artificial
<220> FEATURE:
<223> OTHER INFORMATION: Synthetic Construct

<400> SEQUENCE: 139
ctttcatttc agccgatcat accttaatgt agataagcac 40

<210> SEQ ID NO 140
<211> LENGTH: 40
<212> TYPE: DNA
<213> ORGANISM: Artificial
<220> FEATURE:
<223> OTHER INFORMATION: Synthetic Construct

<400> SEQUENCE: 140
cacggttgct ctcataagag tgatgccgat tcatttccac 40

<210> SEQ ID NO 141
<211> LENGTH: 40
<212> TYPE: DNA
<213> ORGANISM: Artificial
<220> FEATURE:
<223> OTHER INFORMATION: Synthetic Construct

<400> SEQUENCE: 141
aacggttgct ctcacaagag tgatgccgat tcatttccac 40

<210> SEQ ID NO 142
<211> LENGTH: 40
<212> TYPE: DNA
<213> ORGANISM: Artificial
<220> FEATURE:
<223> OTHER INFORMATION: Synthetic Construct

<400> SEQUENCE: 142
ccttcatttc agccgatcat acctcaatgt agataagcac 40

<210> SEQ ID NO 143
<211> LENGTH: 40
<212> TYPE: DNA
<213> ORGANISM: Artificial
<220> FEATURE:
<223> OTHER INFORMATION: Synthetic Construct

<400> SEQUENCE: 143
tacggttgct ctcataagag tgatgccgat tcatttccac 40

<210> SEQ ID NO 144
<211> LENGTH: 40
<212> TYPE: DNA
<213> ORGANISM: Artificial
<220> FEATURE:
<223> OTHER INFORMATION: Synthetic Construct

<400> SEQUENCE: 144
ctttcatttc agccgattat accccaatat agataagcac 40

<210> SEQ ID NO 145
<211> LENGTH: 40
<212> TYPE: DNA
<213> ORGANISM: Artificial
<220> FEATURE:
<223> OTHER INFORMATION: Synthetic Construct

<400> SEQUENCE: 145
ctttcatttc agccgatcat tcctcaatgt agataagcac 40

<210> SEQ ID NO 146
<211> LENGTH: 40
<212> TYPE: DNA
<213> ORGANISM: Artificial
<220> FEATURE:
<223> OTHER INFORMATION: Synthetic Construct

<400> SEQUENCE: 146
aacggttgct cccataaggg tgatgccgat tcatttccac 40

<210> SEQ ID NO 147
<211> LENGTH: 40
<212> TYPE: DNA
<213> ORGANISM: Artificial
<220> FEATURE:
<223> OTHER INFORMATION: Synthetic Construct

<400> SEQUENCE: 147
aacggttgct ctcataagag tggtgccgat tcatttccac 40

<210> SEQ ID NO 148
<211> LENGTH: 40
<212> TYPE: DNA

<213> ORGANISM: Artificial
<220> FEATURE:
<223> OTHER INFORMATION: Synthetic Construct

<400> SEQUENCE: 148
agcaactggg acagatcgac agcctctcat ttcaagtcac 40

<210> SEQ ID NO 149
<211> LENGTH: 40
<212> TYPE: DNA
<213> ORGANISM: Artificial
<220> FEATURE:
<223> OTHER INFORMATION: Synthetic Construct

<400> SEQUENCE: 149
aacggttgct ctcataggag tgatgccgat tcatttccac 40

<210> SEQ ID NO 150
<211> LENGTH: 40
<212> TYPE: DNA
<213> ORGANISM: Artificial
<220> FEATURE:
<223> OTHER INFORMATION: Synthetic Construct

<400> SEQUENCE: 150
aacggttgct ctcataagag tgacgccgat tcatttccac 40

<210> SEQ ID NO 151
<211> LENGTH: 40
<212> TYPE: DNA
<213> ORGANISM: Artificial
<220> FEATURE:
<223> OTHER INFORMATION: Synthetic Construct

<400> SEQUENCE: 151
aacggctgct ctcataagag tgatgccgat tcatttccac 40

<210> SEQ ID NO 152
<211> LENGTH: 40
<212> TYPE: DNA
<213> ORGANISM: Artificial
<220> FEATURE:
<223> OTHER INFORMATION: Synthetic Construct

<400> SEQUENCE: 152
agcaactggg acagatcgac agcctttcac ttcaagtcac 40

<210> SEQ ID NO 153
<211> LENGTH: 40
<212> TYPE: DNA
<213> ORGANISM: Artificial
<220> FEATURE:
<223> OTHER INFORMATION: Synthetic Construct

<400> SEQUENCE: 153
ctctcatttc agccgatcat acctcaatgt agataagcac 40

<210> SEQ ID NO 154
<211> LENGTH: 40
<212> TYPE: DNA
<213> ORGANISM: Artificial
<220> FEATURE:
<223> OTHER INFORMATION: Synthetic Construct

<400> SEQUENCE: 154
agcaactggg gcagatcgac agcctttcat ttcaagtcac 40

<210> SEQ ID NO 155
<211> LENGTH: 40
<212> TYPE: DNA
<213> ORGANISM: Artificial
<220> FEATURE:
<223> OTHER INFORMATION: Synthetic Construct

<400> SEQUENCE: 155
agcaactggg acagatcgac agcctttcat ttcaagtcgc 40

<210> SEQ ID NO 156
<211> LENGTH: 40
<212> TYPE: DNA
<213> ORGANISM: Artificial
<220> FEATURE:
<223> OTHER INFORMATION: Synthetic Construct

<400> SEQUENCE: 156
agcaactggg acagatcgac agcctttcat ctcaagtcac 40

<210> SEQ ID NO 157
<211> LENGTH: 40
<212> TYPE: DNA
<213> ORGANISM: Artificial
<220> FEATURE:
<223> OTHER INFORMATION: Synthetic Construct

<400> SEQUENCE: 157
agaaactggg acagatcgac agcctttcat ttcaagccac 40

<210> SEQ ID NO 158
<211> LENGTH: 40
<212> TYPE: DNA
<213> ORGANISM: Artificial
<220> FEATURE:
<223> OTHER INFORMATION: Synthetic Construct

<400> SEQUENCE: 158
aacggttgct ctcataagag tgatgccgac tcatttccac 40

<210> SEQ ID NO 159
<211> LENGTH: 40
<212> TYPE: DNA
<213> ORGANISM: Artificial
<220> FEATURE:
<223> OTHER INFORMATION: Synthetic Construct

<400> SEQUENCE: 159
ctttcatttc agccgatcat acctcgatgt agataagcac 40

<210> SEQ ID NO 160
<211> LENGTH: 40
<212> TYPE: DNA
<213> ORGANISM: Artificial
<220> FEATURE:
<223> OTHER INFORMATION: Synthetic Construct

<400> SEQUENCE: 160
ctttcacttc agccgatcat acctcaatgt agataagcac 40

<210> SEQ ID NO 161
<211> LENGTH: 40
<212> TYPE: DNA
<213> ORGANISM: Artificial
<220> FEATURE:

<223> OTHER INFORMATION: Synthetic Construct

<400> SEQUENCE: 161
aacggttgct ctcataagag tgatgccgat tcatttccgc 40

<210> SEQ ID NO 162
<211> LENGTH: 40
<212> TYPE: DNA
<213> ORGANISM: Artificial
<220> FEATURE:
<223> OTHER INFORMATION: Synthetic Construct

<400> SEQUENCE: 162
aacaactggg acagatcgac agcctttcat ttcaagtcac 40

<210> SEQ ID NO 163
<211> LENGTH: 40
<212> TYPE: DNA
<213> ORGANISM: Artificial
<220> FEATURE:
<223> OTHER INFORMATION: Synthetic Construct

<400> SEQUENCE: 163
agcaactggg acagatcgac agcccttcat ttcaagtcac 40

<210> SEQ ID NO 164
<211> LENGTH: 40
<212> TYPE: DNA
<213> ORGANISM: Artificial
<220> FEATURE:
<223> OTHER INFORMATION: Synthetic Construct

<400> SEQUENCE: 164
ctttcatttc agccgatcat acctcagtgt agataagcac 40

<210> SEQ ID NO 165
<211> LENGTH: 40
<212> TYPE: DNA
<213> ORGANISM: Artificial
<220> FEATURE:
<223> OTHER INFORMATION: Synthetic Construct

<400> SEQUENCE: 165
ctttcatttc ggccgatcat acctcaatgt agataagcac 40

<210> SEQ ID NO 166
<211> LENGTH: 40
<212> TYPE: DNA
<213> ORGANISM: Artificial
<220> FEATURE:
<223> OTHER INFORMATION: Synthetic Construct

<400> SEQUENCE: 166
aacggttgct ctcacaagag tgacgccgat tcatttccac 40

<210> SEQ ID NO 167
<211> LENGTH: 40
<212> TYPE: DNA
<213> ORGANISM: Artificial
<220> FEATURE:
<223> OTHER INFORMATION: Synthetic Construct

<400> SEQUENCE: 167
agcaactggg acagatcgac agcctttcat ttcgagtcac 40

<210> SEQ ID NO 168
<211> LENGTH: 40
<212> TYPE: DNA
<213> ORGANISM: Artificial
<220> FEATURE:
<223> OTHER INFORMATION: Synthetic Construct

<400> SEQUENCE: 168
ctttcatttc agccgatcat accacaatgt agataagcac 40

<210> SEQ ID NO 169
<211> LENGTH: 40
<212> TYPE: DNA
<213> ORGANISM: Artificial
<220> FEATURE:
<223> OTHER INFORMATION: Synthetic Construct

<400> SEQUENCE: 169
aacggttgct tccataagag tgatgccgat tcatttccac 40

<210> SEQ ID NO 170
<211> LENGTH: 40
<212> TYPE: DNA
<213> ORGANISM: Artificial
<220> FEATURE:
<223> OTHER INFORMATION: Synthetic Construct

<400> SEQUENCE: 170
gacggttgcc ctcataagag tgatgccgat tcatttccac 40

<210> SEQ ID NO 171
<211> LENGTH: 40
<212> TYPE: DNA
<213> ORGANISM: Artificial
<220> FEATURE:
<223> OTHER INFORMATION: Synthetic Construct

<400> SEQUENCE: 171
cacccctcgg atcttcttct ttattagatt catttcagag 40

<210> SEQ ID NO 172
<211> LENGTH: 40
<212> TYPE: DNA
<213> ORGANISM: Artificial
<220> FEATURE:
<223> OTHER INFORMATION: Synthetic Construct

<400> SEQUENCE: 172
aacggttgct ctcgtaagag tgatgccgat tcatttccac 40

<210> SEQ ID NO 173
<211> LENGTH: 40
<212> TYPE: DNA
<213> ORGANISM: Artificial
<220> FEATURE:
<223> OTHER INFORMATION: Synthetic Construct

<400> SEQUENCE: 173
agcaactggg acagatcggc agcctttcat ttcaagtcac 40

<210> SEQ ID NO 174
<211> LENGTH: 40
<212> TYPE: DNA
<213> ORGANISM: Artificial
<220> FEATURE:
<223> OTHER INFORMATION: Synthetic Construct

<400> SEQUENCE: 174
aacggttgct ctcataagag cgatgccgat tcatttccac 40

<210> SEQ ID NO 175
<211> LENGTH: 40
<212> TYPE: DNA
<213> ORGANISM: Artificial
<220> FEATURE:
<223> OTHER INFORMATION: Synthetic Construct

<400> SEQUENCE: 175
ctttcatttc agccgatcat atctcaatgt agataagcac 40

<210> SEQ ID NO 176
<211> LENGTH: 40
<212> TYPE: DNA
<213> ORGANISM: Artificial
<220> FEATURE:
<223> OTHER INFORMATION: Synthetic Construct

<400> SEQUENCE: 176
aacggttgct ctcataagag tgatgctgat tcatttccac 40

<210> SEQ ID NO 177
<211> LENGTH: 40
<212> TYPE: DNA
<213> ORGANISM: Artificial
<220> FEATURE:
<223> OTHER INFORMATION: Synthetic Construct

<400> SEQUENCE: 177
aacggttgct ctcataagag tgatgccgat tcacttccac 40

<210> SEQ ID NO 178
<211> LENGTH: 40
<212> TYPE: DNA
<213> ORGANISM: Artificial
<220> FEATURE:
<223> OTHER INFORMATION: Synthetic Construct

<400> SEQUENCE: 178
ccctggcatt gcaaggttga ttctccgatc attttcacac 40

<210> SEQ ID NO 179
<211> LENGTH: 40
<212> TYPE: DNA
<213> ORGANISM: Artificial
<220> FEATURE:
<223> OTHER INFORMATION: Synthetic Construct

<400> SEQUENCE: 179
aacggttgtt cccataagag tgatgccgat tcatttccac 40

<210> SEQ ID NO 180
<211> LENGTH: 40
<212> TYPE: DNA
<213> ORGANISM: Artificial
<220> FEATURE:
<223> OTHER INFORMATION: Synthetic Construct

<400> SEQUENCE: 180
agcaactggg acggatcgac agcctttcat ttcaagtcac 40

<210> SEQ ID NO 181
<211> LENGTH: 40

<212> TYPE: DNA
<213> ORGANISM: Artificial
<220> FEATURE:
<223> OTHER INFORMATION: Synthetic Construct

<400> SEQUENCE: 181
cttccatttc agccgatcat acctcaatgt agataagcac 40

<210> SEQ ID NO 182
<211> LENGTH: 40
<212> TYPE: DNA
<213> ORGANISM: Artificial
<220> FEATURE:
<223> OTHER INFORMATION: Synthetic Construct

<400> SEQUENCE: 182
ctttcatttc agccgatcgt acctcaatgt agataagcac 40

<210> SEQ ID NO 183
<211> LENGTH: 40
<212> TYPE: DNA
<213> ORGANISM: Artificial
<220> FEATURE:
<223> OTHER INFORMATION: Synthetic Construct

<400> SEQUENCE: 183
aacggttgct ctcataagag tgatgccgat tcattcccac 40

<210> SEQ ID NO 184
<211> LENGTH: 40
<212> TYPE: DNA
<213> ORGANISM: Artificial
<220> FEATURE:
<223> OTHER INFORMATION: Synthetic Construct

<400> SEQUENCE: 184
ctttcatttc agccgatcat acctcaacgt agataagcac 40

<210> SEQ ID NO 185
<211> LENGTH: 40
<212> TYPE: DNA
<213> ORGANISM: Artificial
<220> FEATURE:
<223> OTHER INFORMATION: Synthetic Construct

<400> SEQUENCE: 185
agcaactggg acaggtcgac agcctttcat ttcaagtcac 40

<210> SEQ ID NO 186
<211> LENGTH: 11
<212> TYPE: DNA
<213> ORGANISM: Artificial
<220> FEATURE:
<223> OTHER INFORMATION: Synthetic Construct

<400> SEQUENCE: 186
aagcacatct t 11

<210> SEQ ID NO 187
<211> LENGTH: 96
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (14)..(14)

-continued

<223> OTHER INFORMATION: n is adenosine ribonucleotide

<400> SEQUENCE: 187
ctatgaactg actntgacct cactaccaag cttttagcct ttcatttcag ccgatcatac 60
ctcaatgtag ataagcacat cttgtcatcg gaggct 96

<210> SEQ ID NO 188
<211> LENGTH: 96
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: n is adenosine ribonucleotide

<400> SEQUENCE: 188
ctatgaactg actntgacct cactaccaag cttttagccc ttcatttcag ccgatcatac 60
ctcaatgtag ataagcacat cttgtcatcg ggggct 96

<210> SEQ ID NO 189
<211> LENGTH: 61
<212> TYPE: DNA
<213> ORGANISM: Artificial
<220> FEATURE:
<223> OTHER INFORMATION: Synthetic Construct

<400> SEQUENCE: 189
ctttcatttc agccgatcat acctcaatgt agataagcac atcttgtcat cggaggctta 60
g 61

<210> SEQ ID NO 190
<211> LENGTH: 61
<212> TYPE: DNA
<213> ORGANISM: Artificial
<220> FEATURE:
<223> OTHER INFORMATION: Synthetic Construct

<400> SEQUENCE: 190
ccttcatttc agccgatcat acctcaatgt agataagcac atcttgtcat cgggtgctta 60
g 61